(12) United States Patent
Shaanan et al.

(10) Patent No.: US 8,961,432 B2
(45) Date of Patent: Feb. 24, 2015

(54) ANALYTE TESTING DEVICES

(71) Applicant: YofiMeter, LLC, La Jolla, CA (US)

(72) Inventors: Gad Shaanan, La Jolla, CA (US); Marc Goldman, La Jolla, CA (US)

(73) Assignee: YofiMeter, LLC, La Jolla, CA (US)

( * ) Notice: Subject to any disclaimer, the term of this patent is extended or adjusted under 35 U.S.C. 154(b) by 0 days.

(21) Appl. No.: 13/868,831

(22) Filed: Apr. 23, 2013

(65) Prior Publication Data

US 2013/0245392 A1  Sep. 19, 2013

Related U.S. Application Data

(63) Continuation of application No. 13/689,618, filed on Nov. 29, 2012, which is a continuation-in-part of application No. 13/188,399, filed on Jul. 21, 2011, now abandoned, which is a continuation-in-part of (Continued)

(51) Int. Cl.
*A61B 5/151* (2006.01)
*A61B 5/145* (2006.01)
(Continued)

(52) U.S. Cl.
CPC ............. *A61B 5/15113* (2013.01); *A61B 5/145* (2013.01); *A61B 5/15194* (2013.01);
(Continued)

(58) Field of Classification Search
CPC ........... A61B 5/1411; A61B 5/150022; A61B 5/15019; A61B 5/150358; A61B 5/151
USPC ............................ 600/583, 584; 606/181–183
See application file for complete search history.

(56) References Cited

U.S. PATENT DOCUMENTS 4,794,926 A  1/1989  Munsch et al.
4,936,833 A  6/1990  Sams
(Continued)

FOREIGN PATENT DOCUMENTS

CA   2526543 A1   1/2005
CA   2544953 A1   10/2006
(Continued)

OTHER PUBLICATIONS

Accu-Chek Mobile System, Blood Glucose Meter, Roche Ltd., Feb. 23, 2011, http://www.accu-check.co.uk/gb/products/metersystems/mobile.html.

(Continued)

*Primary Examiner* — Max Hindenburg
*Assistant Examiner* — John Pani
(74) *Attorney, Agent, or Firm* — Perkins Coie LLP

(57) ABSTRACT

Systems, devices, techniques and methods are disclosed for implementing an actuator mechanism of an analyte testing device. In one aspect, a method to test an analyte includes advancing an analyte sensor from a first position within a sensor cartridge of an analyte testing device to a second position that exposes at least a portion of the analyte sensor outside of the device, advancing a lancet projecting component from an initial position to a cocked position for a subsequent projection of a lancet, in which the advancing the analyte sensor and the advancing the lancet projecting component are initiated by a single operation, projecting the lancet to expose at least a portion of the lancet outside of the device, receiving a testing sample including an analyte at the exposed portion of the analyte sensor, processing the testing sample to determine a parameter of the analyte, and ejecting the analyte sensor from the device.

16 Claims, 31 Drawing Sheets

Related U.S. Application Data application No. 13/187,360, filed on Jul. 20, 2011, which is a continuation-in-part of application No. 13/165,621, filed on Jun. 21, 2011, now abandoned, which is a continuation-in-part of application No. 13/187,397, filed on Jul. 20, 2011, now Pat. No. 8,333,716, which is a continuation-in-part of application No. 13/165,621, filed on Jun. 21, 2011, now abandoned.

(51) Int. Cl.
- *A61B 5/15* (2006.01)
- *A61B 5/00* (2006.01)
- *A61B 5/11* (2006.01)
- *A61B 5/157* (2006.01)

(52) U.S. Cl.
CPC ....... *A61B5/150175* (2013.01); *A61B 5/15148* (2013.01); *A61B 5/0004* (2013.01); *A61B 5/150824* (2013.01); *A61B 5/742* (2013.01); *A61B 5/1118* (2013.01); *A61B 5/746* (2013.01); *A61B 5/150961* (2013.01); *A61B 5/150022* (2013.01); *A61B 5/157* (2013.01); *A61B 5/14532* (2013.01); *A61B 5/1513* (2013.01); *A61B 5/150267* (2013.01); *A61B 5/150358* (2013.01); *A61B 5/150412* (2013.01); *A61B 5/15117* (2013.01); *A61B 5/15153* (2013.01); *A61B 5/15174* (2013.01)
USPC .......................................... 600/583; 606/181

(56) References Cited

U.S. PATENT DOCUMENTS

| | | |
|---|---|---|
| 5,064,098 A | 11/1991 | Hutter, III et al. |
| 5,196,025 A | 3/1993 | Ranalletta et al. |
| 5,269,762 A | 12/1993 | Armbruster et al. |
| 5,279,294 A * | 1/1994 | Anderson et al. ............. 600/322 |
| 5,307,263 A | 4/1994 | Brown |
| 5,322,511 A | 6/1994 | Armbruster et al. |
| 5,536,249 A | 7/1996 | Castellano et al. |
| 5,569,186 A | 10/1996 | Lord et al. |
| 5,637,095 A | 6/1997 | Nason et al. |
| 5,728,074 A | 3/1998 | Castellano et al. |
| 5,871,494 A | 2/1999 | Simons et al. |
| 5,918,603 A | 7/1999 | Brown |
| 5,971,941 A * | 10/1999 | Simons et al. ................ 600/573 |
| 6,045,537 A | 4/2000 | Klitmose |
| 6,071,294 A | 6/2000 | Simons et al. |
| 6,146,361 A | 11/2000 | DiBiasi et al. |
| 6,228,100 B1 * | 5/2001 | Schraga ........................ 606/183 |
| 6,270,455 B1 | 8/2001 | Brown |
| 6,287,283 B1 | 9/2001 | Ljunggreen et al. |
| 6,332,871 B1 | 12/2001 | Douglas et al. |
| 6,364,889 B1 | 4/2002 | Kheiri et al. |
| 6,454,746 B1 | 9/2002 | Bydlon et al. |
| 6,468,287 B1 | 10/2002 | Baugh |
| 6,472,220 B1 | 10/2002 | Simons et al. |
| 6,474,219 B2 | 11/2002 | Klitmose et al. |
| 6,482,186 B1 | 11/2002 | Douglas et al. |
| 6,575,900 B1 | 6/2003 | Zweig et al. |
| 6,582,404 B1 | 6/2003 | Klitgaard et al. |
| 6,585,698 B1 | 7/2003 | Packman et al. |
| 6,589,229 B1 | 7/2003 | Connelly et al. |
| 6,599,272 B1 | 7/2003 | Hjertman et al. |
| 6,616,616 B2 | 9/2003 | Fritz et al. |
| 6,783,537 B1 | 8/2004 | Kuhr et al. |
| 6,827,899 B2 | 12/2004 | Maisey et al. |
| 6,849,237 B2 | 2/2005 | Housefield et al. |
| 6,872,358 B2 | 3/2005 | Hagen et al. |
| 6,979,326 B2 | 12/2005 | Mann et al. |
| 6,997,343 B2 | 2/2006 | May et al. |
| 6,997,911 B2 | 2/2006 | Klitmose |
| 7,025,774 B2 | 4/2006 | Freeman et al. |
| 7,066,909 B1 | 6/2006 | Peter et al. |
| 7,094,221 B2 | 8/2006 | Veasey et al. |
| 7,133,329 B2 | 11/2006 | Skyggebjerg et al. |
| 7,144,384 B2 | 12/2006 | Gorman et al. |
| 7,175,642 B2 | 2/2007 | Briggs et al. |
| 7,192,405 B2 | 3/2007 | DeNuzzio et al. |
| 7,198,615 B2 | 4/2007 | Langley et al. |
| 7,211,096 B2 | 5/2007 | Kuhr et al |
| 7,220,248 B2 | 5/2007 | Mernoe |
| 7,229,288 B2 | 6/2007 | Stuart et al. |
| 7,258,693 B2 | 8/2007 | Freeman et al. |
| 7,261,691 B1 | 8/2007 | Asomani |
| 7,291,132 B2 | 11/2007 | DeRuntz et al. |
| 7,344,507 B2 | 3/2008 | Briggs et al. |
| 7,360,045 B2 | 4/2008 | Maezawa |
| 7,404,796 B2 | 7/2008 | Ginsberg |
| 7,430,825 B2 | 10/2008 | Vanek et al. |
| 7,534,226 B2 | 5/2009 | Mernoe et al. |
| 7,566,419 B2 | 7/2009 | Schulat et al. |
| 7,582,063 B2 | 9/2009 | Wurster et al. |
| 7,662,065 B1 | 2/2010 | Kahn et al. |
| 7,704,231 B2 | 4/2010 | Pongpairochana et al. |
| 7,708,717 B2 | 5/2010 | Estes et al. |
| 7,713,229 B2 | 5/2010 | Veit et al. |
| 7,713,238 B2 | 5/2010 | Mernoe |
| 7,713,240 B2 | 5/2010 | Istoc et al. |
| 7,722,536 B2 | 5/2010 | Goodnow |
| 7,753,879 B2 | 7/2010 | Mernoe |
| 7,775,975 B2 | 8/2010 | Brister et al. |
| 7,776,030 B2 | 8/2010 | Estes et al. |
| 7,779,183 B2 | 8/2010 | Koehler et al. |
| 7,785,288 B2 | 8/2010 | Mernoe et al. |
| 7,785,338 B2 | 8/2010 | Kuhr et al. |
| 7,789,859 B2 | 9/2010 | Estes et al. |
| 7,794,426 B2 | 9/2010 | Briones et al. |
| 7,794,427 B2 | 9/2010 | Estes et al. |
| 7,794,428 B2 | 9/2010 | Estes et al. |
| 7,794,430 B2 | 9/2010 | Langley et al. |
| RE41,956 E | 11/2010 | Klitgaard et al. |
| 7,828,528 B2 | 11/2010 | Estes et al. |
| 7,833,196 B2 | 11/2010 | Estes et al. |
| 7,848,765 B2 | 12/2010 | Phillips et al. |
| 7,862,506 B2 | 1/2011 | Brown |
| 7,867,165 B2 | 1/2011 | Brown |
| 7,869,852 B2 | 1/2011 | Brown |
| 7,871,376 B2 | 1/2011 | Brown |
| 7,879,026 B2 | 2/2011 | Estes et al. |
| 7,883,015 B2 | 2/2011 | Ackermann et al. |
| 7,887,511 B2 | 2/2011 | Mernoe et al. |
| 7,887,512 B2 | 2/2011 | Estes et al. |
| 7,887,682 B2 | 2/2011 | Wang et al. |
| 7,892,183 B2 | 2/2011 | Boecker et al. |
| 7,892,185 B2 | 2/2011 | Freeman et al. |
| 7,892,199 B2 | 2/2011 | Mhatre et al. |
| 7,914,742 B2 | 3/2011 | Arbogast et al. |
| 7,922,708 B2 | 4/2011 | Estes et al. |
| 7,922,971 B2 | 4/2011 | Bryer et al. |
| 7,935,063 B2 | 5/2011 | Roe |
| 7,935,076 B2 | 5/2011 | Estes et al. |
| 7,935,105 B2 | 5/2011 | Miller et al. |
| 7,938,803 B2 | 5/2011 | Mernoe et al. |
| 7,951,114 B2 | 5/2011 | Rush et al. |
| 7,955,791 B2 | 6/2011 | Dinello et al. |
| 7,967,784 B2 | 6/2011 | Pongpairochana et al. |
| 7,972,267 B2 | 7/2011 | Brown |
| 7,981,034 B2 | 7/2011 | Jennewine et al. |
| 7,981,084 B2 | 7/2011 | Estes et al. |
| 7,981,102 B2 | 7/2011 | Patel et al. |
| 8,007,739 B2 | 8/2011 | Pollack et al. |
| 8,021,345 B2 | 9/2011 | Veasey et al. |
| 8,029,443 B2 | 10/2011 | Goodnow |
| 8,032,226 B2 | 10/2011 | Miller et al. |
| 8,057,436 B2 | 11/2011 | Causey et al. |
| 8,066,639 B2 | 11/2011 | Nelson et al. |
| RE43,039 E | 12/2011 | Brister et al. |
| 8,073,008 B2 | 12/2011 | Mehta et al. |
| 8,095,692 B2 | 1/2012 | Mehta et al. |
| 8,099,074 B2 | 1/2012 | Ebner et al. |
| 8,105,279 B2 | 1/2012 | Mernoe et al. |

(56) References Cited

U.S. PATENT DOCUMENTS

| | | |
|---|---|---|
| 8,106,534 B2 | 1/2012 | Spurlin et al. |
| 8,109,921 B2 | 2/2012 | Estes et al. |
| 8,118,770 B2 | 2/2012 | Galley et al. |
| 8,121,857 B2 | 2/2012 | Galasso et al. |
| 8,133,178 B2 | 3/2012 | Brauker et al. |
| 8,140,312 B2 | 3/2012 | Hayter et al. |
| 8,152,764 B2 | 4/2012 | Istoc et al. |
| 8,152,765 B2 | 4/2012 | Briones et al. |
| 8,192,394 B2 | 6/2012 | Estes et al. |
| 8,204,729 B2 | 6/2012 | Sher |
| 8,206,340 B2 | 6/2012 | Arefieg |
| 8,226,891 B2 | 7/2012 | Sloan et al. |
| 8,246,540 B2 | 8/2012 | Ginsberg |
| 8,255,238 B2 | 8/2012 | Powell et al. |
| 8,285,487 B2 | 10/2012 | Bergstrom et al. |
| 8,308,679 B2 | 11/2012 | Hanson et al. |
| 2002/0170823 A1 | 11/2002 | Housefield et al. |
| 2002/0177761 A1 | 11/2002 | Orloff et al. |
| 2003/0038407 A1 | 2/2003 | Bethune |
| 2003/0083685 A1 | 5/2003 | Freeman et al. |
| 2003/0153900 A1 | 8/2003 | Aceti et al. |
| 2003/0191415 A1* | 10/2003 | Moerman et al. ............ 600/584 |
| 2004/0044272 A1 | 3/2004 | Moerman et al. |
| 2004/0082878 A1 | 4/2004 | Baldwin et al. |
| 2004/0098009 A1 | 5/2004 | Boecker et al. |
| 2004/0127819 A1 | 7/2004 | Roe |
| 2004/0172284 A1 | 9/2004 | Sullivan et al. |
| 2005/0015020 A1 | 1/2005 | LeVaughn et al. |
| 2005/0227370 A1 | 10/2005 | Ramel et al. |
| 2005/0238538 A1 | 10/2005 | Braig et al. |
| 2006/0052724 A1* | 3/2006 | Roe ............................. 600/583 |
| 2006/0094986 A1* | 5/2006 | Neel et al. .................... 600/583 |
| 2006/0173417 A1 | 8/2006 | Rosen et al. |
| 2006/0229502 A1 | 10/2006 | Pollock et al. |
| 2006/0245131 A1 | 11/2006 | Ramey et al. |
| 2006/0279431 A1 | 12/2006 | Bakarania et al. |
| 2006/0281187 A1 | 12/2006 | Emery et al. |
| 2007/0007183 A1 | 1/2007 | Schulat et al. |
| 2007/0060803 A1* | 3/2007 | Liljeryd et al. ............... 600/301 |
| 2007/0073590 A1 | 3/2007 | Cosentino et al. |
| 2007/0088271 A1 | 4/2007 | Richards |
| 2007/0173740 A1 | 7/2007 | Chan et al. |
| 2007/0179404 A1 | 8/2007 | Escutia et al. |
| 2007/0255181 A1* | 11/2007 | Alvarez-Icaza et al. ...... 600/583 |
| 2008/0058631 A1 | 3/2008 | Draudt et al. |
| 2008/0139910 A1 | 6/2008 | Mastrototaro et al. |
| 2008/0167578 A1 | 7/2008 | Bryer et al. |
| 2008/0200838 A1 | 8/2008 | Goldberger et al. |
| 2008/0234943 A1 | 9/2008 | Ray et al. |
| 2009/0010802 A1 | 1/2009 | Joseph et al. |
| 2009/0048536 A1 | 2/2009 | Freeman et al. |
| 2009/0050491 A1 | 2/2009 | Brown |
| 2009/0138207 A1 | 5/2009 | Cosentino et al. |
| 2009/0171589 A1 | 7/2009 | Kovatchev |
| 2009/0270765 A1 | 10/2009 | Ghesquiere et al. |
| 2009/0318865 A1 | 12/2009 | Moller et al. |
| 2009/0322513 A1 | 12/2009 | Hwang et al. |
| 2010/0016700 A1 | 1/2010 | Sieh et al. |
| 2010/0044261 A1 | 2/2010 | Yao et al. |
| 2010/0069730 A1 | 3/2010 | Bergstrom et al. |
| 2010/0087754 A1 | 4/2010 | Rush et al. |
| 2010/0094205 A1 | 4/2010 | Boyd et al. |
| 2010/0114025 A1 | 5/2010 | Moller |
| 2010/0151488 A1 | 6/2010 | Smith et al. |
| 2010/0212675 A1 | 8/2010 | Walling et al. |
| 2010/0218132 A1 | 8/2010 | Soni et al. |
| 2010/0261987 A1 | 10/2010 | Kamath et al. |
| 2010/0262380 A1 | 10/2010 | Matievich, Jr. et al. |
| 2010/0270149 A1 | 10/2010 | Wang et al. |
| 2010/0286563 A1 | 11/2010 | Bryer et al. |
| 2010/0312137 A1 | 12/2010 | Gilmour et al. |
| 2010/0317935 A1 | 12/2010 | Roe et al. |
| 2010/0331652 A1 | 12/2010 | Groll et al. |
| 2010/0331653 A1 | 12/2010 | Stafford |
| 2010/0332142 A1 | 12/2010 | Shadforth et al. |
| 2010/0332445 A1 | 12/2010 | Ray et al. |
| 2011/0009775 A1 | 1/2011 | Roe |
| 2011/0040165 A1 | 2/2011 | Williams, III |
| 2011/0054390 A1 | 3/2011 | Searle et al. |
| 2011/0077480 A1 | 3/2011 | Bloom et al. |
| 2011/0118771 A1 | 5/2011 | Ruan et al. |
| 2011/0124130 A1 | 5/2011 | Wagner et al. |
| 2011/0124996 A1 | 5/2011 | Reinke et al. |
| 2011/0132759 A1 | 6/2011 | Petyt et al. |
| 2011/0184343 A1 | 7/2011 | Veit et al. |
| 2011/0184653 A1 | 7/2011 | Ray et al. |
| 2011/0184752 A1 | 7/2011 | Ray et al. |
| 2011/0205064 A1 | 8/2011 | Strachan et al. |
| 2011/0228111 A1 | 9/2011 | Imagawa |
| 2011/0246235 A1 | 10/2011 | Powell et al. |
| 2013/0085349 A1* | 4/2013 | Shaanan et al. ............... 600/301 |

FOREIGN PATENT DOCUMENTS

| | | |
|---|---|---|
| CA | 2599573 A1 | 11/2006 |
| CA | 2607437 A1 | 12/2006 |
| CA | 2646279 A1 | 10/2007 |
| CA | 2669302 A1 | 6/2008 |
| CA | 2327127 C | 8/2010 |
| EP | 1399059 B1 | 8/2006 |
| EP | 1717924 A2 | 11/2006 |
| EP | 1328192 B1 | 1/2011 |
| EP | 2284747 A1 | 2/2011 |
| EP | 1664783 B1 | 5/2011 |
| EP | 2195050 B1 | 5/2011 |
| WO | 99/35487 A1 | 7/1999 |
| WO | 02/078533 A2 | 10/2002 |
| WO | 02/094092 A1 | 11/2002 |
| WO | 03/047426 A1 | 6/2003 |
| WO | 03/082091 A2 | 10/2003 |
| WO | 2007/010087 A2 | 1/2007 |
| WO | 2006/133435 A3 | 3/2007 |
| WO | 2006/122741 A3 | 4/2007 |
| WO | 2008/069932 A1 | 6/2008 |
| WO | 2007/112034 A3 | 9/2008 |
| WO | 2009/027950 A2 | 3/2009 |
| WO | 2009/146379 A1 | 12/2009 |
| WO | 2010/040089 A1 | 4/2010 |
| WO | 2010/049669 A1 | 5/2010 |
| WO | 2010/068617 A1 | 6/2010 |
| WO | 2010/054205 A3 | 9/2010 |
| WO | 2010/120563 A1 | 10/2010 |
| WO | 2010/134969 A1 | 11/2010 |
| WO | 2011/019657 A1 | 2/2011 |
| WO | 2010/009870 A8 | 3/2011 |
| WO | 2011/026053 A1 | 3/2011 |
| WO | 2011/008520 A3 | 4/2011 |
| WO | 2011/060923 A3 | 7/2011 |

OTHER PUBLICATIONS

Always Connected, Always Monitoring the Critical Signals You Need to Know, CST Critical Signal Technologies, your Link to Life, Farmington Hills, MI 48335.

Amy T., "Lifescan's New Diabetes iPhone App", Diabetes Mine: the all things diabetes blog, Mar 17, 2009, http://www.diabetesmine.com/2009/03/lifescans-new-diabetes-iphone-app.html.

Medline Docking Station for Glucose Meter, http://www.google.com/products/catalog?q=docking+station+for+glucose+meter&hl=en&um=1&ie=UTF-8&tbm=shop&cid=14673613440805108352&sa=X&ei=Eq-DTp2QGcnKiALyt-XwBw&ved=0CFIQ8wlwAA#.

OneTouch Ultra Link Lifescan Consumer Products, 2011, http://www.lifescan.com/products/meters/ultralink/.

Precision PCx Glucose Monitoring System—Medline and Abbott Diabetes Care Post Acute Care Bring You Fill Billing Capture, Compliance, and Accuracy in Blood Glucose Testing, Med Supplies Care, 2011, http://www.medsuppliescare.com/medsupply.cfm/Docking-Station-For-Precision-PCX-5650.

TRUEmanager—Track a healthier course to diabetes management, Nipro Diagnostics, 2010, http://www.niprodiagnostics.com/our_products/ma_true_manager.aspx.

(56) References Cited

OTHER PUBLICATIONS

TRUEresult Docking Station and USB Cable, Diabetes Health Supplies, 2011, http://www.diabeteshealthsupplies.com/products/TRUEresult-Docking-Station-and-USB-Cable.html.

Ramchandani et al., "New Technologies for Diabetes: A review of the present and the future," International Journal of Pediatric Endocrinology, 2012:28, 2012.

* cited by examiner

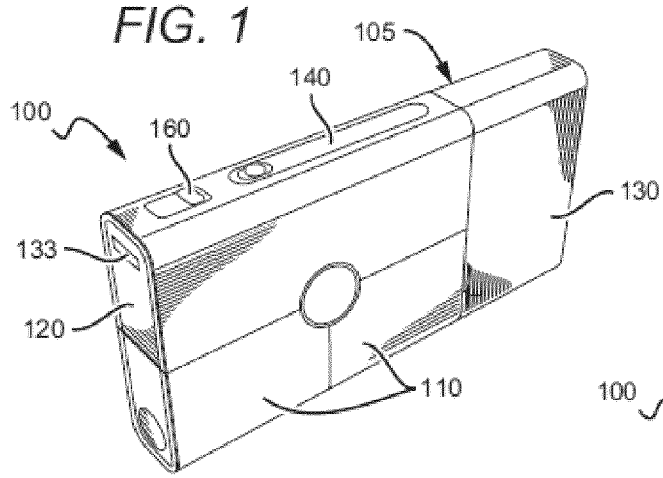
FIG. 1
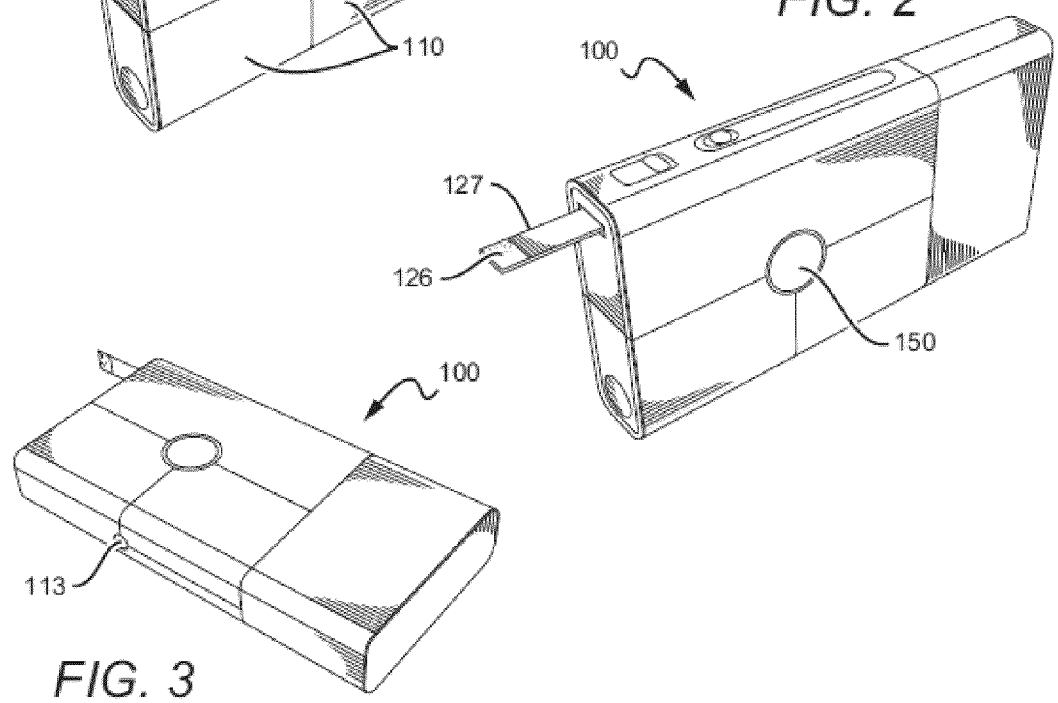
FIG. 2
FIG. 3
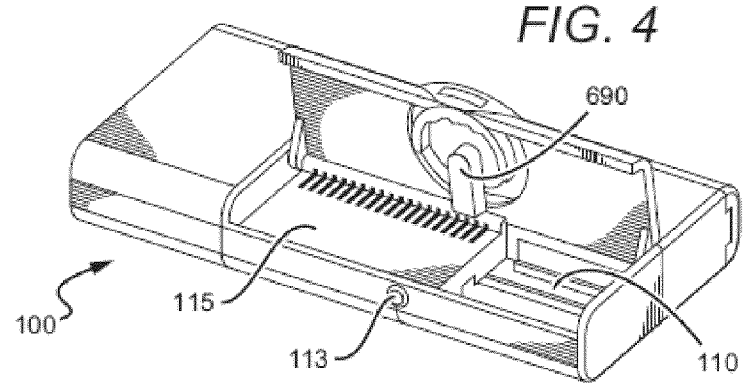
FIG. 4

REST POSITION

LEVER PULLED TO
COCK HAMMER AND
ADVANCE CASSETTE
TO NEXT LANCET

COCKED AND READY

BUTTON IS PRESSED
TO RELEASE HAMMER
AND PROJECT LANCET

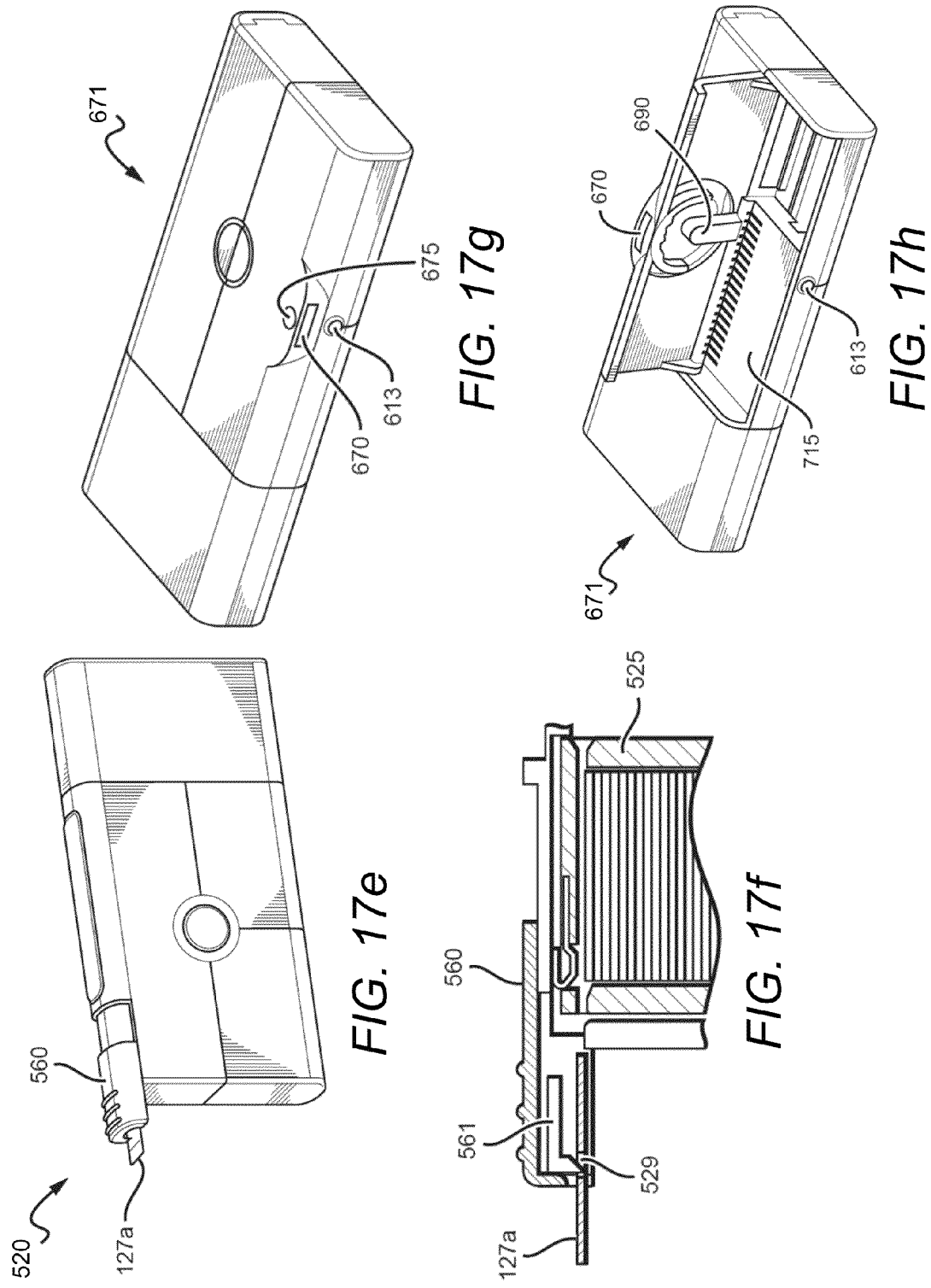

Initial position of the lancet cartridge 1803

Final position of the lancet cartridge 1803

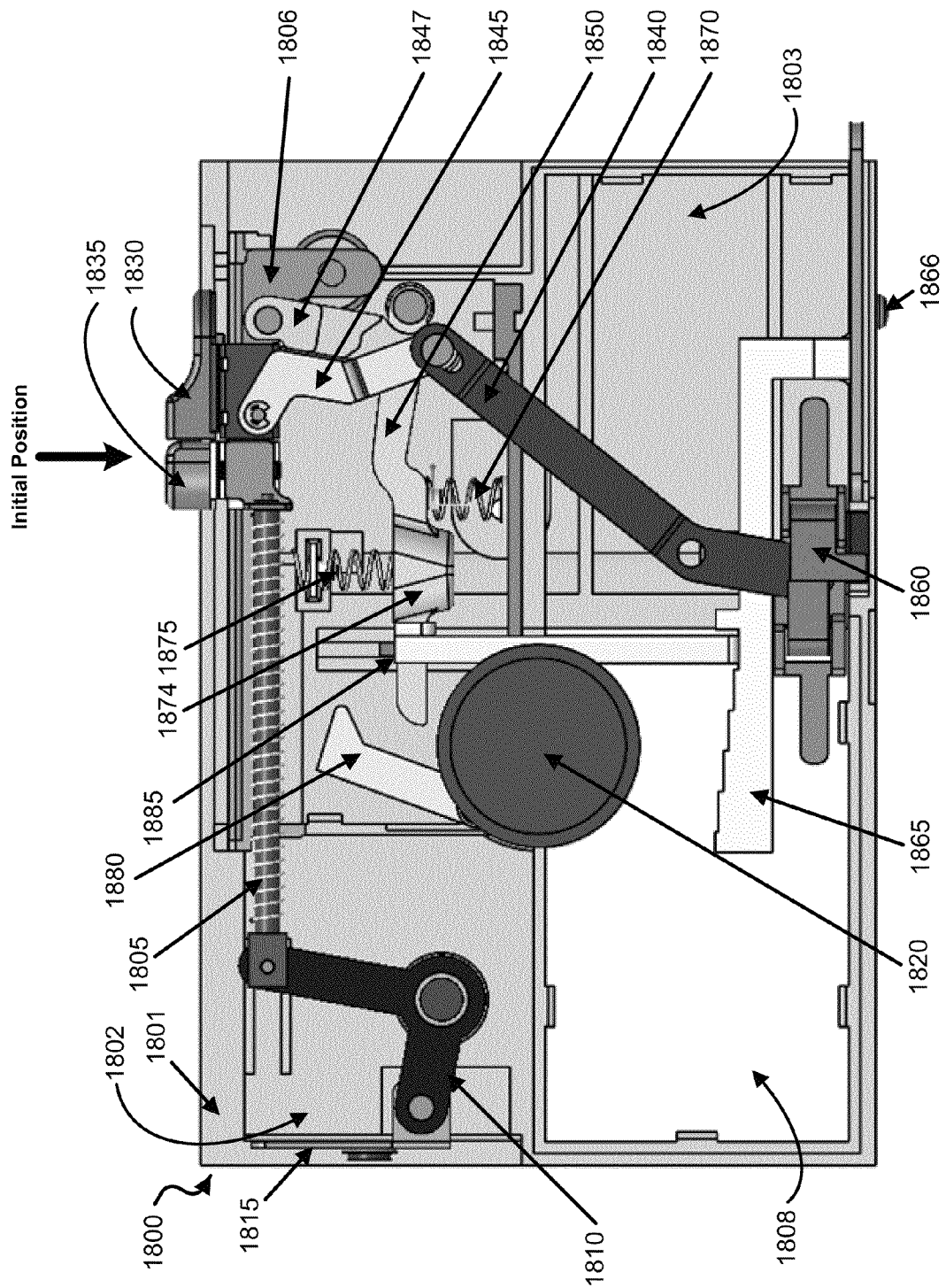

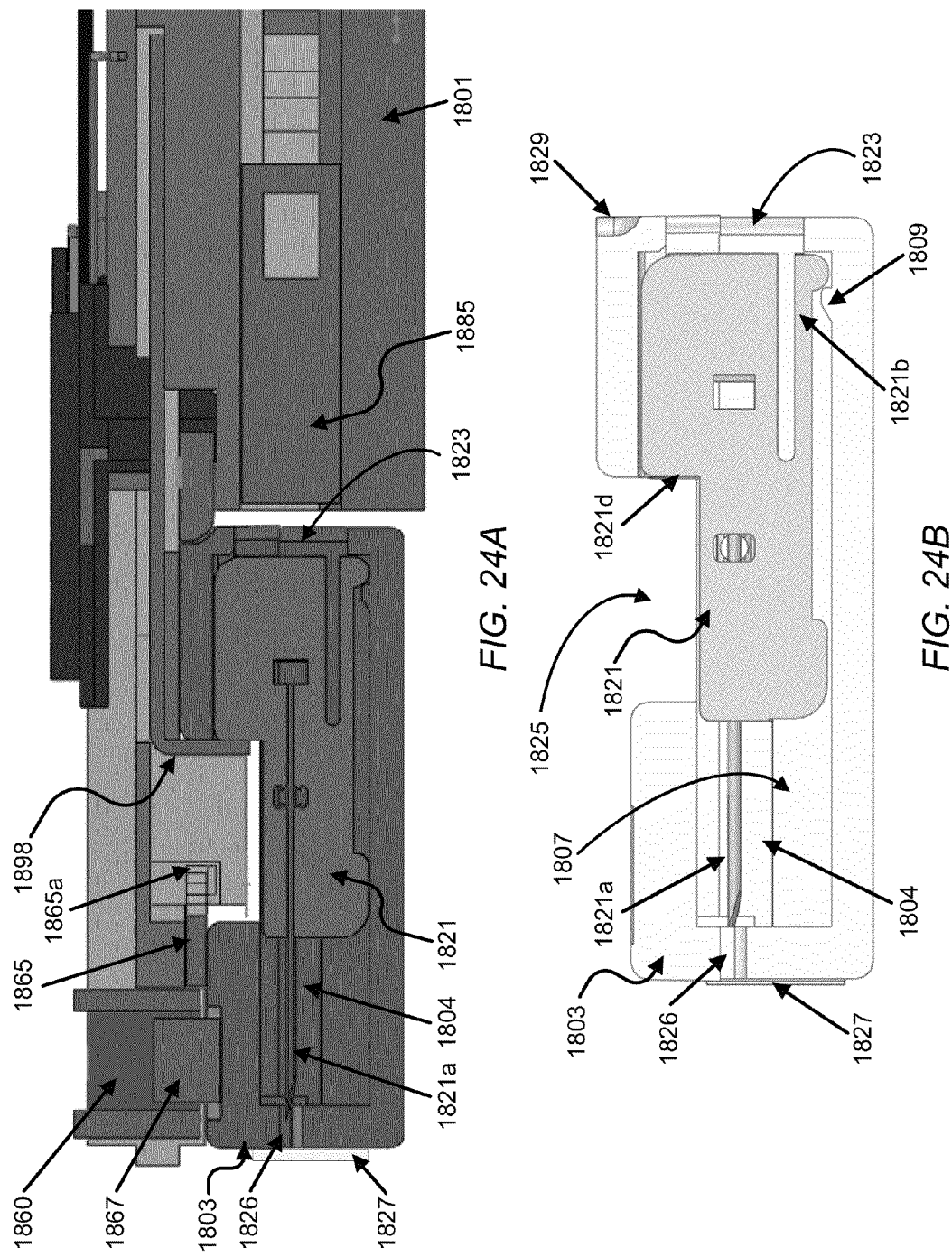

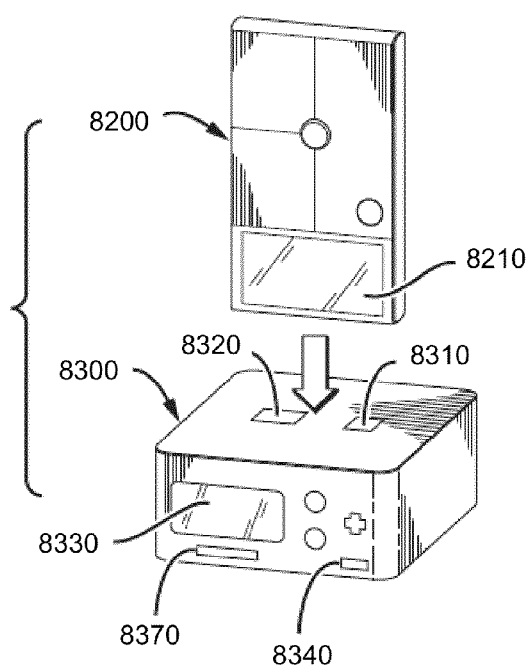
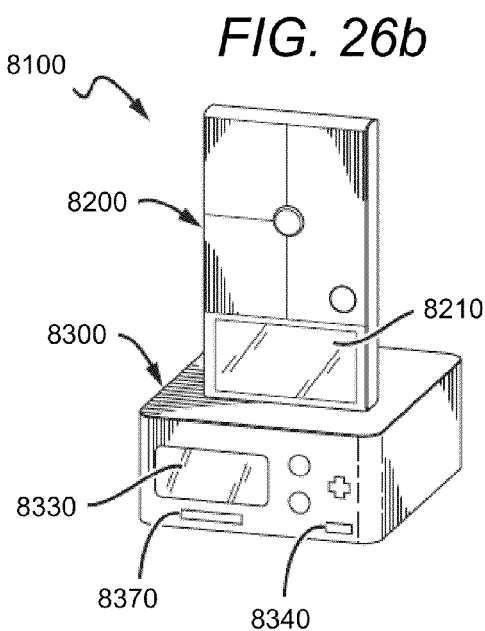
FIG. 26a
FIG. 26b
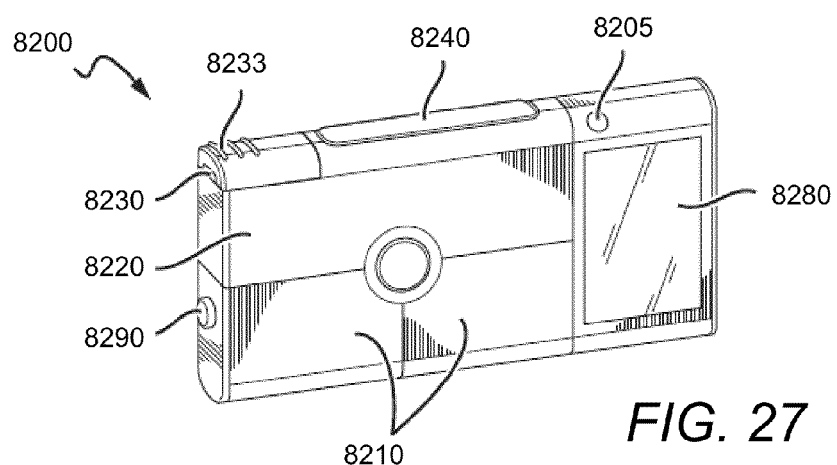
FIG. 27

ANALYTE TESTING DEVICES

PRIORITY CLAIM AND RELATED PATENT APPLICATIONS

This application is a continuation of, under 35 U.S.C. §120, U.S. patent application Ser. No. 13/689,618 entitled "ANALYTE TESTING DEVICES" and filed on Nov. 29, 2012, which is a continuation-in-part of U.S. patent application Ser. No. 13/188,399 entitled "COCKING AND ADVANCING MECHANISM FOR ANALYTE TESTING DEVICE" and filed on Jul. 21, 2011, now abandoned, which in turn is a continuation-in-part application of U.S. patent application Ser. No. 13/187,360 filed on Jul. 20, 2011 and U.S. patent application Ser. No. 13/187,397 filed on Jul. 20, 2011, now U.S. Pat. No. 8,333,716, which in turn are continuation-in-part applications of U.S. patent application Ser. No. 13/165,621 filed on Jun. 21, 2011, now abandoned. The entire contents of the before-mentioned patent applications are incorporated by reference as part of the disclosure of this application.

TECHNICAL FIELD

This patent document relates to analyte testing devices and related techniques.

BACKGROUND

Analyte testing devices play a critical roll in modern diagnosis and management of health-related issues. For example, a sample of human blood, urine, and/or saliva can be tested for glucose, fructosamine, hematocrit, hemoglobin blood oxygen saturation, lactates, iron, pH, cholesterol, liver enzymes (AST, ALT, alkaline phosphatase/GGT, LDH, bilirubin, etc), hormones, and other compounds.

For many diabetic patients, monitoring glucose levels and administering appropriate insulin dosages is a daily activity that requires a significant amount of time and mental energy. Current glucose meters and lancing devices often involve multiple devices, components, and supplies, and require numerous steps to monitor glucose levels. For example, conventional glucose monitoring systems may require numerous steps involving reading a test strip, readying a lancet, using the lancet, putting blood on the test strip and inserting the strip into the glucose meter, reading data from a meter, recording the data in a journal and remembering to bring the journal to the next doctor visit, and then putting away the strip and lancet packages, disposing of loose components, and storing the glucose meter. Thus, there is a need to reduce steps and simplify devices and supplies for monitoring analytes. Other needs include a compact analyte testing device and hands-free disposal of test strips.

Several known prior art references are directed at simplifying the devices and processes for monitoring analytes. Significantly, however, the prior art systems each appear to address only a subset of the convenience issues. U.S. Pat. No. 6,472,220 to Simons, for example, discloses an integrated lancing device and glucose meter. The device holds a cassette that stores a plurality of lancets and test strips. Each lancet is paired with a test strip into a single integrated unit, thus simplifying the number of separate supply components. Unfortunately, the test strip-lancet unit contemplated in Simons prevents the user from using lancets independently of the test strips.

Simons, and all other extrinsic materials discussed herein, are incorporated by reference in their entirety. Where a definition or use of a term in an incorporated reference is inconsistent or contrary to the definition of that term provided herein, the definition of that term provided herein applies and the definition of that term in the reference does not apply.

U.S. Pat. No. 7,192,405 to DeNuzzio also provides an integrated lancet-test strip unit, similar to Simons. DeNuzzio suffers from the same drawbacks as Simons.

U.S. Pat. No. 7,582,063 to Wurster discloses a glucose meter that includes a plurality of analyte sensors and a plurality of lancets on the same carrier. Each time a new blood test is performed, the carrier is rotated into position, which simultaneously exposes an analyte sensor, advances a lancet for use, and cocks a spring to operate the pre-positioned lancet. Since the analyte sensors and lancets are rotated together on the same carrier, exposing of an analyte sensor is not independent of advancing a lancet. That can be a disadvantage to a user who might want to use more than one sensor for a given stick (or for example where two different readings are desired), or might need to use two or more lancets to secure an adequate sample for a single sensor.

Wurster is also designed such that during use, the operative sensor is immediately adjacent (indeed surrounds) the operative lancet tip. That design could be viewed as being inherently problematic because the sensor will tend to sense components in the first amount of blood that is drawn. To avoid that problem it would be more desirable to expose the analyte sensor at a position at least several millimeters away from where the lancet is projected from the housing.

U.S. Pat. No. 4,794,926 to Munsch discloses a lancing device that holds a cartridge with a plurality of lancets. Rotating the cartridge in the lancing device simultaneously loads the next lancet into position for ejection while "cocking" the lancet for ejection. However, Munsch fails to integrate the lancing device with a glucose meter, and also fails to partially expose a test strip when the lancet cartridge is rotated.

U.S. Pat. Nos. 7,922,971, 6,997,343, 7,211,096, and 6,616,616 are other examples of known references that attempt to simplify methods and devices for monitoring glucose levels.

The POGO™ System by Intuity Medical, Inc. (see http://www.presspogo.com/pogo/system/) is a commercially available glucose and lancing device that is designed to simplify glucose monitoring. While the POGO™ System reduces the steps and components required, and is an improvement over many other systems, the POGO system fails to provide a separate lancet cartridge and test strip cartridge. As such, the user cannot use lancets independently of test strips.

It has yet to be appreciated that an analyte testing device can house a plurality of analyte sensors and a plurality of lancets, where a single operation of an actuator can expose an analyte sensor while advancing a lancet for projection for use, where the sensors are exposed at a distance of at least several millimeters from where the lancets are projected, and/or where the sensors and lancets can be operated independently from each other.

SUMMARY

The subject matter includes devices, systems, techniques and methods in which an analyte testing device can house a plurality of analyte sensors and a plurality of lancets, where a single operation of an actuator can eject an analyte sensor while advancing a lancet for projection for use.

In some aspects of disclosed embodiments, the analyte sensor is included in an analyte sensor cartridge. The cartridge preferably holds a plurality of analyte sensors. In other aspects of disclosed embodiments, each analyte sensor is disposed in a test unit (e.g., a test strip).

In yet other aspects of some disclosed embodiments, the lancet is included in a lancet cartridge. The lancet cartridge preferably holds a plurality of lancets.

In other aspects of disclosed embodiments, the actuator comprises a manually operated lever. In some embodiments, the mechanism is entirely manually operated. In other embodiments, the mechanism is operated at least in part by a motor.

In some aspects of disclosed embodiments, the mechanism includes a hammer, and the actuator operates to cock the hammer. For example, the hammer can be spring loaded and then released to eject a lancet for drawing a blood sample.

In yet other aspects of disclosed embodiments, the mechanism has a linkage that exposes the analyte sensor, advances the lancet for use, and cocks the hammer, all in a single motion of the actuator. In some embodiments, the single motion comprises pulling a lever. In some embodiments the mechanism includes a first link that exposes the analyte sensor, and a second link, different from the first link, that advances the advancing the lancet. Exposing of the analyte sensor is preferably done independently relative to advancing the lancet. For example, the mechanism can include a disengagement control that is capable of disengaging the actuator from either exposing the analyze sensor or advancing the lancet.

In some aspects of disclosed embodiments, the sensors are ejected at a distance of at least several millimeters from where the lancets are projected. In other aspects, the sensors and lancets can be operated independently from each other. For example, the sensors and lancets are each stored in a separate cartridge and the cartridges couple with the analyte testing device independently of one another.

Various features, aspects, and advantages of the inventive subject matter will become more apparent from the following detailed description of various embodiments, the accompanying drawing figures and claims.

BRIEF DESCRIPTION OF THE DRAWING

FIG. 1 is a top perspective view of one embodiment of an analyte testing device.

FIG. 2 is the device of FIG. 1, wherein an analyte sensor of a test unit has been exposed.

FIG. 3 is a bottom perspective view of the device of FIG. 1.

FIG. 4 is a back perspective view the device of FIG. 1.

FIGS. 17e and 17f show one embodiment of an analyte testing device with a no-contact test strip ejecting mechanism.

FIGS. 17g and 17h show perspective views of one embodiment of an analyte testing device with a wheel for adjusting lancet puncture depth and window for displaying depth setting.

FIGS. 19A and 19B show schematics illustrating an operation of the exemplary actuator mechanism of the analyte testing device.

FIGS. 24A-24E show schematics illustrating a firing operation of the exemplary lancet of the actuator mechanism.

FIGS. 26a and 26b are perspective views of one embodiment of an analyte testing system.

FIG. 27 is a perspective view of one embodiment of a handheld analyte testing device.

DETAILED DESCRIPTION

Figure 5:
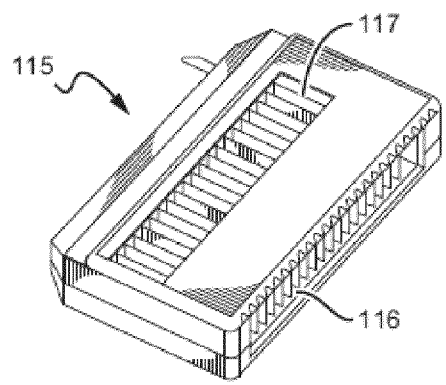
FIG. 5 is a perspective views of one embodiment of a lancet cartridge.

The following discussion provides example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

FIG. 1 shows an analyte testing device 100. The housing 105 of device 100 has a first compartment 110 and a second compartment 120, for storing a lancet cartridge 115 (see FIGS. 5-7) and an analyte sensor cartridge 125 (see FIGS. 8-9), respectively. The analyte sensor cartridge 125 contains test units 127 each having an analyte sensor 126 for contacting and sensing a particular analyte such as blood. Device 100 includes an exterior facet outside the second compartment 120 to have a slot 133 for receiving from, and for ejecting a test unit 127 out of, the analyte sensor cartridge 125, when device 100 is operated to perform a test. The first compartment 110 includes an exterior facet that is configured to include an opening or hole 113 for rejecting a lancet that allows a precise cut into a user for generating a small amount of bleeding for a blood test. The lancet cartridge 115 contained inside the first compartment 110 is designed to store a plurality of lancets 117 (see FIGS. 5 and 6) to allow a lancet 117 to be protruded at the hole 113 (see FIG. 3) during a test. Hole 113 and slot 133 are separated by a substantial distance (more than 5 mm), thus allowing a user to bleed out an initial amount of blood before applying a blood sample to an analyte sensor. In the illustrated example, hole 113 and slot 133 are on two different facets of device 100. Device 100 also has an electronics compartment 130 for housing conversion electronics 137 (see FIG. 12). Conversion electronics 137 are communicatively coupled to an analyte sensor 126 (see FIGS. 8 and 10) within cartridge 125. Conversion electronics 137 is configured to convert a signal from analyte sensor 126 into readable data (e.g., glucose levels).

The operation of device 100 will become more apparent from the following descriptions, including those with respect to FIGS. 11-14.

Device 100 has an actuator 140 comprising a lever. Actuator 140 can be cocked by operating the level to be in an actuated state to (i) ready a lancing device (e.g., cock a hammer, see FIGS. 11 and 14), (ii) expose an analyte sensor or test unit 127 (see FIGS. 2 and 14), and (iii) advance a lancet cartridge 115 for actuating a lancet 117 for taking a test (see FIGS. 11 and 13). Device 100 also has a test unit ejector 160, which advantageously allows for hands-free disposal of a used test strip 127 after each test.

The housing of device 100 can be made of plastic, metal, composite, or any other material with structural and mechanical properties suitable for housing a lancet cartridge, test strip cartridge, electronics, and a linkage mechanism. Device 100 can be designed to be compact for easy storage and for convenient portability. For example, device 100 can be configured to have a height no more than 50 mm, a width no more than 17 mm, and a length no more than 100 mm in some implementations while in more compact form for other implementations with the height being no more than 40 mm, a width being no more than 12 mm, and a length being no more than 75 mm. In some disclosed embodiments, the housing of device 100 comprises an outer protective shell made of a suitable shell material to protect the device components from elements or conditions in the surroundings. For example, the outer protective shell may be made of molded plastic and may include an inner desiccant liner to minimize exposure to moisture.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

Conversion electronics 137 preferably includes a facility for transmitting data and information out of the housing and to an external storage device (e.g., docking station, laptop, smart phone). It is contemplated that the data can be transmitted using a wireless protocol, and can even transmit data using two or more wireless protocols. Wired protocols and methods are also contemplated.

It is also contemplated that conversion electronics 137 can include a processor programmed to correlate individual instances of data and information derived from the data with time stamps. The processor can also be programmed to correlate individual instances of data with user-entered information such as voice recordings or text. In addition, the processor can be programmed to make an evaluation of the data and information, and send a notification to different recipients as a function of the evaluation. Yet still, the processor can be programmed to keep track of inventory of lancets and test strips, both within and outside the device, and re-order supplies as needed.

In other aspects of preferred embodiments, conversion electronics 137 includes a processor programmed to store voice recordings of diary information selected from the group consisting of supplies used or ordered, food eaten, exercise, medication taken, and estimated calories burned. The processor is also preferably programmed to prompt a user to use the device according to a pre-selected time and/or pre-selected time interval. Alternatively, electronics 137 can be equipped with an accelerometer or pedometer for measuring and calculating distance traveled and calories burned.

Conversion electronics 137 can also include a pedometer and/or accelerometer for calculating a distance traveled and calories burned. In such embodiments, electronics 137 preferably includes a processor for time-stamping the distances traveled and calories burned, and correlating this data with analyte test data.

FIG. 2 shows device 100 after actuator 140 has been cocked. The cocking of actuator 140 has caused a test unit 127 to be partially ejected from slot 133, thus exposing analyte sensor 126 (see FIGS. 8 and 10). Once actuator 140 has been cocked, a lancing device within device 100 can be projected by pressing button 150, causing one of a plurality of lancets 117 (see FIGS. 5 and 6) to exit from hole 113 (see FIG. 3).

FIG. 4 shows a back perspective view of device 100. A door on the backside of device 100 has been opened to reveal compartment 110. A lancet cartridge 115 is disposed within compartment 110. Device 100 has a spring-loaded return slider 690, which is configured to retract a lancet back into cartridge 115 after the lancet has been partially ejected for drawing a blood sample.

Figure 6:
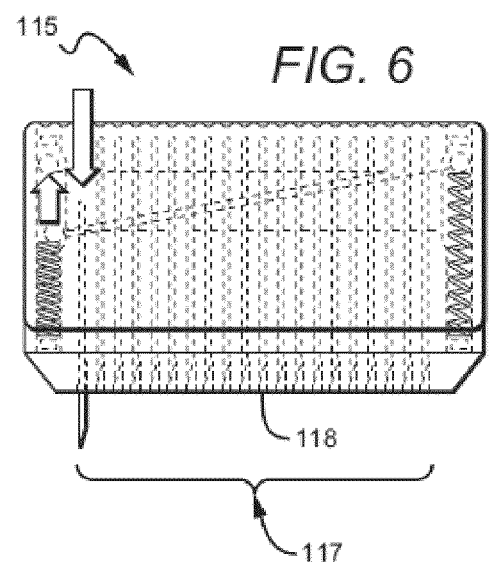
FIG. 6 is a side view of the lancet cartridge of FIG. 5.
Figure 7:
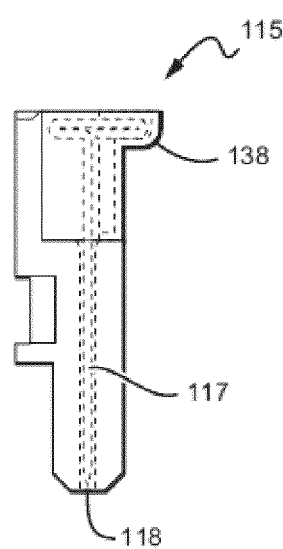
FIG. 7 is a side view of the lancet cartridge of FIG. 5.

FIGS. 5-7 show different views of a lancet cartridge 115. Cartridge 115 holds a plurality of lancets 117. A slot 116 is disposed on a side of cartridge 115, so that a hammer 186 (see FIGS. 11-14) of a lancing device within device 100 can contact one of the plurality of lancets 117, thus causing the lancet to partially exit cartridge 115 via slot 118. The lancet is retracted by return slider 690 of device 100 (see FIG. 4). Cartridge 115 also has a molded bump 138 that provides friction to the plurality of lancets 117 and helps to maintain each lancet stationary when not being fired.

Cartridge 115 can include any appropriate number of lancets, preferably between 15 and 25 lancets, more preferably between 18 and 22 lancets, and most preferably 20 lancets. The lancets are preferably sterilized and sealed prior to use.

Figure 8:
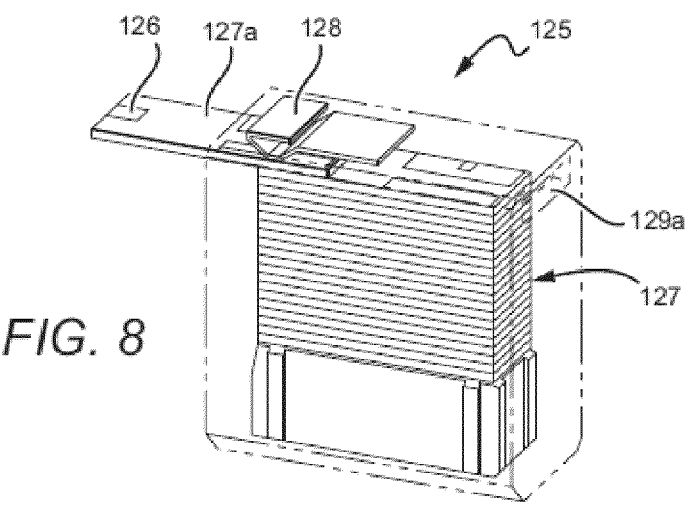
FIG. 8 is a perspective view of one embodiment of an analyte sensor cartridge.
Figure 9:
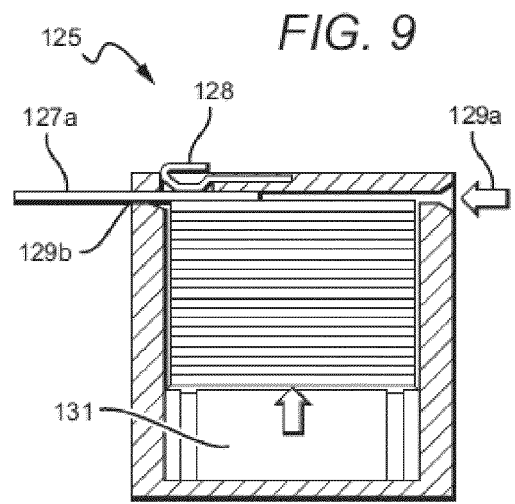
FIG. 9 is a side view of the analyte sensor cartridge of FIG. 8.

FIGS. 8 and 9 show different views of a analyte sensor cartridge 125. Cartridge 125 holds a plurality of test units 127 (e.g., test strips). Cartridge 125 has electrical contacts 128 for communicatively coupling the analyte sensors to the conversion electronics 137. Alternatively, contacts 128 could be eliminated and electronics 137 could directly interface with contacts 129 of test unit 127 (see FIG. 10) via an open aperture in cartridge 125. Cartridge 125 also has a slot 129a that couples with a test unit lateral ejection mechanism of device 100. When actuator 140 is cocked, the advance mechanism enters slot 129a and pushes a portion of test unit 127a out of slot 129b, thus exposing analyte sensor 126 for use.

Cartridge 125 can include any appropriate number of test strips, preferably between 15 and 25 test strips, more preferably between 18 and 22 test strips, and most preferably 20 test strips.

Cartridge 125 preferably includes test strips configured to test for different analytes. For example, some test strips may test for glucose while other test strips test for fructosamine. Furthermore, cartridge 125 can have at least one test strip capable of testing for two analytes simultaneously, either by including two analyte-binding chemicals/reactants within one absorbing material or by including two different analyte sensors on one test strip. In addition, cartridge 125 preferably includes at least one calibration test strip for verifying the calibration of conversion electronics 137. In one embodiment, the calibration test strip is an analyte sensor that has a known amount of glucose.

Cartridge 125 also has a spring-load base 131 configured to push the plurality of test strips 127 upward, thus repositioning a new test strip into place after test strip 127a is removed from cartridge 125.

Figure 10:
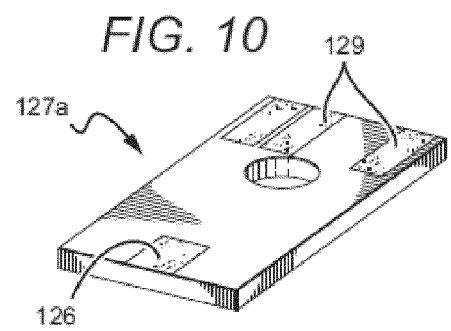
FIG. 10 is a perspective view of one embodiment of a test unit that has an analyte sensor.

FIG. 10 shows a test unit 127a having an analyte sensor 126. Analyte sensors are well known and generally comprise an absorbent material with an analyte-binding reactant. While test unit 127a is configured as a test "strip", those of skill in the art will appreciate that other shapes and configurations (e.g., capsules, disks) can be used consistently with the inventive subject matter. Analyte sensor 126 is configured to generate a signal that is sent to electrical contacts 129. Electrical contacts 129 are communicatively coupled with electrical contacts 128 of cartridge 125 and allows the signal generated by analyte sensor 126 to reach the conversion electronics 137 for analysis. Alternatively, electrical contacts 129 could directly interface with conversion electronics 137 via an open aperture on cartridge 125.

Figure 11:
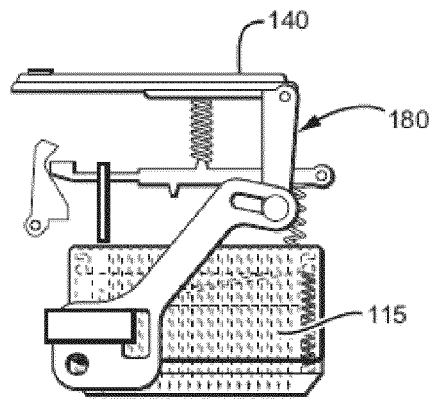
FIG. 11 shows one embodiment of a linkage mechanism of the device of FIG. 1 engaged with the lancet cartridge of FIG. 5. The linkage mechanism is shown at four different stages of use: (i) rest position; (ii) lever pulled; (iii) lever released (cocked and ready); and (iv) button pressed to project hammer.
Figure 11:
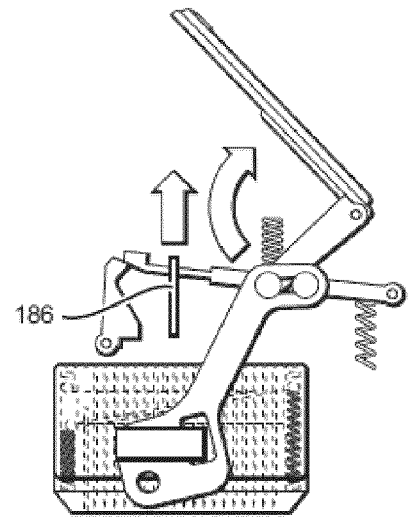
Figure 11:
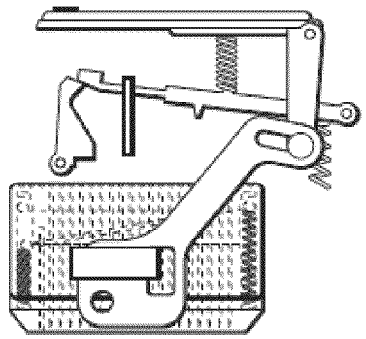
Figure 11:
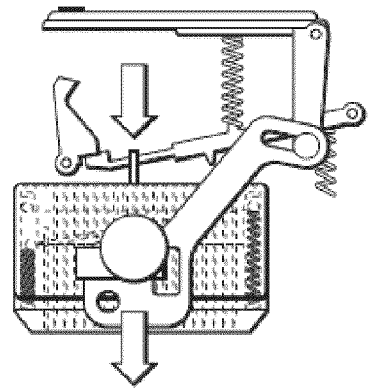

FIG. 11 shows a linkage mechanism 180 of device 100 coupled with lancet cartridge 115. FIG. 11 provides a summary of the four progressive stages for using linkage 180 and lancet cartridge 115 as a lancing device: (i) initial resting position; (ii) cocking of actuator 140; (iii) cocked and ready position; and (iv) releasing and projecting a lancet. At the final stage, a finger or other body part can be placed over hole 113 in order to prick the body part and draw a blood sample. These four stages will now be explained in more detail.

Figure 12:
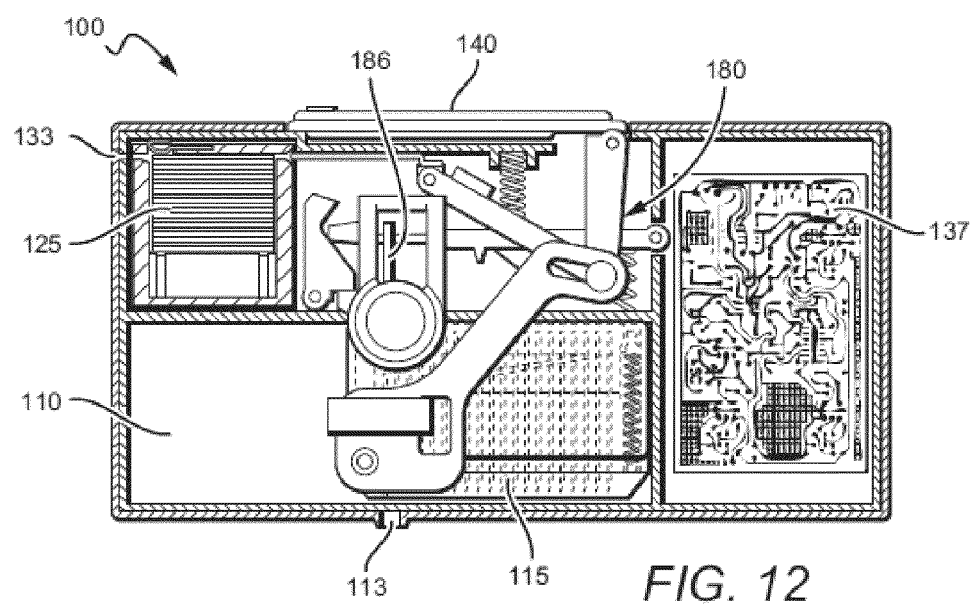
FIG. 12 is a side view of the device of FIG. 1, showing the inner components of the device in a rest position.

FIG. 12 is a side view of device 100 showing various internal components of device 100, such as: electronics 137, linkage mechanism 180, cartridge 115, and cartridge 125. FIG. 12 shows device 100 at a resting position (i.e., before actuator 140 has been cocked). Hammer 186 is in an un-cocked position.

Figure 13:
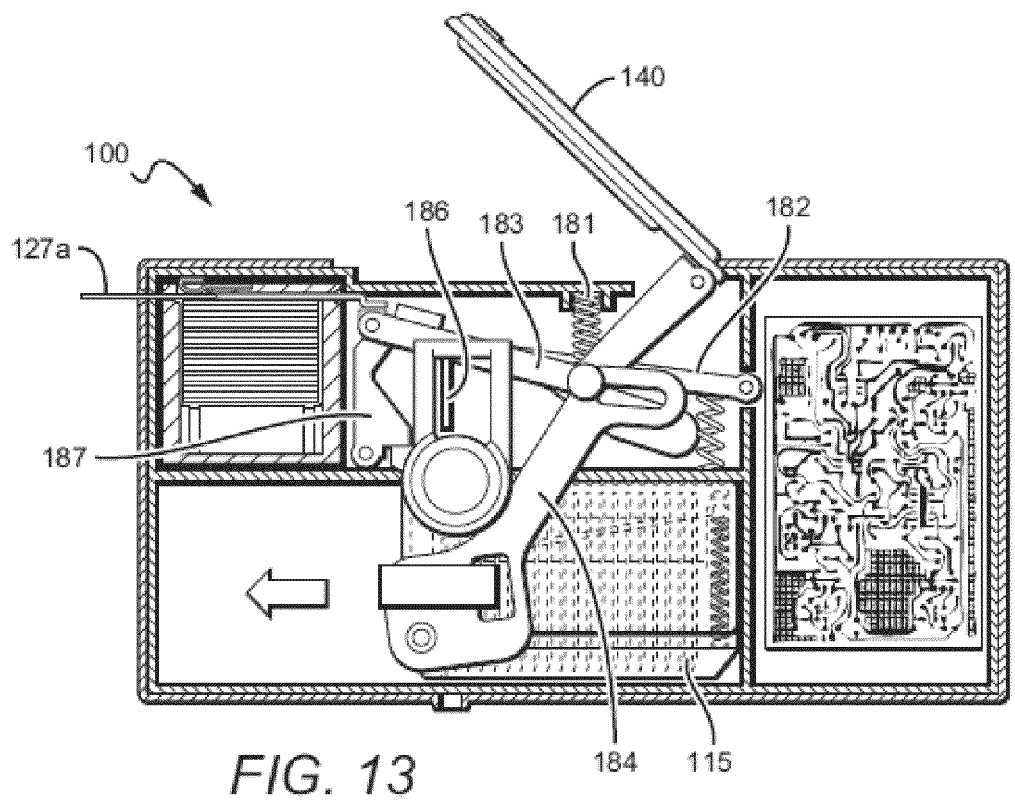
FIG. 13 is a side view of the device of FIG. 1, showing the inner components of the device as a lever is being pulled.

FIG. 13 shows the internal components of device 100 as actuator 140 is being cocked. The cocking of actuator 140 has caused link 182 to raise up and compress spring 181. At the same time, hammer 186 has been raised via link 183. In addition, the left end of link 182 has been raised over the top of link 187 such that link 182 is maintained in an inclined position and spring 181 is maintained in a compressed position (i.e., hammer 186 has been "cocked" or "readied"). At the same time, link 183 is driven to the left, pushing test strip 127a out of slot 133 (see FIG. 1). In addition, link 184 has been advanced to the left, causing cartridge 115 to advance left and into position. In disclosed embodiments, link 183 couples with cartridge 115 such that when cartridge 115 has been completely advanced to the left, link 183 allows the last lancet of cartridge 115 to remain in a usable (i.e., projectable) position. For example, link 183 could release (e.g., de-couple) from cartridge 115 during subsequent cocking of actuator 140. In this manner, linkage mechanism 180 allows a lancet to be available for use, even after cartridge 115 has been advanced through each of the plurality of lancets 117.

In this manner, actuator 140 and linkage mechanism 180 are configured to (i) cock a lancing device (e.g., lift hammer 186, link 182, and spring 181) (ii) partially expose an analyte sensor on a test unit; and (iii) advance a lancet cartridge into position, all in a single motion (e.g., pulling up actuator 140). It is also contemplated that an analyte testing device could have a linkage mechanism that is configured to accomplish the three steps above using two or more motions (e.g., pulling a lever, then pushing a lever).

Figure 14:
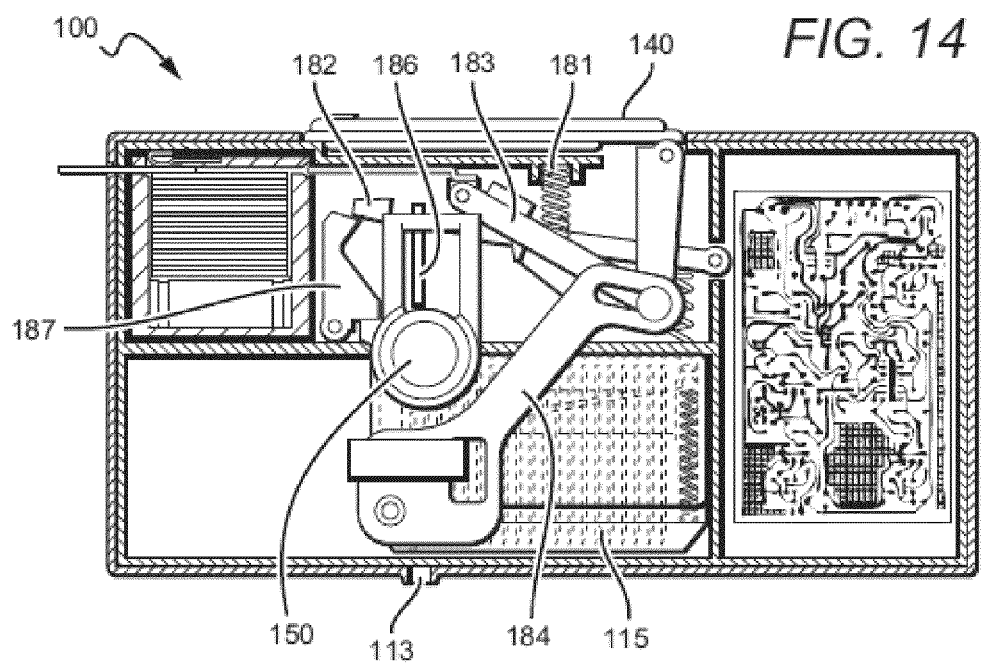
FIG. 14 is a side view of the device of FIG. 1, showing the inner compartments of the device after a lever has been pulled and a hammer has been spring-loaded.

FIG. 14 shows the position of linkage 180 after actuator 140 has been cocked. Once actuator 140 has been cocked, button 150 can be pressed to release link 187 from under link 182, thus causing spring 181 to push link 182 and hammer 186 downward to project a lancet from cartridge 115.

One of skill in the art will appreciate that configurations of linkage mechanism 180 other than that shown in the drawings can be used consistently with the inventive subject matter taught herein. In some alternative embodiments, linkage mechanism 180 is controlled and/or actuated by electrical drivers rather than pure mechanical means. For example, pulling actuator 140 could send an electrical signal to conversion electronics 137, which then operates a motor, or multiple motors, in order to perform any combination of: (i) cocking a lancing device, (ii) partially exposing a test strip for use, and (iii) advancing a lancet cartridge into position. In yet other embodiments, the lancing system is designed such that a cocking step is not required.

Figure 15:
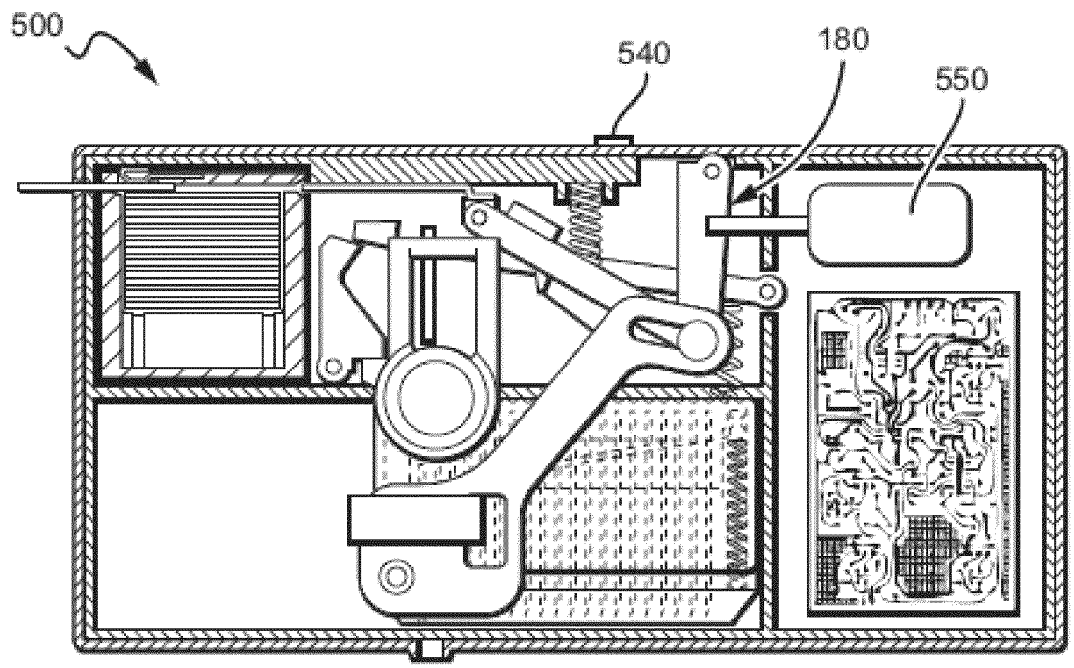
FIG. 15 is a side view of an analyte device with a motor.

FIG. 15 shows an analyte testing device 500 that has an actuator 540 and a motor 550. Actuator 540 comprises a button that sends a signal to motor 550. Motor 550 operates to drive linkage mechanism 180 upon receiving a signal. Motor 550 and actuator 540 is one embodiment of an analyte testing device that is not purely mechanism.

Figure 16:
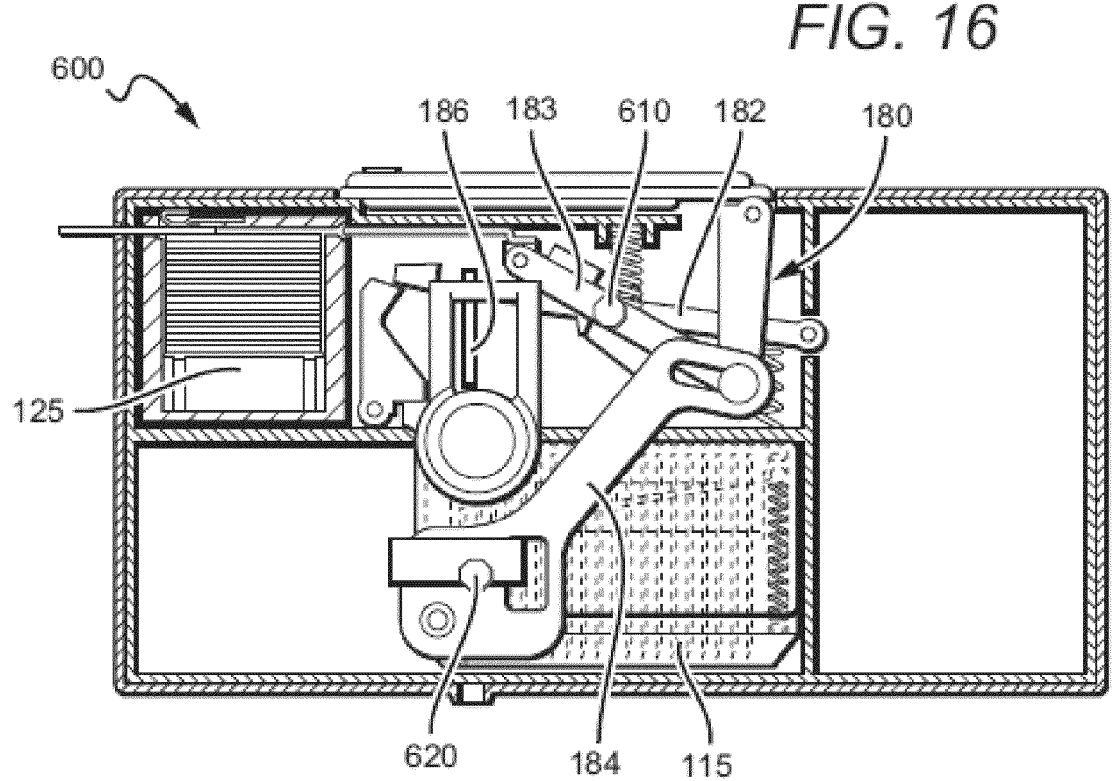
FIG. 16 is a side of an analyte device with a first and second disengagement control.

FIG. 16 shows an analyte testing device 600 that has a first disengagement control 610 and a second disengagement control 620. Control 610 operates to disengage link 182 from link 183, thus disengaging cartridge 125 from linkage mechanism 180. Control 620 operates to disengage link 184 from cartridge 115. In this manner, cartridges 115 and 125 can be disengaged from linkage mechanism 180, and thus can be used independently of one another.

Figure 17A:
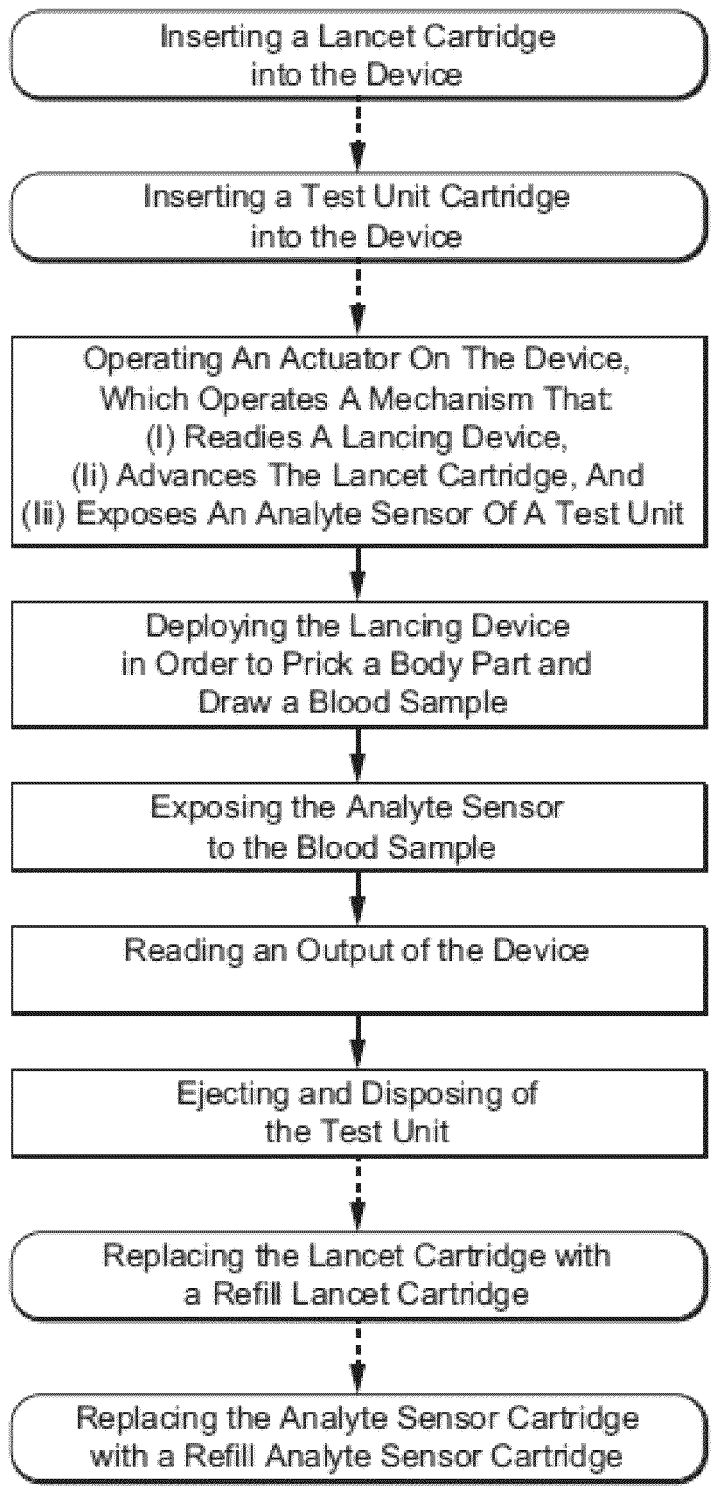
FIG. 17a is a schematic of one embodiment of a method of using the device of FIG. 1.

FIG. 17a shows a method of using device 100, comprising: inserting a lancet cartridge into the device; inserting a test strip cartridge into the device; operating an actuator on the device, which operates a mechanism that (i) readies a lancing device, (ii) advances the lancet cartridge, and (iii) exposes an analyte sensor of a test unit; deploying the lancing device in order to prick a body part and draw a blood sample; and exposing the analyte sensor to the blood sample. The method of FIG. 15 can optionally include the steps of: reading an output of the device; ejecting and disposing of the test unit;

replacing the lancet cartridge with a refill lancet cartridge; and replacing the analyte sensor cartridge with a refill analyte sensor cartridge.

The first two and last two steps are displayed in round boxes and with dotted lines to indicate that these steps need not be repeated at every cycle of usage of the device. For example, in embodiments having twenty lancets and test strips per cartridge, the steps of inserting/removing cartridges need only be performed every twentieth cycle of use.

Figure 17B:
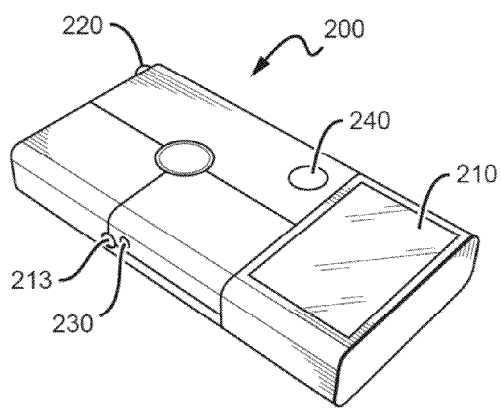
FIG. 17b is a perspective view of one embodiment of an analyte testing device having an LCD touch-screen display.

FIG. 17b shows an analyte testing device 200 having an LCD touch screen display 210. Display 210 can be used to display test results, supplies used/remaining, calories burned, time/date, history of drugs administered, journal entries, or any other number of data useful for monitoring analytes. Display 210 can also be used to type and input data into device 100.

Device 200 also has a first work light 220 positioned to illuminate a test strip that has been partially pushed out from device 200, and a second work light 230 positioned to illuminate a lancet hole 213. First and second work lights 220 and 230 are useful for using device 200 in poor lighting conditions.

Conversion electronics within device 200 additionally includes a Personal Emergency Response System (PERS), including a PERS button 240. Button 240 is configured to (i) contact a third party, (ii) identify the user of device 200, and (iii) provide a user's health data to the third-party. Examples of third parties can include spouse, relative, friend, home nurse, doctor, health care worker, ambulance operator, police operator, or any other person that can provide health care assistance. The Personal Emergency Response System is also preferably configured to automatically contact a third party as a function of the user's health data. For example, when the user is a diabetic patient, PERS can be configured to contact a third party when the user's glucose test results are below a predetermined threshold. PERS can also be configured to notify the third party of an urgency level (e.g., low, moderate, high, critical, etc), and can determine who to contact based on the urgency level.

Figure 17D:
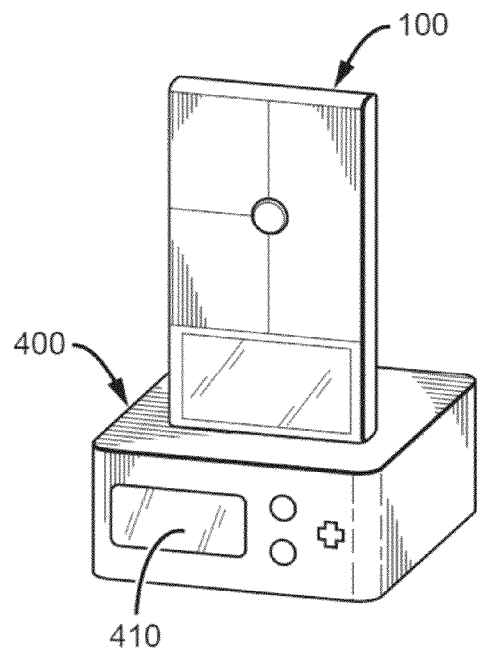
FIG. 17d is a perspective view of one embodiment of a docking station coupled with the device of FIG. 1.
Figure 17C:
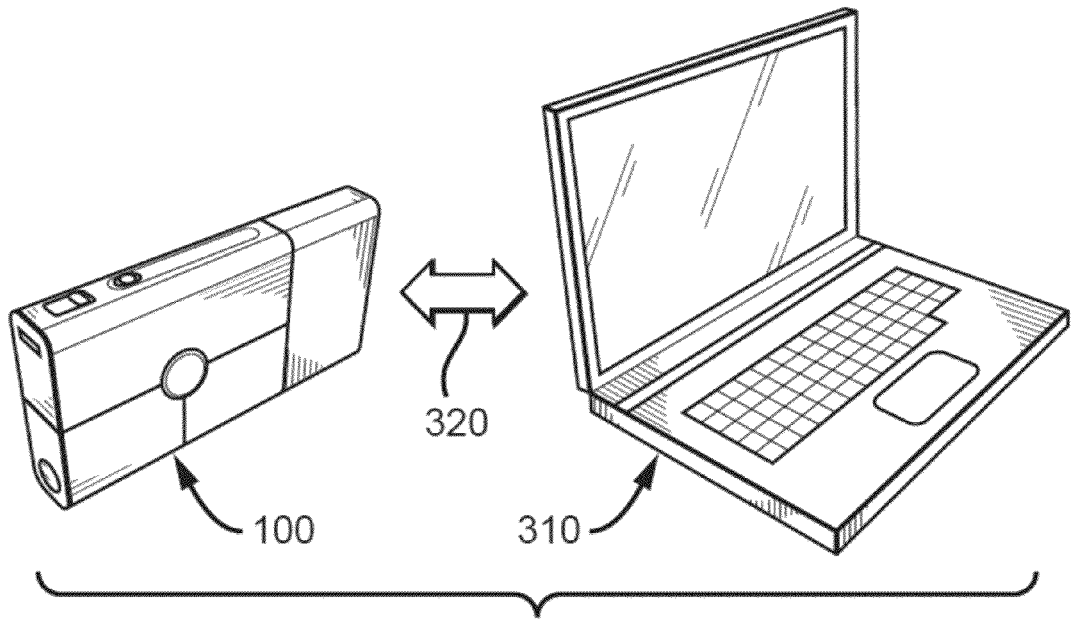
FIG. 17c is perspective view of the device of FIG. 1 transmitting wireless communications to a laptop.

FIG. 17c shows device 100 communicatively coupled to a laptop 310 via a wireless connection 320. Numerous wireless protocols can be used, for example Bluetooth, WiFi, 802.11, cellular, or any other protocol suitable for wireless communication. Connection 320 can be used to back up data, transmit data to a health care provider's server via the internet, reorder supplies, receive notifications from a doctor, or receive data analysis reports from an analytics software running on the laptop. It is also contemplated that connection 320 can be a wired connection. Furthermore, it is contemplated that device 100 can connect to devices other than laptop 310, for example a home computer, a smart phone, a server, or any other computing device suitable for storing, analyzing, and/or exchanging data.

FIG. 17d shows device 100 coupled with a docking station 400. Docking station 400 is configured to provide power and data connectivity to device 100. For example, station 400 can be configured to charge a re-chargeable battery within device 100. Station 400 can also be configured to back up data on device 100 and transmit data to another device, such as a home computer or a medical provider server. Docking station 400 also has a visual interface 410, through which a user can view and/or input data.

FIG. 17e shows an analyte testing device 520, with a test strip 127a and a test strip ejector 560. FIG. 17f is a side view cut-out of device 520, showing how ejector 560 operates to completely eject test strip 127a for disposal after usage. Ejector 560 advantageously obviates the need for direct hand contact with a used test strip. Ejector 560 has a plunger 561 configured to engage an aperture 529 of test strip 127a, thus preventing test strip 127a from being accidentally re-inserted back into cartridge 525 when a user applies finger pressure to the test strip 127 for blood application.

FIGS. 17g and 17h show an alternate analyte testing device 671. Unlike device 100, device 671 has a wheel 670 for adjusting a lancet penetration depth. A lancet within lancet cartridge 715 exits device 671 via hole 613 according to an adjustable depth determined by the setting of wheel 670. Device 671 also has a window 675 for indicating the current lancet penetration depth setting. Spring-loaded return slider 690 is configured to retract the lancet back into cartridge 715.

In another embodiment of the disclosed technology, an analyte testing device can include a plurality of analyte sensors (e.g., housed in an analyte sensor cartridge) and a plurality of lancets (e.g., housed in a lancet cartridge), in which a one-handed operation of an actuator mechanism can be implemented to ready the device for a test, prick the user to extract blood to be analyzed in the test, and reset the device for another use. For example, the actuator mechanism can be implemented to ready the device for a test by moving an analyte sensor (e.g., a test strip) forward to expose the sensor and advancing a firing component to a position for projection of a lancet. The actuator mechanism can subsequently be implemented to project (or fire) the lancet to prick a user to draw blood for analysis in the test. The actuator mechanism can be implemented to reset the device by ejecting the test strip and returning the components of the actuator mechanism to an initial position.

Figure 18A:
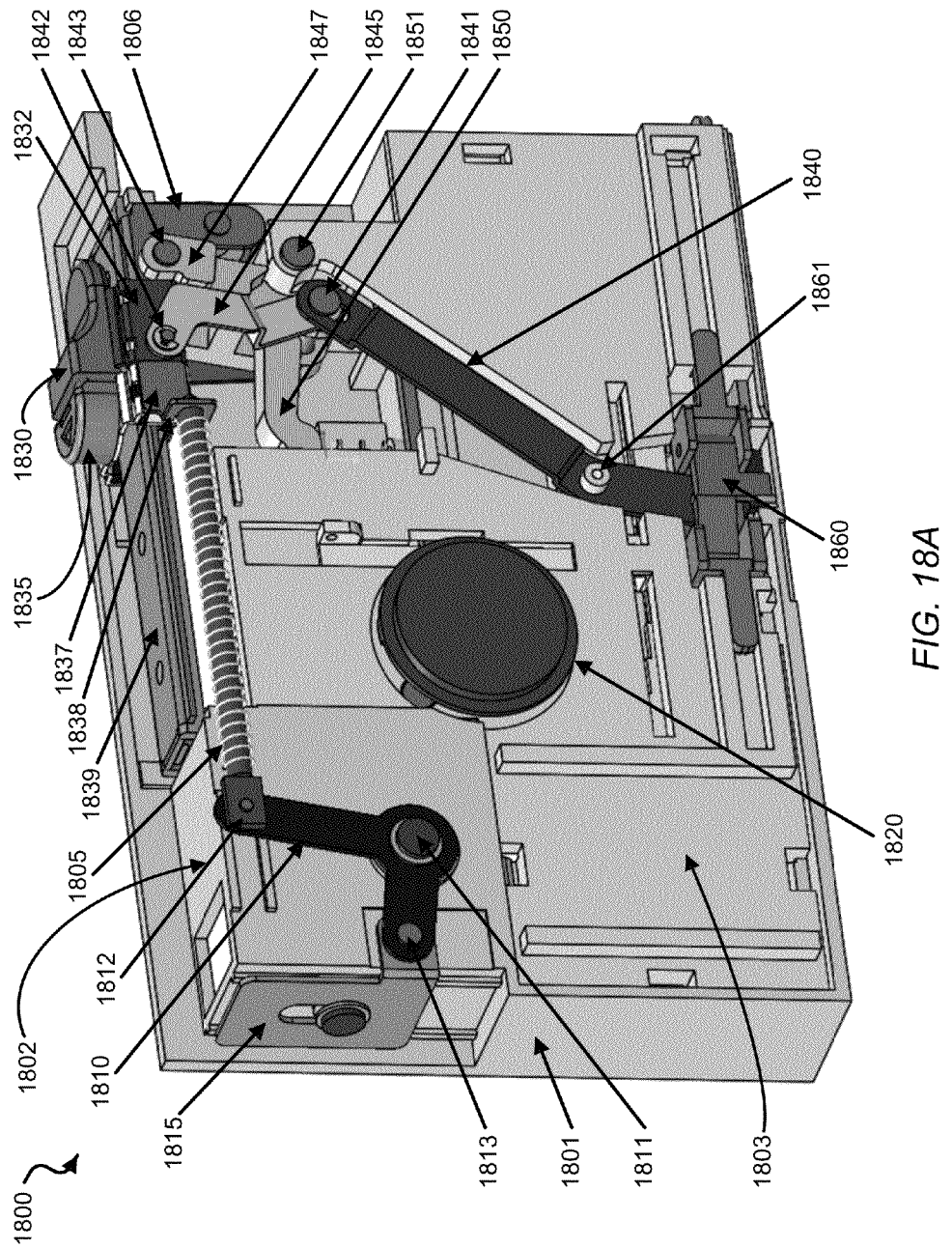
FIGS. 18A-18E show schematics of one embodiment of an exemplary actuator mechanism of an analyte testing device.
Figure 18B:
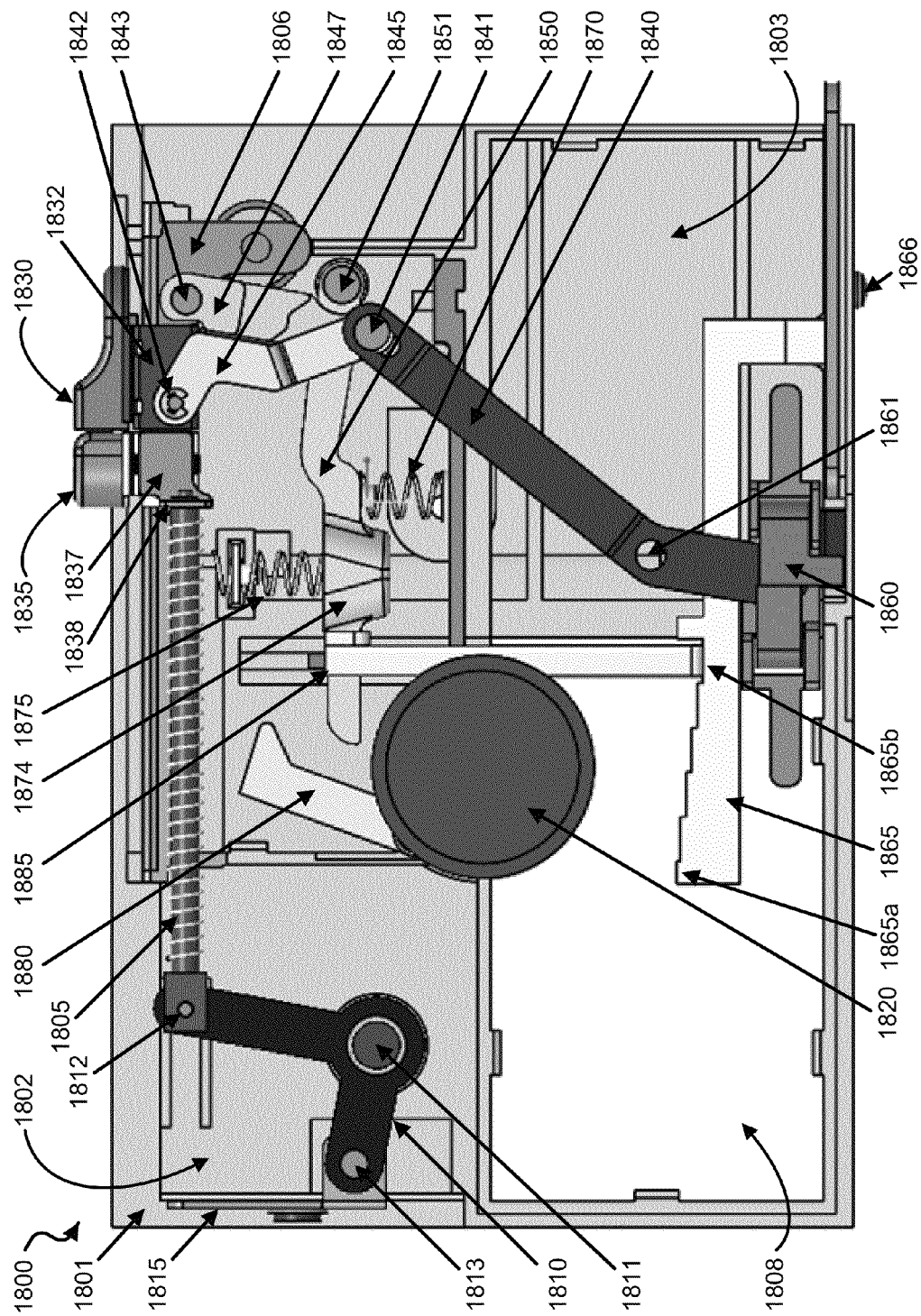

FIGS. 18A and 18B show an example of an analyte testing device 1800 that includes one exemplary implementation of the above actuator mechanism. FIG. 18A shows a three dimensional cross sectional view of the components that make up the actuator mechanism. FIG. 18B shows a two dimensional cross sectional view of the components that make up the actuator mechanism. It is noted that some components included in the analyte testing device 1800 may not necessarily be shown in the schematic of FIGS. 18A and 18B.

As shown in FIGS. 18A and 18B, the actuator mechanism is encased in a containment structure 1801, also referred to as a chassis or an internal housing structure. The containment structure 1801 can be encased within an external housing or device casing. The containment structure 1801 can be used to provide positioning and/or structural support to various modules and components contained within the chassis of the analyte testing device 1800. The device 1800 includes an analyte sensor cartridge 1802 and a lancet cartridge 1803, in which the analyte sensor cartridge 1802 and the lancet cartridge 1803 are contained within separate cavities located within the chassis 1801. The schematics of FIGS. 18A and 18B, as well as other subsequent figures, show the cavities of the chassis 1801 where the analyte sensor cartridge 1802 and the lancet cartridge 1803 are located.

The actuator mechanism includes a sliding button that includes a cocking button 1830 and an eject button 1835 that move translationally along a sliding track 1839 formed on the top facet of the device 1800. For example, implementing the sliding button results in (1) moving a new test strip from a position within the analyte sensor cartridge 1802 to a position that exposes a portion of the test strip (e.g., such as the site on the test strip to receive the testing sample) outside of the containment structure 1801 and (2) advancing a firing component to a readied position for projection of a lancet from the lancet cartridge 1803 (e.g., a firing position). Also, for example, implementing the sliding button can result in (3) advancing the lancet cartridge 1803 within the analyte testing device 1800 to a position in which the lancet is positioned in a firing path of the firing component for projection. The sliding button can be implemented by pushing the cocking button 1830 from an initial position forward to a cocked position in a sliding motion along the track 1839, as shown later in FIGS. 19A and 19B. In the described embodiment, sliding the cocking button 1830 forward includes sliding the eject button 1835 forward to the cocked position as well, e.g., as the forward motion of the cocking button 1830 pushes forward the eject button 1835. The cocking button 1830 includes a button pad where a user can make contact to engage the sliding button, e.g., to ready the device. The cocking button 1830 includes a sliding base component 1832 that facilitates the sliding of the cocking button 1830 on the sliding track 1839 and links the cocking button 1830 to other components of the actuator mechanism. The eject button 1835 includes an eject button pad where a user can make contact to engage the eject button 1835 of the sliding button, e.g., to eject a used test strip from the device. The eject button 1835 includes an eject base component 1837 that facilitates the sliding of the eject button 1835 on the sliding track 1839 and links the eject button 1835 to other components of the actuator mechanism. After the sliding button reaches the cocked position, the cocking button 1830 can be brought back to the initial position by a linear spring coupled between the cocking button 1830 and a cocking base component 1806 of the actuator mechanism. For example, this return of the cocking button 1830 from the cocked position to the initial position can thus be implemented automatically, without a user intervention to manually return the cocking button to the initial position. In some examples, sliding the cocking button 1830 forward from the initial position to the cocked position can include producing a clicking sound when the cocking button arrives in the cocked position.

The actuator mechanism includes, underneath the sliding track 1839, a spring-loaded arm component 1805 that is utilized in the movement of the new test strip from within the analyte sensor cartridge 1802 to expose the test strip outside of the containment structure 1801 of the device 1800 via an opening slot covered by a sliding door 1815 of the actuator mechanism that conceals the slot opening of the analyte sensor cartridge 1802 when a test is not performed for blocking moisture and contaminants from getting into contact with and polluting test strips stored inside the device 1800. A door crank component 1810 is provided to open or close the sliding door 1815 under operation of the actuator mechanism.

The spring-loaded arm component 1805 is configured between the eject base component 1837 of the sliding button and a door crank component 1810 of the actuator mechanism. The door crank component 1810 is configured between the spring-loaded arm component 1805 and the door 1815 of the actuator mechanism. The spring-loaded arm component 1805 includes a rod shaft that is configured with a spring surrounding the exterior of the rod shaft. The rod shaft is connected to the eject base component 1837 via a push link component 1838. In some examples, the push link component 1838 can be configured as a portion or facet of the eject base component 1837. For example, the end of the rod shaft can rest within an opening of the push link component 1838 such that the external spring is in an initial compression state (e.g., which can be partially compressed or substantially uncompressed) when the sliding button is in the initial position. For example, when the cocking button 1830 of the sliding button (along with the eject button 1835) moves forward along the track 1839 from the initial position to the cocked position, the spring of the spring-loaded arm component 1805 compresses against the push link component 1838 from its the initial compression state to an intermediate compression state, as a portion of the rod shaft of the spring-loaded arm component 1805 passes through the opening of the push link component 1838. Also, for example, when the eject button 1835 of the sliding button moves forward along the track 1839, the spring of the spring-loaded arm component 1805 further compresses against the push link component 1838, as the rod shaft of the spring-loaded arm component 1805 passes further through the opening of the push link component 1838 while the eject button 1835 advances along the remaining travel distance of the sliding track 1839 until it reaches a final position (e.g., eject position). For example, the actuator mechanism can be configured to not set the eject button 1835 at the eject position upon its arrival, in which the spring of the spring-loaded arm component 1805 can uncompress to drive the eject button 1835 back to the initial position. Thus, the return of the eject button 1835 from the final position to the initial position can be implemented automatically, without a user intervention to manually return the eject button to the initial position.

The door crank component 1810 is structured in a (substantially) L-shaped form having two arms at a fixed angle (e.g., which can be substantially perpendicular) and meeting at a joint 1811. The door crank component 1810 is configured between the spring-loaded arm component 1805 and the sliding door 1815 of the actuator mechanism that conceals the slot opening of the analyte sensor cartridge 1802. The door crank component 1810 is connected to the spring-loaded arm component 1805 at a joint 1812 and connected to the door 1815 at a joint 1813. The movement of the sliding button from the initial position to the cocked position drives the spring-loaded arm component 1805 forward. The forward motion of the spring-loaded arm component 1805 to the cocked position results in a rotational motion of the door crank component 1810 about the joint 1811, in which the door crank component 1810 moves the door 1815 from a closed position covering the slot opening of the analyte sensor cartridge 1802 to an opened position, e.g., such that a test strip can advance out of the slot opening to expose the sample-receiving portion of the strip. For example, one arm of the door crank component 1810 is moved forward by the translational advancement (e.g., pushing) of the spring-loaded arm component 1805, which causes the rotation the door crank component 1810 about the joint 1811. The rotation results in the other arm of the door crank component 1810 moving the door 1815 in a translational motion (e.g., pulling) to expose the slot opening.

In the initial position, the door 1815 completely covers the slot opening of the analyte sensor when a test strip is not in use. For example, moisture and other contaminants or particulates can contaminate the stored unused test strips if permitted to enter, e.g., and damage chemical reagents on the test strips, which can cause inaccurate analyte testing results. The door 1815 prevents sunlight, moisture and particulates in the air from entering the analyte sensor cartridge 1802. The door 1815 also helps to maintain a constant ambient temperature within the analyte sensor cartridge 1802, e.g., by providing a seal over the slot opening that prevents heat from diffusing in or out of the analyte sensor cartridge 1802.

The analyte sensor cartridge 1802 can include, in some implementations, a temperature sensor that is in communication with an electronic processing unit within the device 1800, e.g., such as the conversion electronics 137 previously described and shown in FIG. 12. The conversion electronics 137 can be configured to continuously monitor temperature data provided by the temperature sensor and provide reports and alarms to a user on a display of the device. In some implementations, the temperature sensor can be configured within the cavity encased by the chassis 1801 of the analyte sensor module configured to hold the analyte sensor cartridge 1802. For example, the temperature sensor can be configured to continuously or continually sense the ambient temperature in the analyte sensor module, e.g., in which the ambient temperature at a given instance in time or the ambient temperature over a duration of time can be sensed and recorded as data (e.g., by the processing unit). For example, the processing unit can determine if the temperature is within or outside of a suitable range (e.g., high or low) of the analytes. The analyte testing device 1800 can be in wired or wireless communication with a mobile device or a computing device that includes a web portal featuring a user interface that the user of the device 1800 can use for various functions, including monitoring the status of the device 1800 such as the temperature data in the analyte sensor cartridge 1802. Some examples for wireless communications of the device 1800 include 3G wireless communication standards, 4G wireless communication standards including, LTE, WiFi, Bluetooth, and other suitable wireless communications via radio frequency waves and other electromagnetic waves.

The actuator mechanism includes a lancet advance component 1840 that is utilized to a ready a lancet for projection from the lancet cartridge 1803 (e.g., advance lancet firing components to a firing position). One end of the lancet advance component 1840 is coupled to the sliding base component 1832 of the cocking button 1830 via a lancet cocking link 1845 of the actuator mechanism. The lancet advance component 1840 is connected to the lancet cocking link 1845 at a joint 1841. The lancet cocking link 1845 is connected to the sliding base component 1832 at a joint 1842. The lancet advance component 1840 is also coupled to the cocking base component 1806 via a lancet cocking crank 1847 of the actuator mechanism. The lancet advance component 1840 is connected to the lancet cocking crank 1847 at the joint 1841. The lancet cocking crank 1847 is connected to the cocking base component 1806 at the joint 1843. The other end of the lancet advance component 1840 is coupled to a lancet slider component 1860 of the actuator mechanism and can move the lancet slider component 1860 translationally, e.g., via the movement of the cocking button 1830. The lancet advance component 1840 can be structured to have two arms (e.g., a long arm and a short arm) that meet at a point (e.g., at a fixed angle) that can rotate about a joint 1861. The exemplary long arm of the lancet advance component 1840 is connected to the lancet cocking link 1845 at the joint 1841, and the exemplary short arm of the lancet advance component 1840 is coupled to the lancet slider component 1860.

The actuator mechanism includes a lancet fire arm component 1850 that is also utilized to a ready a lancet for projection from the lancet cartridge 1803 (e.g., advance lancet firing components to a firing position). One end of the lancet fire arm component 1850 is coupled to the chassis 1801 at a joint 1851 to rotate about the joint 1851 at a fixed point. As shown in FIG. 18B, the other end of the lancet fire arm component 1850 is configured with a curved geometry, e.g., capable of sliding along another surface with a reduced friction. In the initial position, the lancet fire arm component 1850 can rest between two springs: a return spring 1870 that is positioned underneath the lancet fire arm component 1850 and that can be fixed to a structure of the chassis, and a firing spring 1875 that is positioned above the lancet fire arm component 1850 and that can be fixed to a structure of the chassis near the spring-loaded arm component 1805. In the described embodiment, the lancet fire arm component 1850 can include a weight 1874 configured on the lancet fire arm component 1850 directly underneath the firing spring 1875, e.g., such that the firing spring contacts the weight 1874. In the initial position, the return spring 1870 and the firing spring 1875 are in an initial compression state (e.g., which can be partially compressed or substantially uncompressed). The lancet fire arm component 1850 is coupled to a firing hammer component 1885 of the actuator mechanism through an opening in the top end of the firing hammer component 1885, e.g., in which motion of the lancet fire arm component 1850 can push the firing hammer component 1885 in a linear direction to the firing position. For example, as the lancet fire arm component 1850 pushes the firing hammer component 1885 to the firing position, the curved end of the lancet fire arm component 1850 also contacts and moves about a trigger catch component 1880 of the actuator mechanism until the curved end has been raised above and is seated upon the top surface of the trigger catch component 1880, as shown later in FIG. 19B. In other examples, the lancet fire arm component 1850 can be coupled to the firing hammer component 1885 by a joint that allows the lancet fire arm component 1850 to pull and push the firing hammer component 1885 in the linear direction. As described later in the patent document, a lancet can be fired from the device by depressing a firing button 1820 of the actuator mechanism located on an external side of the device 1800, in which the firing button 1820 retracts the trigger catch component 1880 to release the lancet fire arm component 1850, such that the firing spring 1875 (and the weight 1874) drives the lancet fire arm component 1850 downward to drive the firing hammer component 1885 downward to push a lancet to project out of the device 1800.

Figure 18C:
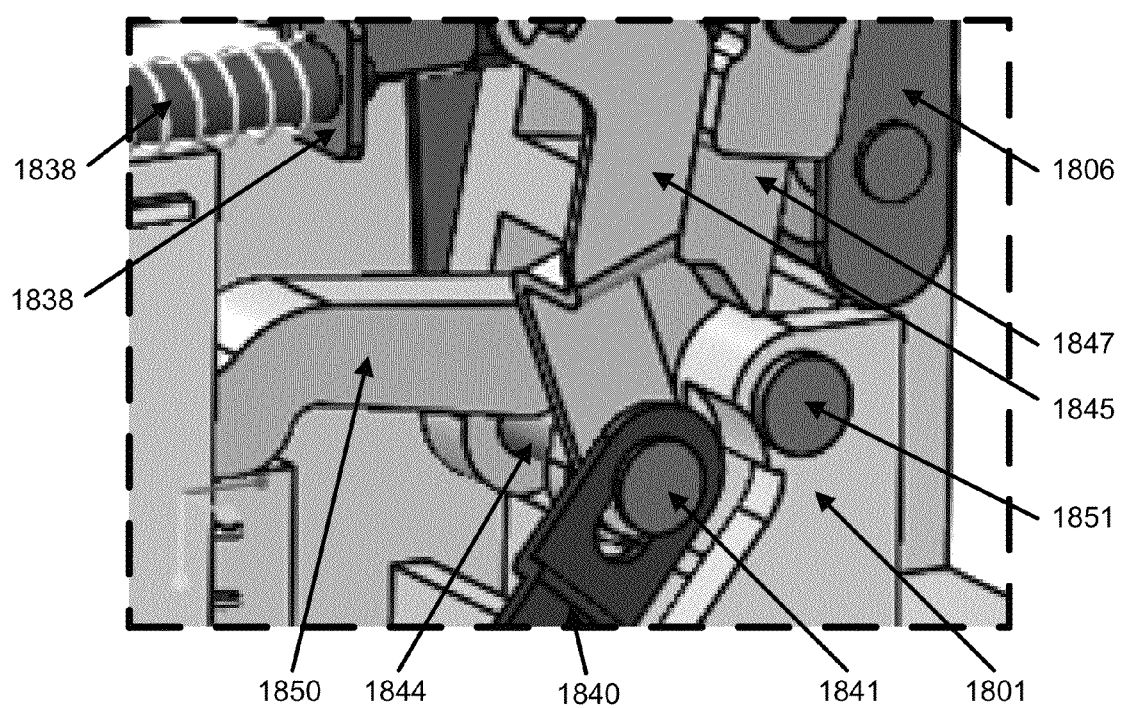

The movement of the sliding button from the initial position to the cocked position advances the lancet advance component 1840 forward, e.g., by pulling of the lancet cocking link 1845 forward, which pulls the lancet advance component 1840 forward. The forward motion of the lancet advance component 1840 to the cocked position includes a rotation of the lancet advance component 1840 with respect to the lancet cocking link 1845 about the joint 1841. The forward motion of the lancet advance component 1840 to the cocked position also includes a rotation of the lancet advance component 1840 with respect to the lancet cocking crank 1847 about the joint 1841. The forward motion of the lancet advance component 1840 to the cocked position results in motion of the lancet fire arm component 1850, which can drive the firing hammer component 1885 to the firing position. For example, the movement of the lancet fire arm component 1850 is actuated by the movement of the long arm of the lancet advance component 1840 and/or the lancet cocking link 1845. As shown in FIG. 18C, which shows an enlarged cut-out portion of the schematic of FIG. 18A, the actuator mechanism can include a roller pin structure 1844 that is connected to the lancet advance component 1840 and/or the lancet cocking link 1845. The roller pin structure 1844 is configured directly beneath the lancet fire arm component 1850 to slide or roll on the underside of the lancet fire arm component 1850 to drive the movement of the lancet fire arm component 1850 upwards. The upwards movement of the lancet fire arm component 1850 pushes the firing hammer component 1885 to the firing position and is seated upon the top surface of the trigger catch component 1880.

For example, referring to FIG. 18B, when the cocking button 1830 of the sliding button (along with the eject button 1835) moves forward along the track 1839 from the initial position to the cocked position, the long arm of the lancet advance component 1840 is moved by the lancet cocking link 1845 such that the lancet advance component 1840 rotates about the joint 1861, in which the short arm of the lancet advance component 1840 moves the sliding component 1860 in a linear direction. The movement of the sliding component

Figure 18D:
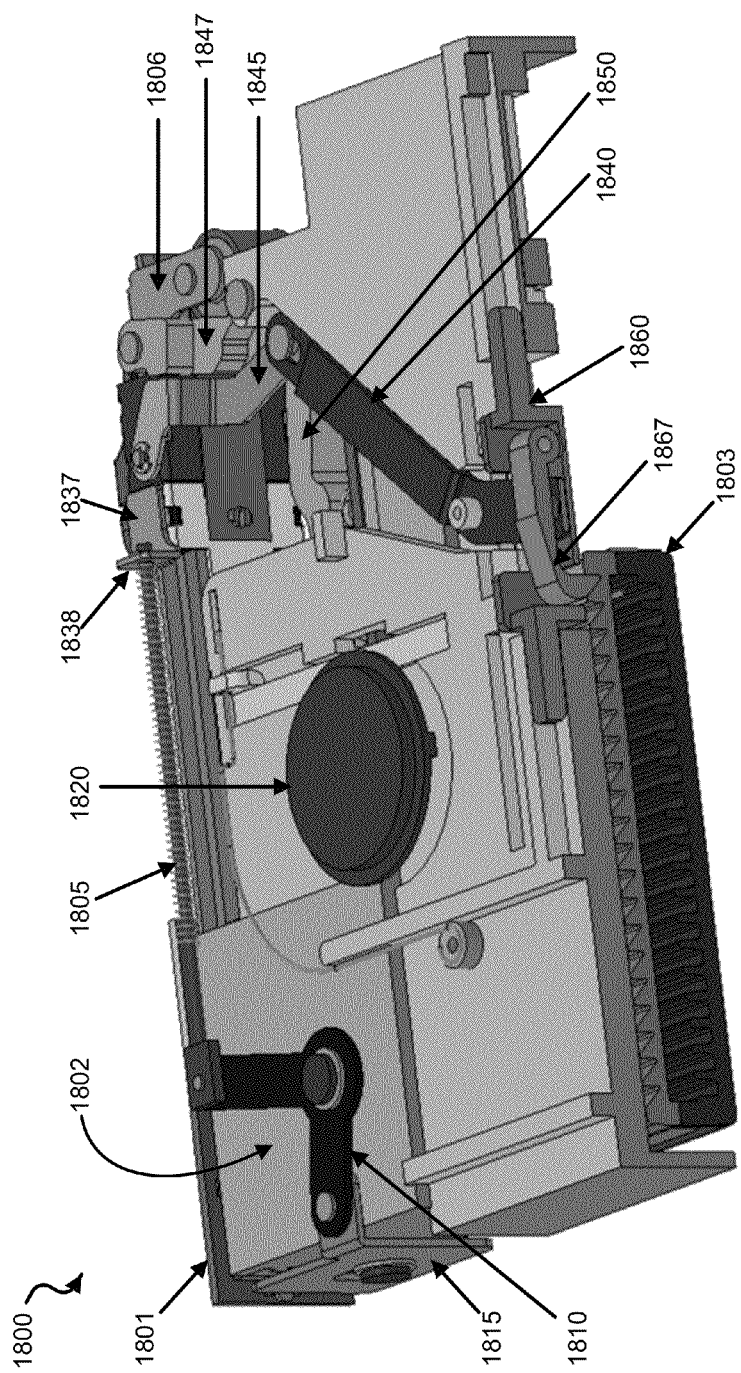
Figure 18E:
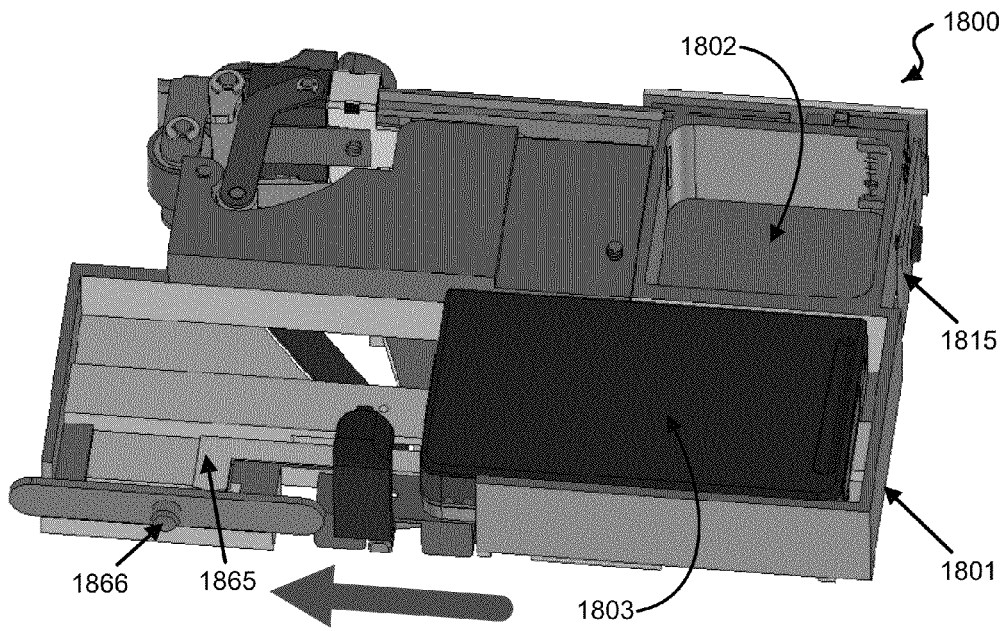
Figure 18E:
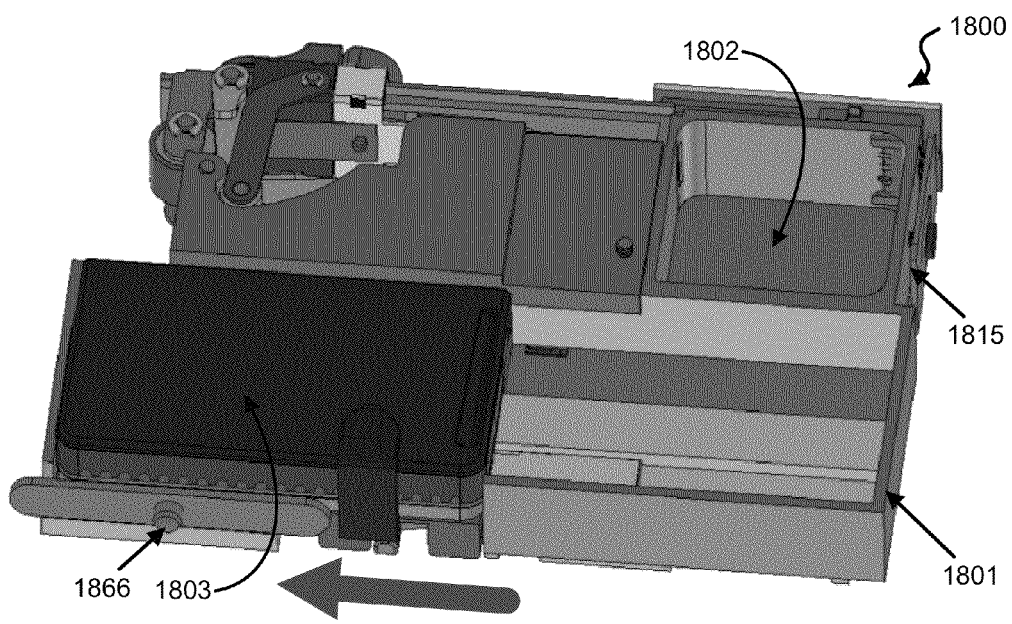

1860 in the linear direction advances the lancet cartridge 1803 by one lancet position from a previous lancet position of the lancet cartridge 1803 in a lancet loading compartment 1808, in which the lancet loading compartment 1808 is a compartment of the chassis 1801 to initially load the lancet cartridge 1803. The movement of the sliding component 1860 in the linear direction advances the lancet cartridge 1803 by one lancet position such that the lancet that is to be fired is placed in a position aligned in the firing path of the firing hammer component 1885 for projection of that lancet. As shown in FIG. 18D, the sliding component 1860 includes a spring loaded pawl 1867 that engages an indented (e.g., toothed) rack of the lancet cartridge 1803 (shown later in FIG. 22A) to latch or clutch the lancet cartridge 1803 during the cocking motion (e.g., the advancement of the lancet advance component 1840 forward). The spring loaded pawl 1867 releases the rack during the return motion of the sliding component 1860. The pawl can be driven by the short arm of the lancet advance component 1840 as it moves the sliding component 1860 in the linear direction. As shown in FIG. 18E, which shows the device 1800 flipped 180 degrees from the side shown in FIG. 18D, the advancement of the lancet cartridge 1803 moves from a position in the lancet loading compartment 1808 in the linear direction shown by the arrow. In some implementations, the lancet cartridge 1803 is not advanced while the sliding button actuator mechanism is implemented from the initial position to the cocked position. In such examples, the final lancet stored in the lancet cartridge 1803 can be reused over and over again even as the spring loaded pawl 1867 is implemented to latch the next rack as the sliding component 1860 moves in the linear direction (and return it to its initial position). In this exemplary case, the spring loaded pawl 1867 clutches a void and does not alter the position of the lancet cartridge 1803, allowing the final lancet stored in the cartridge to remain in a position to be fired repeatedly by the firing hammer component 1885.

Additionally, in some implementations, the actuator mechanism can include a lancet depth adjustment component 1865 that sets a particular position to control the depth at which the lancet protrudes from the device when fired. Studies have shown that more than a third of the participants in the studies stated that pain is the main reason people with diabetes refrain from regular blood glucose testing. For example, to potentially reduce pain felt by a user, the penetration depth of a lancet can be minimized by adjusting the lancet depth adjustment component 1865 to a particular position such that the selected penetration depth is as shallow as possible while still producing blood at the puncture site of the user. The exemplary lancet depth adjustment component 1865 includes a series of steps that are fitted within a channel along the exterior of the lancet cartridge 1803, as shown later in FIGS. 22A and 22B. For example, one of the steps of the lancet depth adjustment component 1865 can be positioned at the end of the travel path of the readied lancet. For example, the particular step can be aligned by moving the exemplary lancet depth adjustment component 1865 using a knob 1866 or another type interface on the exterior of the chassis 1801. For example, a step 1865a at a distal end of the lancet depth adjustment component 1865 can be positioned in the travel path of the fired lancet to create a shorter distance of travel of the fired lancet, thereby minimizing the length at which the tip of the lancet can protrude outwards from the device during firing. For example, a step 1865b of the lancet depth adjustment component 1865 can be positioned in the travel path of the fired lancet to create a longer distance of travel of the fired lancet, thereby maximizing the length at which the tip of the lancet can protrude outwards from the device during firing.

Figure 19B:
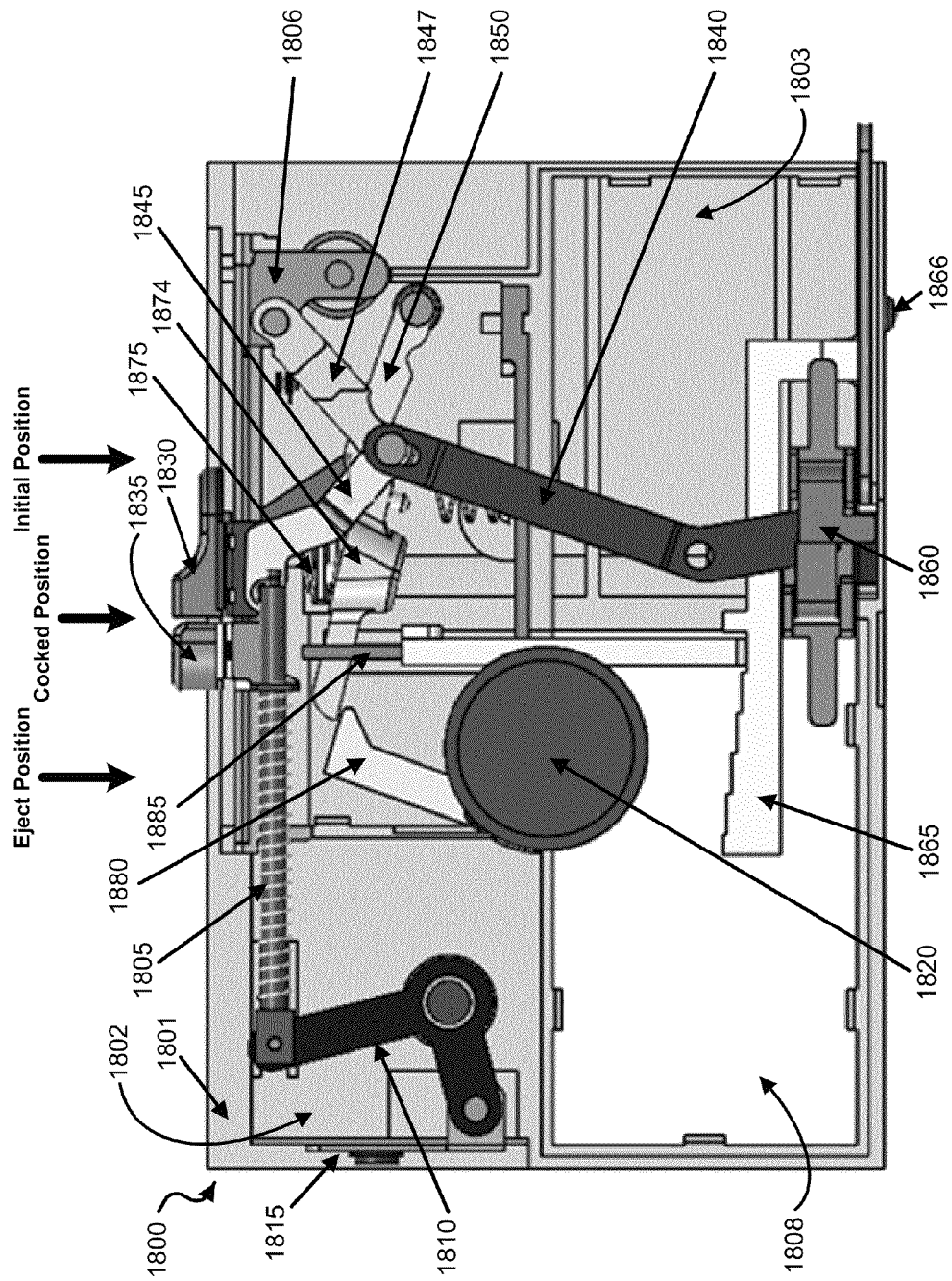

FIGS. 19A and 19B show a sequence of schematic illustrations showing the movement of the sliding button from the initial position to the cocked position. Implementation of the analyte testing device 1800 can include a first operation of the actuator mechanism that can (1) advance a new test strip from a position within the analyte sensor cartridge 1802 to a position outside of the chassis 1801 partially exposing the sample receiving site of the test strip and (2) advance the firing hammer component 1885 to the firing position for projection of a lancet from the lancet cartridge 1803, in which both advancements are initiated by the same operation of the actuator mechanism. Additionally or optionally, for example, implementation of the first operation of the actuator mechanism can (3) advance the lancet cartridge 1803 to a position in which the lancet is positioned in the firing path of the firing hammer component 1885 for projection of the lancet. The first operation can be performed using one hand. For example, the first operation can be implemented by a thumb or other finger sliding the sliding button (e.g., pushing the button pad of the cocking button 1830) from the initial position (as shown in FIG. 19A) forward to the cocked position (as shown in FIG. 19B), e.g., such that the chassis 1801 of the device 1800 rests in the palm of the user's hand.

FIG. 19A shows the status of the analyte testing device 1800 before operation, in which the components of the actuator mechanism are in an initial state and/or 'home' position. For example, the sliding button is set in the initial position; the spring of the spring-loaded arm component 1805 is in the initial compression state and the rod shaft of the spring-loaded arm component 1805 and the door crank component 1810 are not extended forward; the door 1815 is in the closed position covering the slot opening of the analyte sensor cartridge 1802; the lancet advance component 1840, as well as the lancet cocking link 1845 and the lancet cocking crank 1847, are not extended forward; the sliding component 1860 is in a position ready to advance the lancet cartridge 1803; and the lancet fire arm component 1850 is not raised upwards and rests between the return spring 1870 and the firing spring 1875 (in the initial compression state).

FIG. 19B shows the status of the analyte testing device 1800 during the implementation of the first operation. For example, the sliding button is set in the cocked position; the spring of the spring-loaded arm component 1805 is in the intermediate compression state and the rod shaft of the spring-loaded arm component 1805 and the door crank component 1810 are extended forward; the door 1815 is in the opened position permitting a test strip to be exposed from the analyte sensor cartridge 1802; the lancet advance component 1840, as well as the lancet cocking link 1845 and the lancet cocking crank 1847, are extended forward; the sliding component 1860 is in a position that has advanced the lancet cartridge 1803 (e.g., by one lancet position); and the lancet fire arm component 1850 is raised upwards, compressing the firing spring 1875, and seated upon the top surface of the trigger catch component 1880, having positioned the firing hammer component 1885 in the firing position.

Implementation of the analyte testing device 1800 can include a second operation of the actuator mechanism that can project (e.g., fire) the lancet to prick a user to draw blood for analysis in the test. This operation is described later in the patent document, as shown in FIGS. 24A-24C and 25A and 25B.

Figure 20A:
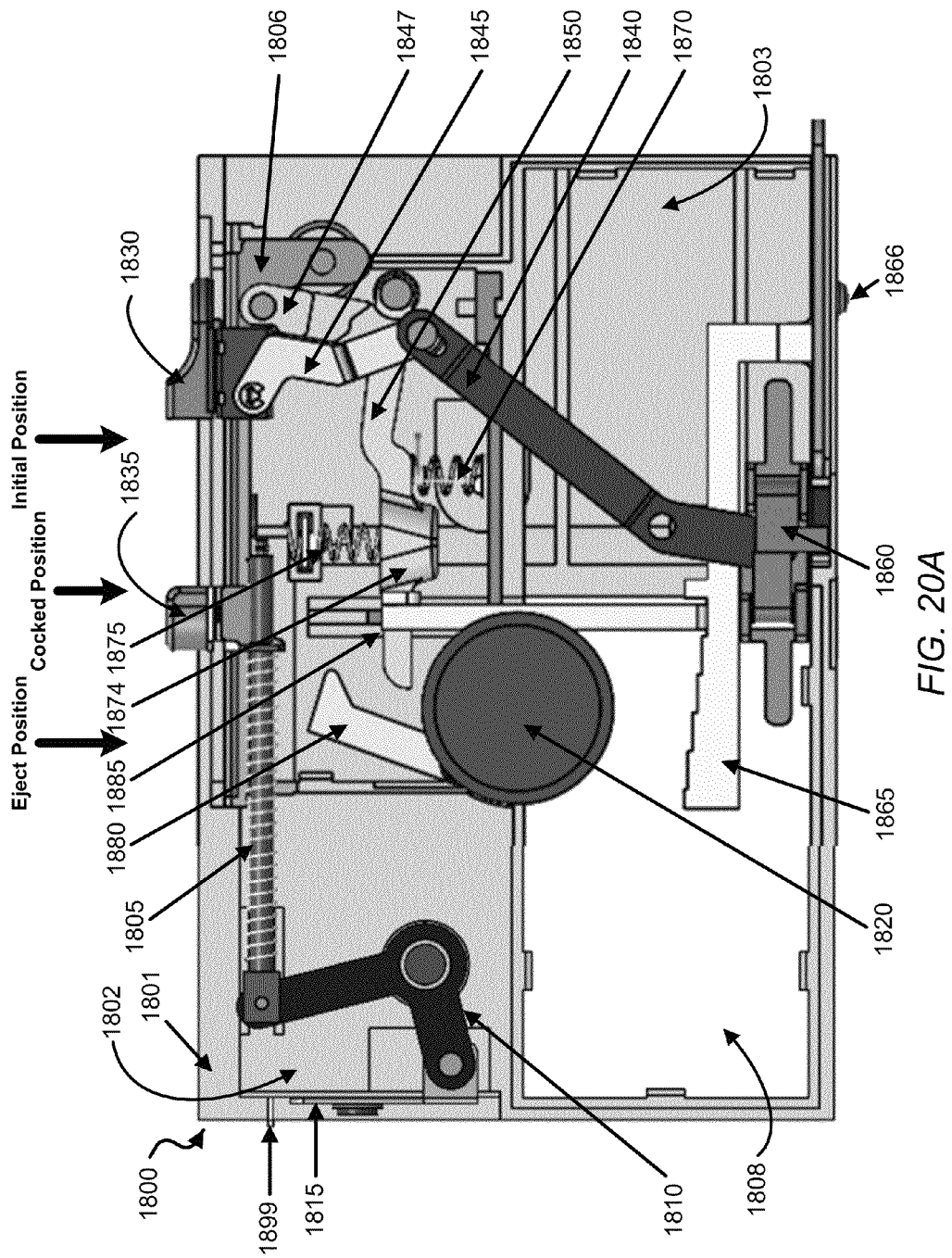
FIGS. 20A-20C show schematics illustrating another operation of the exemplary actuator mechanism of the analyte testing device.
Figure 20B:
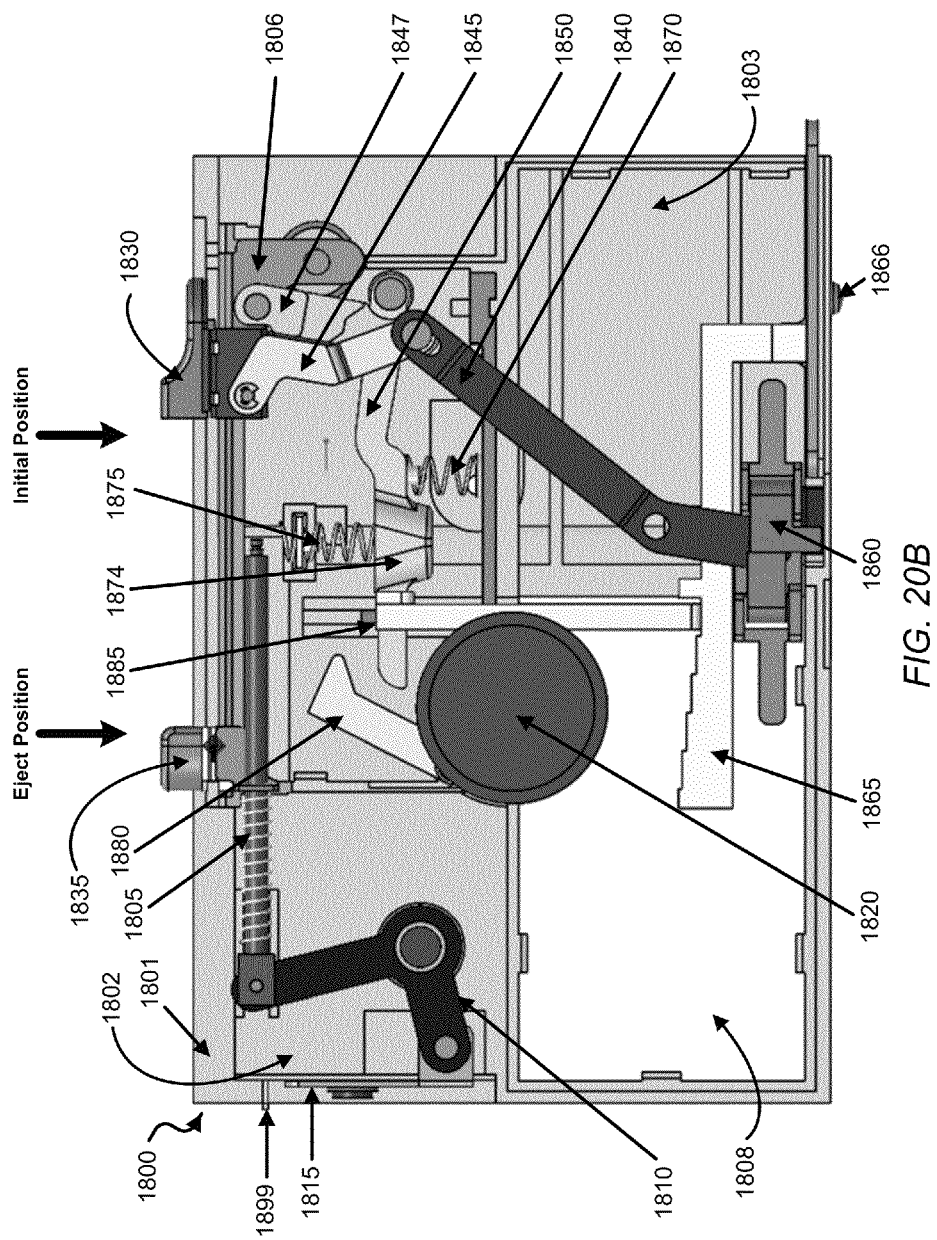
Figure 20C:
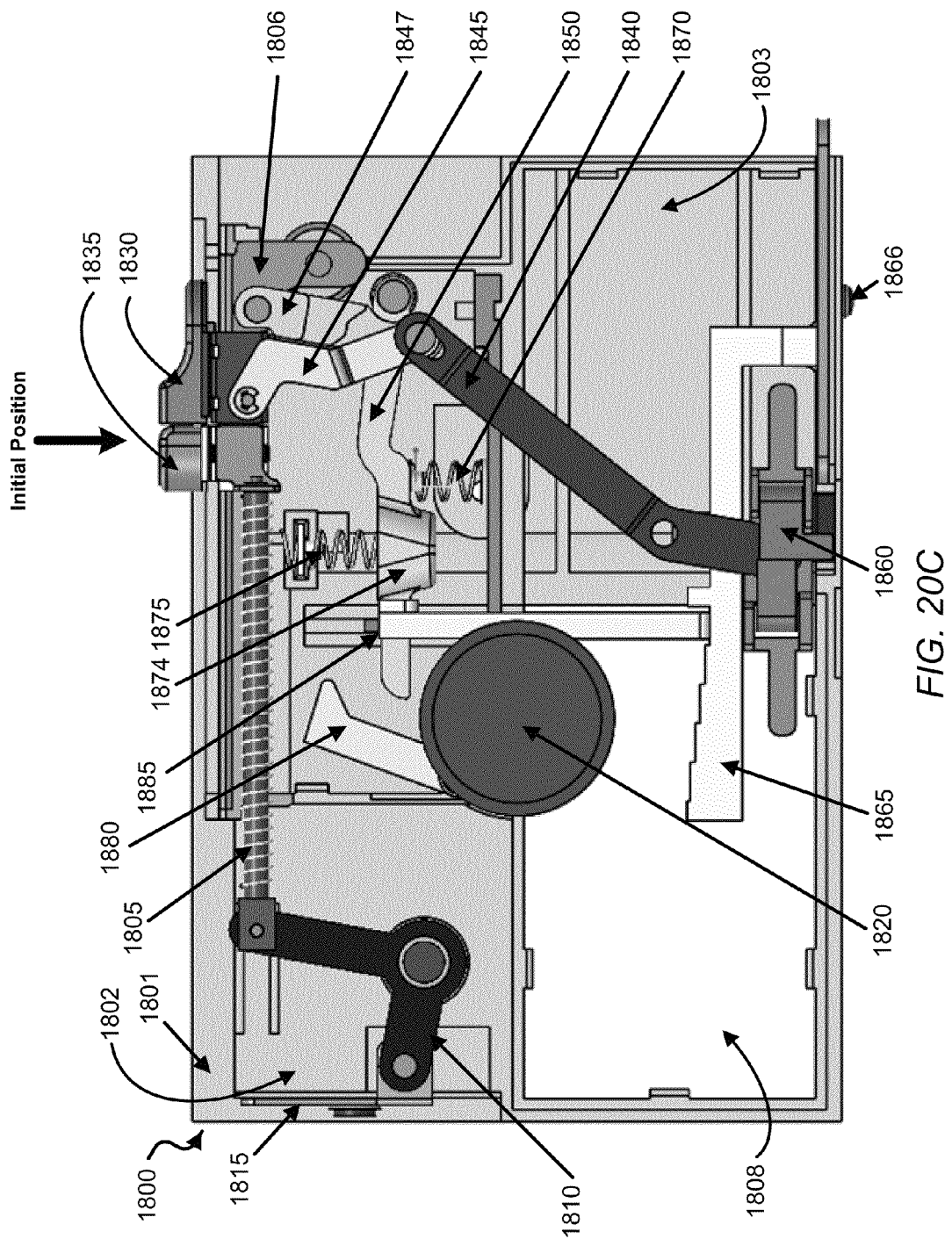

FIGS. 20A, 20B and 20C show a sequence of schematic illustrations of the movement of the eject button 1835 of the sliding button from the cocked position to the eject position and back to the initial position. Implementation of the analyte testing device 1800 can include a third operation of the actuator mechanism that can eject the used test strip from its exposed position outside of the chassis 1801 and reset the analyte testing device 1800 for another test, e.g., return the any of the components of the actuator mechanism that are not in the home position back to the home position. The third operation can be performed using one hand. For example, the third operation can be implemented by a thumb or other finger sliding the sliding button (e.g., pushing the eject button pad of the eject button 1835) from the cocked (as shown in FIG. 20A) forward to the eject position (as shown in FIG. 20B), which can return back to the initial position (as shown in FIG. 20C), e.g., such that the chassis 1801 of the device 1800 rests in the palm of the user's hand.

FIG. 20A shows the status of the analyte testing device 1800 after implementation of the second operation prior to the third operation, in which some of the components of the actuator mechanism are in a position for receiving the testing sample and other components of the actuator mechanism are in the home position. For example, the cocking button 1830 of the sliding button is set in the initial position; the eject button 1835 of the sliding button is set in the cocked position; the spring of the spring-loaded arm component 1805 is in the intermediate compression state and the rod shaft of the spring-loaded arm component 1805 and the door crank component 1810 remain extended forward; the door 1815 is in the opened position exposing a test strip 1899 from the analyte sensor cartridge 1802 (e.g., to receive a sample from a user); the lancet advance component 1840, as well as the lancet cocking link 1845 and the lancet cocking crank 1847, are in the home position; the sliding component 1860 is in home position; and the lancet fire arm component 1850 and the return spring 1870 and the firing spring 1875 are in the home position.

FIG. 20B shows a schematic of the analyte testing device 1800 during the implementation of the third operation, in which the actuator mechanism ejects the test strip from the device (e.g., after receiving blood from a patient and receiving the results of the test of the blood sample, for example, which can be displayed on a display of the device 1800). For example, the eject button 1835 of the sliding button has been advanced to the eject position; the spring of the spring-loaded arm component 1805 is further compressed beyond the intermediate compression state and the rod shaft of the spring-loaded arm component 1805 and the door crank component 1810 remain extended forward; the door 1815 remains in the opened position while the test strip 1899 is at least partially protruding from the slot opening (e.g., and the door immediately closes as the test strip 1899 is fully ejected); and the cocking button 1830 of the sliding button, the lancet advance component 1840, the lancet cocking link 1845, the lancet cocking crank 1847, sliding component 1860, the lancet fire arm component 1850 and the return spring 1870 and the firing spring 1875 are in the home position.

FIG. 20C shows a schematic of the analyte testing device 1800 after implementation of the third operation, in which the components of the actuator mechanism are in the home position.

Figure 21A:
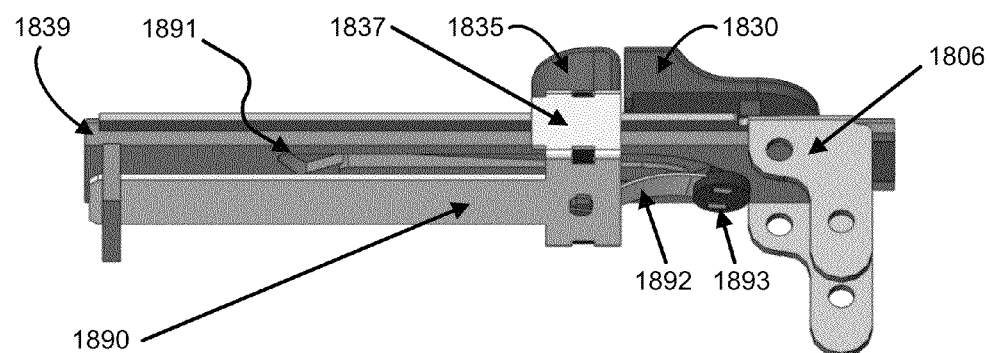
FIGS. 21A and 21B show schematics of exemplary sliding button components of the actuator mechanism of the analyte testing device.
Figure 21B:
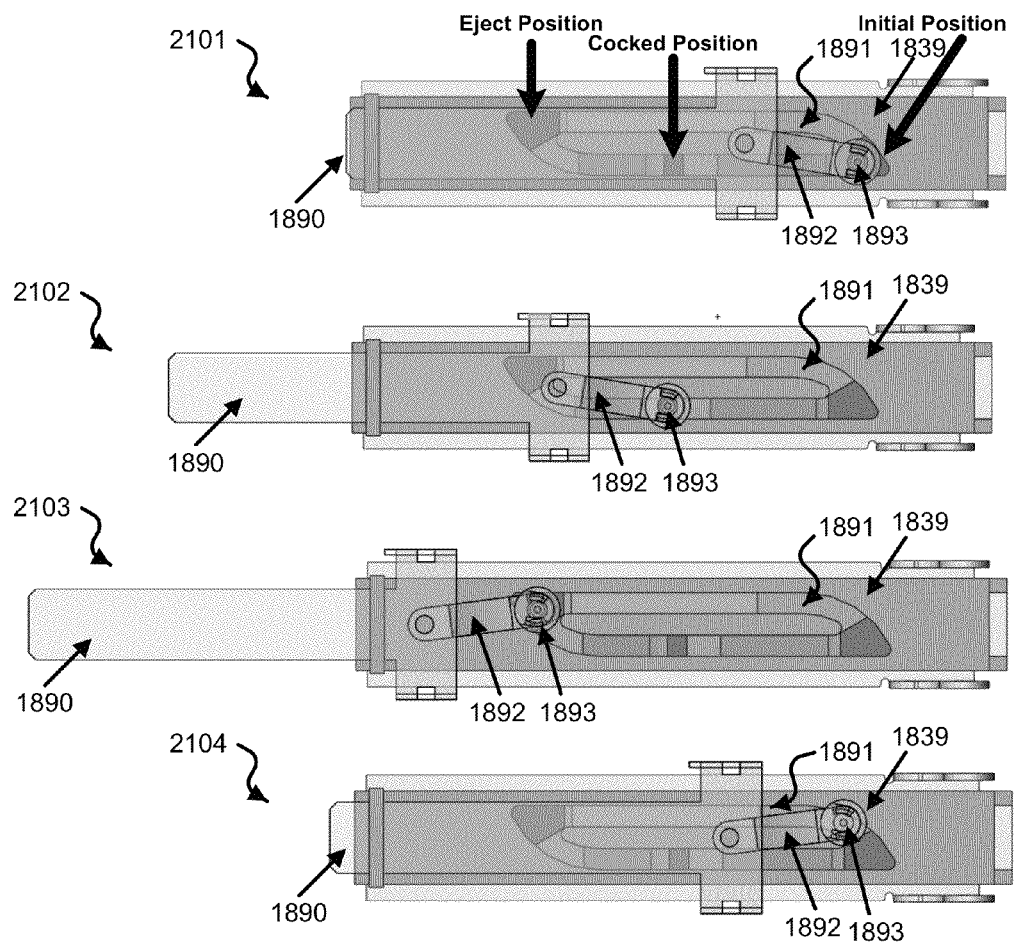

FIGS. 21A and 21B show schematics of the exemplary sliding button components of the actuator mechanism of the analyte testing device 1800. As shown in FIG. 21A, the sliding button includes the cocking button 1830 and the eject button 1835 that can move (e.g., slide) translationally along the sliding track 1839. The eject button 1835 includes the eject base component 1837, which is coupled to a projection tongue component 1890 of the actuator mechanism to project a test strip from the analyte sensor cartridge 1802, e.g., by pushing the test strip out of the slot opening of the device 1800. For example, the analyte sensor cartridge 1802 can be configured to include an opening on an internal side to allow the projection tongue component 1890 to enter the cartridge 1802 and make contact with the test strip and move (e.g., push) the test strip through the slot opening. In some implementations, for example, the eject base component 1837 and the projection tongue component 1890 can be a single component. The bottom side of the sliding track 1839 includes an indented channel 1891, e.g., which is shaped in a closed-loop path, as shown in FIG. 21B. The sliding button includes sliding pin 1893 that is configured within the indented channel 1891 of the sliding track 1839 to control the motion of the sliding pin 1893 when the sliding button is engaged and in motion. The sliding pin 1893 is coupled to a connector link 1892 that connects the sliding pin 1893 to the projection tongue component 1890. The indented channel 1891 includes various depths along the channel to provide a ramp for the sliding pin 1893 to travel. For example, the ramping of the indented channel 1891 can control the sliding pin 1893 to travel along a single pathway of the closed-loop path (e.g., in a clockwise travel in the path of the indented channel 1891). The indented channel 1891 includes various catch stops along the channel for the sliding pin 1893 to stop in the initial position, the cocked position, and the eject position and prevent back-travel of the sliding pin 1893 along the pathway of the indented channel 1891. The indented channel 1891 can also include a safety catch stop located at a position between the initial position and the cocked position that can prevent back-travel of the sliding pin 1893 from returning to the initial position before the sliding button has fully traveled to the catch stop of the cocked position to implement the first operation. For example, premature back-travel of the sliding pin 1893 to the initial position can result in the projection tongue component 1890 losing contact with the analyte sensor it projects (e.g., during the first or third operations), which may result in a subsequent analyte sensor (e.g., directly under the advanced analyte sensor in the analyte sensor cartridge 1802) raising up within the cartridge in the analyte sensor projection path, thereby potentially creating a jam of the two analyte sensors in the analyte sensor cartridge 1802. The safety catch stop can prevent potential jamming of analyte sensors in the cartridge in the event that the sliding button is brought back prematurely by stopping the sliding button from returning to the initial position prior to arriving at the catch stop of the cocked position, thereby maintaining at least a portion of the projection tongue component 1890 in the analyte sensor projection path.

FIG. 21B shows a sequence of schematic illustrations showing the movement of the sliding button along the sliding track 1839 from the initial position to the cocked position to the eject position and back to the initial position. For example, as shown in the schematic 2101 of FIG. 21B, prior to the first operation of the actuator mechanism, the sliding pin 1893 is stationary in a catch stop of the initial position, such that the projection tongue component 1890 is in a retracted position located in a region under the sliding track 1839. For example, as shown in the schematic 2102 of FIG. 21B, implementation of the first operation of the actuator mechanism moves the sliding pin 1893 from the catch stop of the initial position to a catch stop of the cocked position, such that the projection tongue component 1890 is partially protruded from the region under the sliding track 1839 (e.g., which can push the test strip partially out of the device to expose a portion of the test strip). For example, as shown in the schematic 2103 of FIG. 21B, implementation of the third operation of the actuator mechanism moves the sliding pin 1893 from the catch stop of the cocked position to a catch stop of the eject position, such that the projection tongue component 1890 is fully protruded from the region under the sliding track 1839 (e.g., which can push the test strip entirely out from the device to eject the test strip). For example, as shown in the schematic 2104 of FIG. 21B, implementation of the third operation of the actuator mechanism also moves the sliding pin 1893 from the catch stop of the eject position back to the catch stop of the initial position, such that the projection tongue component 1890 is retracted back to the region under the sliding track 1839. For example, in some implementations, the catch stop of the eject position can be configured not to catch the sliding pin 1893 and allow the sliding button to slide back to the initial position in one continuous movement.

Figure 22A:
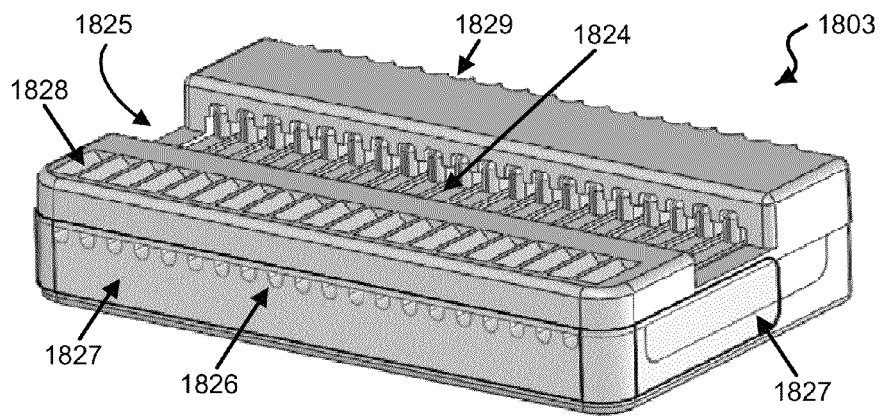
FIGS. 22A-22C show schematics of an exemplary lancet cartridge of the analyte testing device.
Figure 22B:
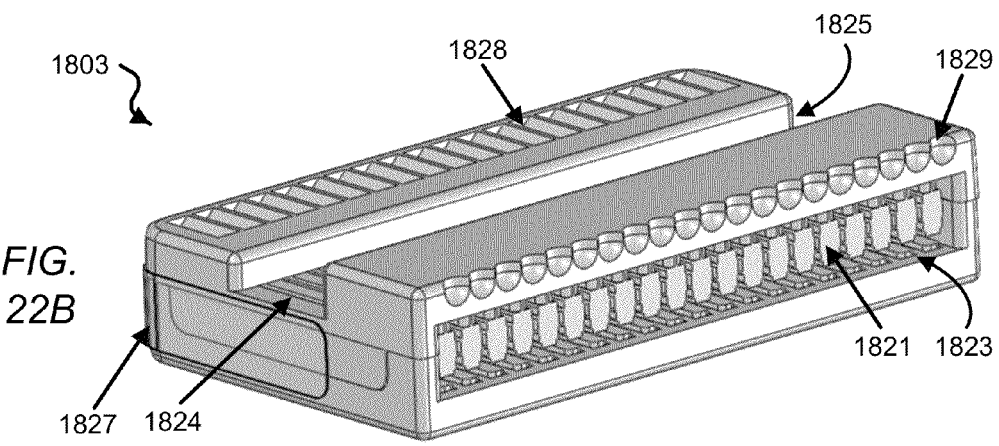
Figure 22C:
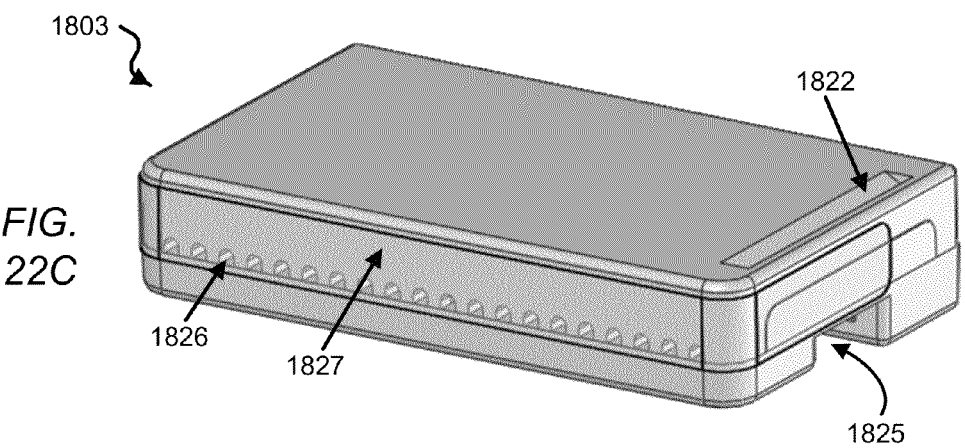

FIGS. 22A-22C show schematics of the lancet cartridge 1803 of the analyte testing device 1800. FIG. 22A shows a three dimensional view of an internal side and bottom side of the lancet cartridge 1803. The lancet cartridge 1803 includes a channel 1825 along the exterior of the internal side of the cartridge. The channel 1825 provides a region in which the lancet depth adjustment component 1865 passes through such that a step of the series of steps can be aligned in the firing path of the lancet to be fired. The lancet cartridge 1803 includes a toothed rack 1828 along the exterior of the internal side of the lancet cartridge 1803. The toothed rack 1828 provides indentations into the exterior that can engage the spring loaded pawl 1867 for the advancement of the lancet cartridge 1803 in the linear direction, e.g., which can be implemented in the first operation. The lancet cartridge 1803 includes a covering layer 1827 (e.g., such as a film) along the exterior of the bottom side of the lancet cartridge 1803 (e.g., which is shown to wrap around the side(s) of the cartridge). The covering layer 1827 provides a protective covering over openings 1826 to the lancet chambers to protect the lancet from contaminations and maintain a sterile environment within the chambers, as well as bonds the top and bottom of the lancet cartridge 1803 together. The lancet cartridge 1803 includes open troughs 1824 within the channel 1825 to allow a spring arm of a lancet (shown later in FIGS. 25A and 25B) to return to its initial position after the lancet has been fired.

FIG. 22B shows a three dimensional view of an internal side and top side of the lancet cartridge 1803. The lancet cartridge 1803 includes lancets 1821, in which a contact side of each lancet 1821 is exposed out of an opening 1823 of the top side lancet cartridge 1803 such that the firing hammer component 1885 can contact and move the lancet 1821, e.g., upon firing the lancet implemented in the second operation. The lancet cartridge 1803 includes detents 1829 along an edge of the top and internal side of the cartridge to retain an indexed position of the lancet cartridge after advancement. For example, the movement of the sliding component 1860 in the linear direction advances the lancet cartridge 1803 by one lancet position that is indexed by the detent 1829 such that a lancet that is to be fired is placed in a position aligned in the firing path of the firing hammer component 1885 for projection of that lancet.

FIG. 22C shows a three dimensional view of an external side and the bottom side of the lancet cartridge 1803 showing an indented catch 1822 for a user to remove the cartridge with the user's finger.

Figure 23A:
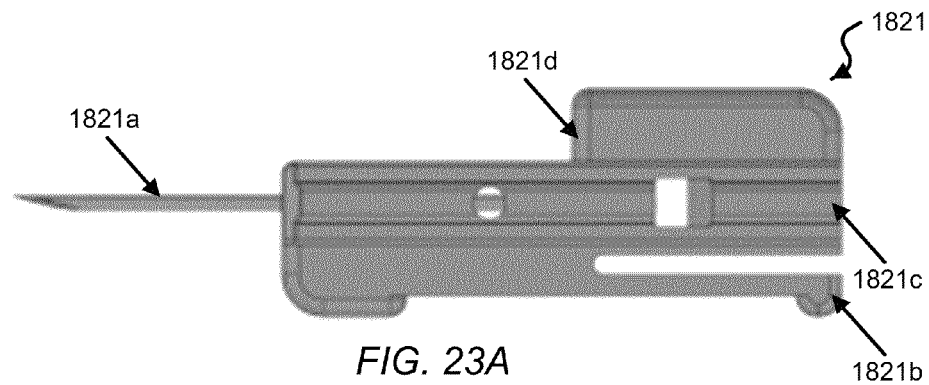
FIG. 23A shows a schematic of an exemplary lancet.

FIG. 23A shows a schematic of the lancet 1821. The lancet 1821 includes a lance 1821*a* (also referred to as a needle) that can be used to puncture or prick a user upon projection from the device 1800, e.g., to draw blood from the puncture or prick. The lancet 1821 includes a leaf spring 1821*b* including a notch on a split tail of the lancet 1821 that can be used to provide a positive engagement with the lancet cartridge 1803 to retain the lancet 1821 in a rest position within the cartridge, as shown in the FIG. 23B. The lancet 1821 includes a guide rail structure 1821*c* that protrudes out along the side of the lancet 1821 in a straight line which can align with a guide track 1804 inside the lancet chamber 1807 to control the projection of the lancet to be substantially entirely linear or straight motion. The lancet 1821 includes a retract structure 1821*d* that can engage with a lancet return spring to retract the lancet back into the lancet cartridge 1803.

Figure 23B:
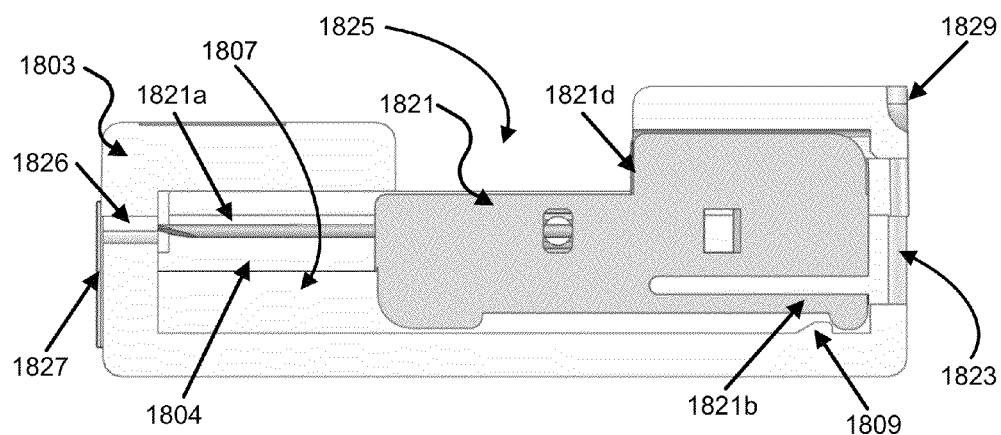
FIGS. 23B and 23C show schematics of the exemplary lancet in the lancet cartridge.
Figure 23C:
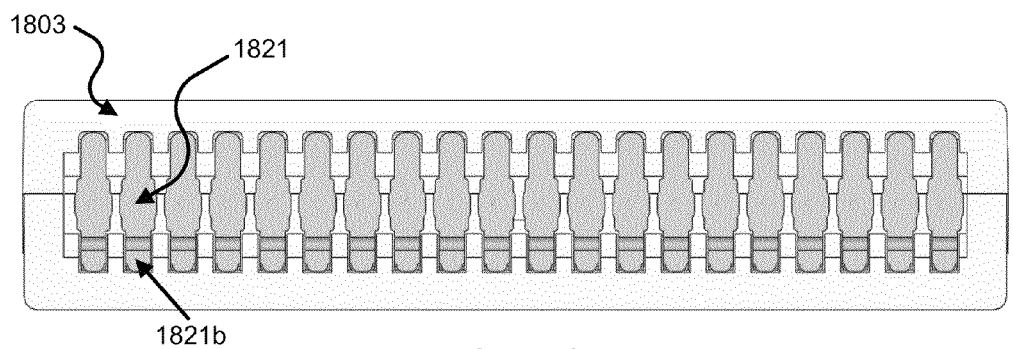

FIGS. 23B and 23C show schematics of the lancet 1821 in the lancet cartridge 1803. FIG. 23B shows a cross sectional side view of the lancet 1821 in the rest position within the lancet cartridge 1803. For example, in the rest position, a curved protrusion notch of the leaf spring 1821*b* is aligned in a groove or indentation formed by a retention bump 1809 of the lancet chamber 1807 of the lancet cartridge 1803. The retract structure 1821*d* of the lancet 1821 is positioned outside of the channel 1825 and within the casing of the lancet cartridge 1803. The lance 1821*a* is positioned near the opening 1826 within the lancet chamber 1807 of the lancet cartridge 1803. The covering layer 1827 is intact and not punctured by the lance 1821*a*. FIG. 23C shows a top view of the lancet cartridge 1803 showing a plurality of lancets 1821 contained within the cartridge. As shown in the figure, each lancet 1821 can be encased within the lancet chamber with a tight tolerance to closely fit the lancet, e.g., with a tight alignment of the guide rail 1821*c* with the guide track 1804.

FIGS. 24A-24E show a sequence of schematic illustrations showing the projection of the lancet 1821 based on the operation of the actuator mechanism. Implementation of the second operation of the actuator mechanism can project (e.g., fire) the lancet to prick a user to draw blood for analysis in the test. The second operation can be performed using one hand. For example, the second operation can be implemented by a thumb or other finger pressing the firing button 1820, e.g., such that the chassis 1801 of the device 1800 rests in the palm of the user's hand. For example, pressing the firing button 1820 retracts the trigger catch component 1880 such that the lancet fire arm component 1850 can slide off from its seated position on the top surface of the trigger catch component 1880, thereby releasing the firing hammer component 1885 from the firing position. The firing spring 1875 (and the weight 1874) can contribute to driving the lancet fire arm component 1850 downward to drive the firing hammer component 1885 downward and into the lancet cartridge 1803 through the opening 1823. The firing hammer component 1885 impacts the lancet 1821 and drives the lancet 1821 along the guide track 1804 in the lancet chamber 1807 in a linear motion to project the lance 1821*a* straight through the opening 1826 and out of the device 1800.

FIG. 24A shows a cross sectional side view of some components of the actuator mechanism in the cocked position prior to implementation of the second operation to fire the lancet 1821. For example, in the cocked position, the firing hammer component 1885 is in the firing position within the chassis 1801. A lancet return spring 1898 of the actuator mechanism is aligned along the top side of the channel 1825 of the lancet cartridge 1803, which can rest against the retract structure 1821*d* of the lancet 1821. For example, the lancet return spring 1898 can be utilized to return the lancet 1821 to the rest position after the lancet has been fired. FIG. 25 shows three dimensional cross sectional schematics of the lancet return spring 1898 in the analyte testing device 1800. In some examples, the actuator mechanism can include a wire spring 1897 that assists in the retraction of the firing hammer component 1885 to the home position after it has been fired.

FIG. 24B shows an enlarged cross sectional side view of the lancet 1821 in the rest position within the lancet cartridge

1803 prior to implementation of the second operation. For example, in the rest position, the curved protrusion notch of the leaf spring 1821*b* is aligned in the groove or indentation formed by the retention bump 1809 in the lancet chamber 1807 of the lancet cartridge 1803. The retract structure 1821*d* of the lancet 1821 is positioned within the casing of the lancet cartridge 1803, e.g., by a force applied by the lancet return spring 1898. The lance 1821*a* is positioned near the opening 1826 within the lancet chamber 1807 of the lancet cartridge 1803. The covering layer 1827 is intact and not punctured by the lance 1821*a*.

Figure 24C:
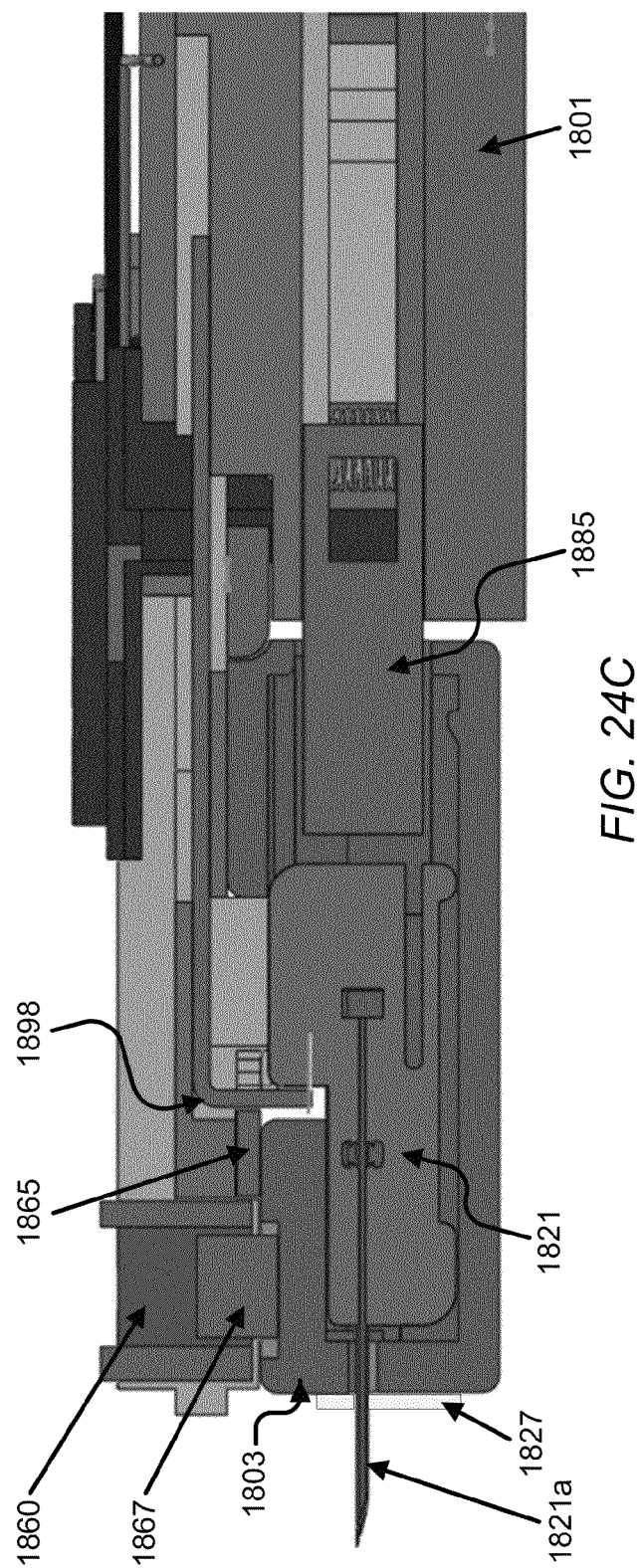
Figure 25:
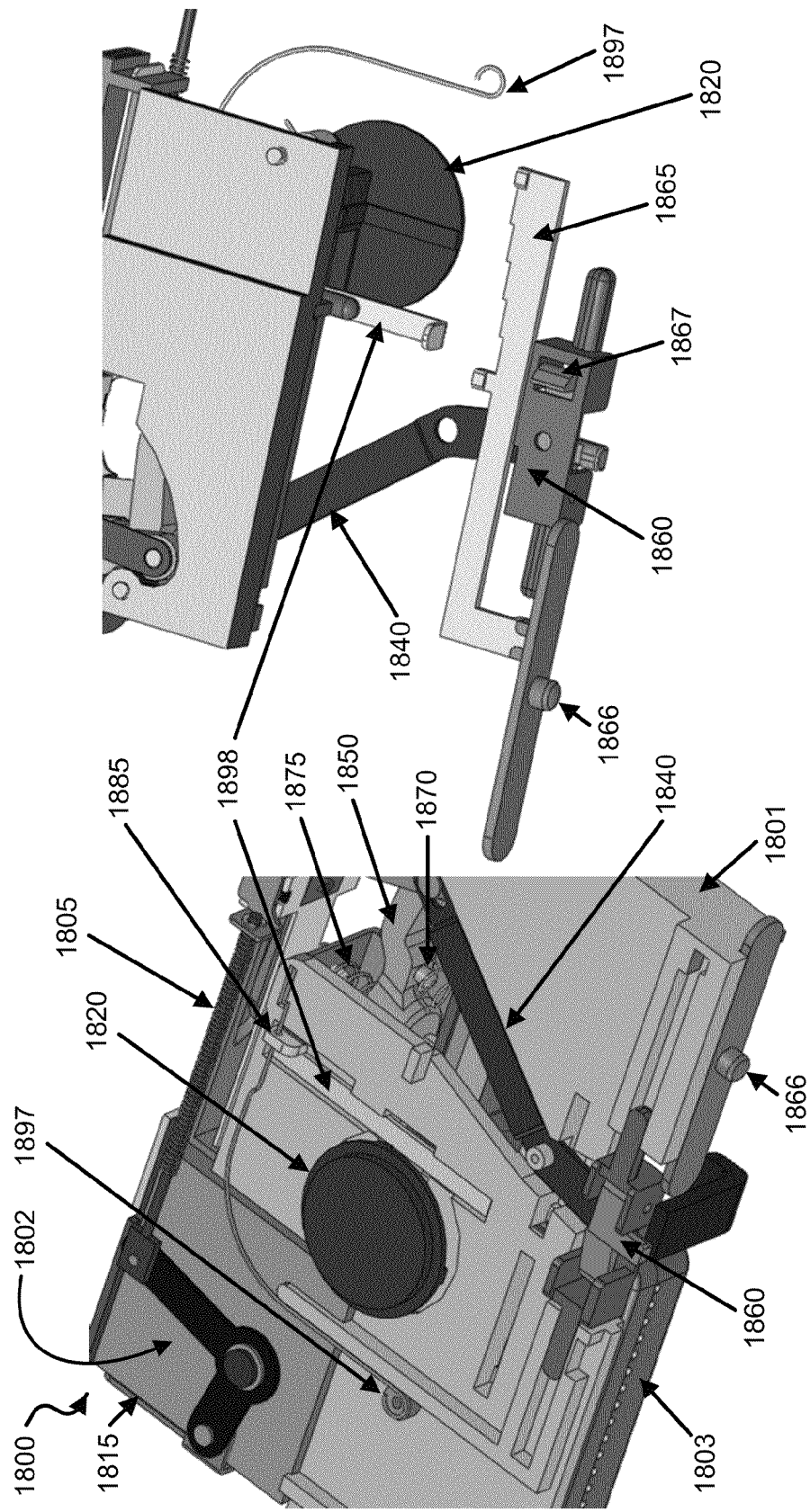
FIG. 25 shows schematics of components of the exemplary actuator mechanism of the analyte testing device.

FIG. 24C shows a cross sectional side view of the some components of the actuator mechanism during the implementation of the second operation to fire the lancet 1821. For example, during firing, the firing hammer component 1885 impacts the lancet 1821 and continues into the lancet chamber 1807 of the lancet cartridge 1803 to drive the lancet 1821 in a substantially straight motion. The lance 1821*a* travels through the opening 1826 and pierces the covering layer 1827 as it exits the device. Upon reaching the maximum travel distance, the firing hammer component 1885 is returned to the home position and the force applied by the lancet return spring 1898 against the retract structure 1821*d* of the lancet 1821 can drive the lancet back to the rest position.

Figure 24D:
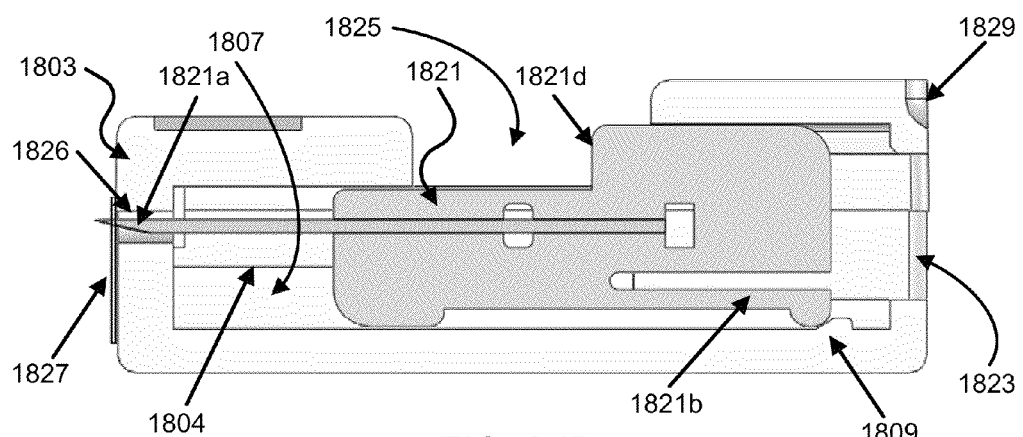
Figure 24E:
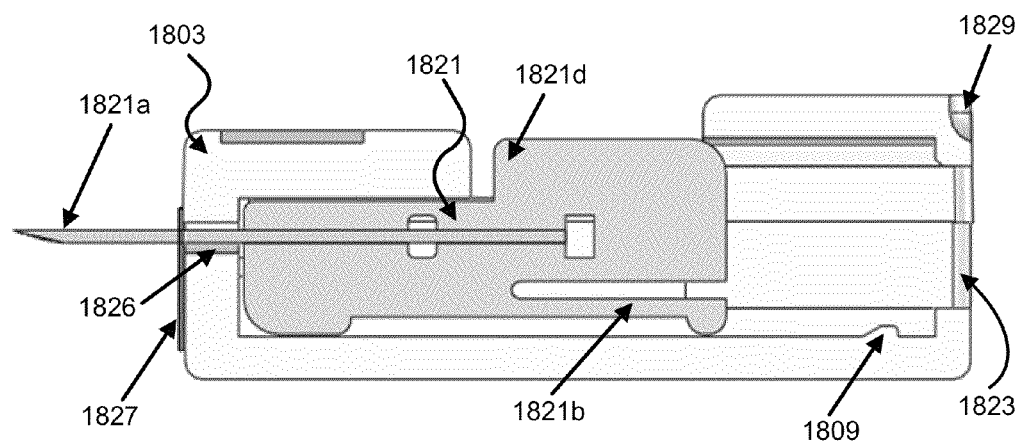

FIGS. 24D and 24E show enlarged cross sectional side views of the lancet 1821 within the lancet cartridge 1803 during the implementation of the second operation. For example, during firing, the lancet 1821 is driven in a substantially straight line in the chamber 1807 via the alignment of the guide rail structure 1821*c* of the lancet 1821 and the guide track 1804 of the lancet cartridge 1803. The force that initiates the linear movement of the lancet 1821 (e.g., the impact by the firing hammer component 1885) drives the curved protrusion notch of the leaf spring 1821*b* out of the groove or indentation formed by the retention bump 1809 in the lancet chamber 1807 of the lancet cartridge 1803. The retract structure 1821*d* of the lancet 1821 pushes against the lancet return spring 1898 such that the linear movement of the lancet 1821 is capable of overcoming force applied by the lancet return spring 1898 against the lancet. The lancet 1821 travels the available distance provided in the channel 1825, e.g., which can be based on the full length of the channel 1825 (e.g., 6 mm) or a smaller distance based on a particular step of the lancet depth adjustment component 1865 positioned within the firing pathway in the channel 1825. In some examples, the travel distance of the lancet 1821 during firing can be configured to be in a range between 4.5 mm and 6 mm based on the step of the lancet depth adjustment component 1865 positioned within the firing pathway in the channel 1825. In some examples, the travel distance of the lancet 1821 during firing can be controlled based on the adjusting the compressive force that can be applied by the lancet return spring 1898 against the retract structure 1821*d*. The lance 1821*a* travels through the opening 1826 and pierces the covering layer 1827 as it exits the device. Upon reaching the maximum travel distance, the firing hammer component 1885 is returned to the home position and the force applied by the lancet return spring 1898 against the retract structure 1821*d* of the lancet 1821 drives the lancet back to the rest position.

In another embodiment of the disclosed technology, systems, devices, and methods are described for an analyte testing system includes a hand-held analyte testing device and a docking station. The analyte testing device houses: (i) a plurality of lancets, (ii) a plurality of analyte sensors usable in conjunction with the lancets, (iii) electronics for deriving test data from the analyte sensors, (iv) a visual display that displays the test data, and (v) a data recording facility that records non-test data. The handheld device is used to prick a body member for drawing a blood sample, and test the blood sample for analytes such as glucose. The docking station has a power interface for providing power to the analyte testing device. The docking station also has a data interface and a storage facility that stores the test data and the non-test data.

In some implementations of this disclosed embodiment, the testing device and/or the docking station has a communication facility configured to transmit and receive with an external storage device (e.g., a medical provider server, home computer, local area network). The communication facility can be wired or wireless. In some implementations, the communication facility uses at least two wireless protocols. In other implementations, the communication facility transmits data a cell phone network. Contemplated data include test data, information derived from test data, and non-test data. In some implementations, the power interface is an inductive charging pad and the data interface is a wired connection, such as a USB port. The docking station can further include a second data interface, either wired or wireless, for exchanging data with an external device (e.g., home computer, laptop, smart phone, insulin pen, health test device). The data collected by the analyte testing device electronics can include test data (i.e., analyte testing results), information derived from the test data (e.g., reports, graphs, analytics, trends), and even non-test data, such as: diary information recorded as text and/or audio; supplies used; supplies ordered; food eaten, minutes exercised and estimated calories burned; amount of medication taken, time medication was taken, supplies available in a user's personal inventory, and supply ordering history. In some implementations, at least one of the docking station and testing device includes a panic button configured to alert a third party of a user's identity and condition. The docking station also preferably has a backup rechargeable battery that can replace a rechargeable battery of the handheld analyte testing device. In some implementations, the testing device display is an LCD touch screen that indicates (i) whether the analyte testing device is charging and (ii) whether data is being transferred between the analyte testing device and the docking station. It is also contemplated that the docking station can include a display for indicating a charge status and data exchange status. The display preferably includes a graph showing a maximum threshold line, minimum threshold line, and a test data line. The max/min threshold lines indicate help the user to determine whether analyte test results are within acceptable limits. In some implementations, the recording facility is a microphone and/or keypad, which can be used to record diary entries. In some implementations, at least one of the testing device and the docking station has a processor programmed to test the adequacy of a communication link between the testing device and the docking station. The docking station preferably has a processor and executable code that is configured to automatically (i) back-up the test data and the non-test data, (ii) track supply usage, and (iii) re-orders supplies. In some implementations, the plurality of lancets are contained in a lancet cartridge and the plurality of analyte sensors are contained in an analyte sensor cartridge. It is also contemplated that the analyte sensor cartridge can be separate from the lancet cartridge. In some implementations, the storage facility in the docking station is removable. The storage facility can also be configured to store data in a generic file format (e.g., pdf, doc, xml, eps, html, jpeg, rtf, and txt). For example, the storage facility is password protected and stores the test data and non-test data using encryption. In some implementations, the analyte testing system also includes an insulin pen for administering medication. The pen preferably has a wireless communication facility configured to exchange data with the testing device.

FIGS. 26a and 26b show an analyte testing system 8100 comprising a handheld analyte testing device 8200 and a docking station 8300. Device 8200 couples with station 8300 via power interface 8310 and data interface 8320, as shown in FIG. 26b. Docking station 8300 can optionally be configured with a cradle or recessed portion for receiving device 8200 in a secure manner. FIG. 26a shows device 8200 disconnected from station 8300. Power interface 8310 is an inductive pad configured to provide electrical power to a rechargeable battery within device 8200. An inductive pad advantageously allows device 8200 to charge without physically mating with the docking station. In alternative embodiments, power interface 8310 could comprise an electrical connector configured to mate with a connector on device 8200. Data interface 8320 is physical connector configured to mate with a connector on device 8200 and provides data connectivity between storage mediums in device 8200 and docking station 8300 (not shown). However, it is also contemplated that data interface 8320 could comprise a wireless transmitter communicatively coupled with a wireless transmitter of device 8200.

Interfaces 8310 and 8320 can be two separate and distinct interfaces, or alternatively, can be integrated into one interface. Power interfaces and data interfaces are well known. In one embodiment, data interface 8320 comprises a USB port and power interface 8310 comprises an inductive current loop. Interfaces 8310 and 8320 can utilize an industry standard or proprietary technology. In some embodiments, data interface 8320 is a wireless transceiver configured to communicate with a wireless transceiver of device 8200 using any number of wireless communication protocols and technologies (e.g., Bluetooth, wifi, cellular network, 802.11). The term wifi is used here generically to refer to a wireless local area network, rather than in a trademark sense to refer to Wi-Fi™. In such embodiments, station 8300 preferably uses at least two alternative wireless communication protocols so that a secondary communication link is available in case the primary communication link fails. Including multiple protocols also advantageously increases compatibility with other devices.

Docking station 8300 has a removable storage medium 8370 coupled with an internal processor/electronics (not shown), and is configured to automatically backup analyte testing results data from device 8200. The internal electronics are also preferably configured to analyze test results and identify trends. In addition to test data, it is further contemplated that other data can be stored and analyzed on station 8300 and/or device 8200. Such data can include time-stamped diary entries, either in text or audio format. For example, a user can record verbal comments on his or her physical health (e.g., severity and frequency of symptoms). Other data can further include: medication taken (amount, time), supplies used, supply order history, supplies remaining in the user's personal inventory, exercise (minutes, type), estimated calories burned, dietary intake information (protein, sugar, fat, sodium, etc) or any other information relevant and helpful for monitoring analytes and health issues. Contemplated supplies include, but are not limited to, lancets, test strips, and medication.

A removable storage medium 8370 advantageously allows a user to take the storage facility to a health care provider for sharing the health data. The data is preferably password protected and/or encrypted in order to maintain the user's privacy. The data is preferably stored in a common or standard format (e.g., pdf, doc, xml, eps, html, jpeg, rtf, and txt) so that a doctor can view the data without the need for custom software.

Docking station 8300 has an LCD touch screen display 8330 for displaying and inputting information. For example, display 8330 can show test results, history and trending of test results, supplies used, supplies remaining, or any other data helpful for monitoring analytes and health. In some embodiments, display 8330 shows the number of lancet and test strip cartridges remaining in the user's personal inventory (e.g., closet). Display 8330 can further be used for video conference communication with a health care professional or for displaying instructional videos on how to operate system 8100. Display 8330 can additionally serve as an input device for recording audio diary entries, dietary or exercise information, or any other data useful for monitoring analytes. However, it is also contemplated that an input device other than display 8330 can be included in station 8300 (e.g., buttons, key paid, microphone for voice-recognition commands).

Display 8330 can further display an indication of whether device 8200 is properly connected via power interface 8310 and data interface 8320. In addition, display 8330 can show whether power interface 8310 is rechargeable charging a battery of device 8200, estimated time to complete a full charge, and whether data is currently being exchanged via in interface 8320. The indicators can optionally comprise several LED lights having different colors and/or different blinking patterns.

Docking station 8300 can include additional data interfaces and can be configured to function as a hub for multiple handheld health monitoring devices. In this manner, docking station 8300 can act as a central point for gather a user's health data, analyzing the data, and transmitting the data to a health care provider. Station 8300 can also include a calibration mechanism for testing accuracy of device 8200. In addition, station 8300 can include electronics for testing the adequacy and operability of the testing device's communication facility.

FIG. 27 shows handheld analyte testing device 8200. Device 8200 is a lancing device integrated with an analyte meter. The housing of device 8200 has a first compartment 8210 and a second compartment 8220, for storing a lancet cartridge 8215 (see FIG. 29) and a analyte sensor cartridge 8225 (see FIG. 30), respectively. Device 8200 houses various electrical components (memory, processor, executable code, etc) configured to convert electrical signals from analyte test strip 8226 (see FIG. 30) into a test result reading. Device 8200 also has a data recording facility 8205 for recording data, and a display 8280 for displaying data.

Data recording facility 8205 and related electronics are used to store voice recordings of diary information as previously described. The electronics can also include a speaker for communicating data to a user and for prompting a user to use the device according to a pre-selected time and/or pre-selected time interval. In addition, the electronics can be equipped with an accelerometer or pedometer for measuring and calculating distance traveled and calories burned. In other aspects of the disclosed embodiments, the electronics of device 8200 preferably includes a processor programmed to correlate individual instances of data with time stamps. For example, test result data and diary entries can be time stamped and correlated. In addition, the processor can be programmed to make an evaluation of the data, and send a notification to different recipients as a function of the evaluation. In some embodiments, the processor is used to create static reports and saved in a generic file format onto removable storage medium 8370. Yet still, the processor can be programmed to keep track of inventory of lancets and test strips, automatically re-order supplies, and automatically backup data to storage medium 8370.

Device 8200 has an actuator 8240 configured to (i) cock a lancing apparatus within device 8200 (not shown), (ii) expose a test strip for use, and (iii) advance the lancet cartridge. The test strip is exposed via slot 8230. An ejection mechanism 8233 allows for ejection and disposal of the test strip after testing, without the need for directly touching the test strip.

Device 8200 has a LCD touch screen display 8280, which can be used in a similar fashion to display 8330 of station 8300. For example, display 8280 can be used to input diary information using a touch screen keypad. It is also contemplated that device 8200 can include a hard keypad. In some embodiments, display 8280 is used to display a graph that shows actual test data in relation to a maximum and minimum threshold line. The electronics of device 8200 can be programmed to notify the user or a medical care provider via a cellular network when test data exceeds the max/min thresholds.

Device 8200 also has a panic button 8290 that is configured to communicate the user's identity and health status to a third party. For example, the panic button can be used to contact an emergency service, identify the patient's name, current location, and health status. It is further contemplated that panic button 8290 can be configured to contact different persons (e.g., relative, home nurse, doctor, police) and convey different levels of urgency (e.g., low, moderate, high, critical) as a function of test results.

The housing of device 8200 and station 8300 can be made of plastic, metal, composite, or any other material with structural and mechanical properties suitable for housing a lancet cartridge, test strip cartridge, electronics, and a linkage mechanism. Device 8200 is preferably compact, with a height no more than 50 mm, a width no more than 17 mm, and a length no more than 100 mm. In some embodiments, the housing of device 8200 and station 8300 comprises an outer protective shell made of molded plastic and an inner desiccant liner to minimize exposure to moisture.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

Figure 28:
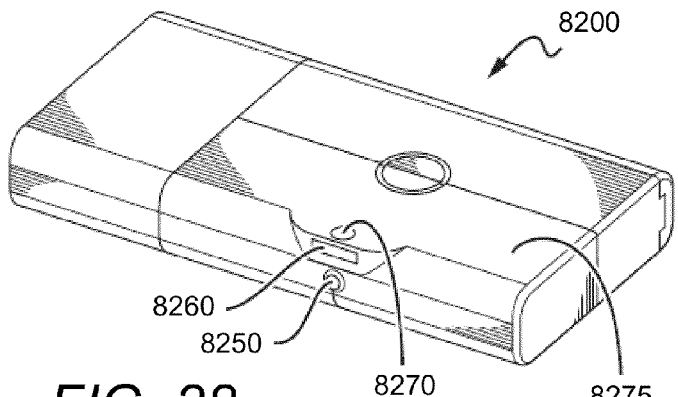
FIG. 28 is a perspective view of a back side of the handheld analyte testing device of FIG. 27.

FIG. 28 shows the back side of device 8200. Hole 8250 is used to eject a lancet for pricking a body part in order to draw a blood sample. Wheel 8260 is used to adjust the penetration depth of the lancet, while window 8270 displays the penetration setting. Cover 8275 is hingeably coupled to device 8200 and can be opened in order to insert a lancet cartridge 8215 and a analyte sensor cartridge 8225 into device 8200.

Figure 29:
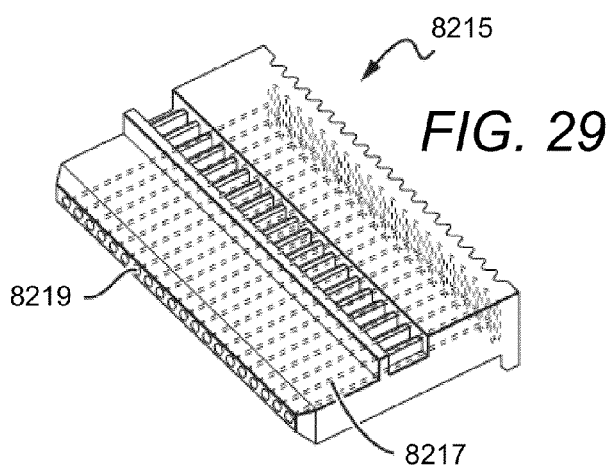
FIG. 29 is a perspective view of a lancet cartridge.

FIG. 29 shows one embodiment of a lancet cartridge 8215. Cartridge 8215 holds a plurality of lancets 8217. Holes 8219 are included on cartridge 8215 to allow a lancet to be temporarily ejected from cartridge 8215 and out of hole 8250 of device 8200 for drawing a blood sample. The lancet is safely retracted back into cartridge 8215 by a retraction mechanism within device 8200 (not shown).

Figure 30:
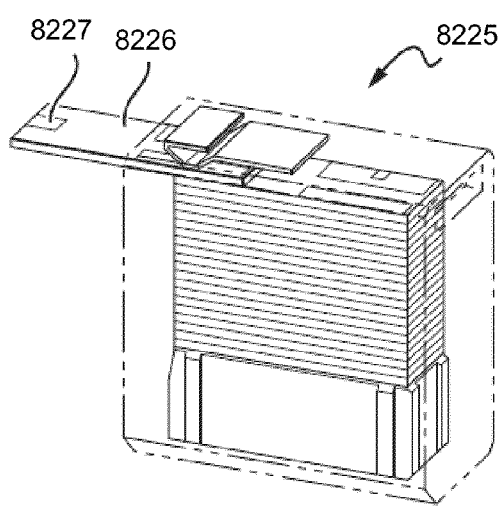
FIG. 30 is a perspective view of an analyte sensor cartridge.

FIG. 30 shows an analyte sensor cartridge 8225. Cartridge 8225 holds a plurality of test strips such as test strip 8226. Strip 8226 has an analyte sensor 8227 for testing an analyte. Analyte sensors are well known and generally comprise an absorbent material with a reactant (e.g., analyte-binding reagent). Sensor 8227 is configured to generate an electrical signal that is sent to the electronics of device 8200 for conversion into readable test data.

Cartridge 8225 can include any appropriate number of test strips, preferably between 15 and 25, more preferably between 18 and 22, and most preferably 20. The number of test strips also preferably equals the number of lancets in cartridge 8215, although other combinations are contemplated.

Cartridge 8225 preferably includes analyte sensors configured to test for different analytes. For example, some sensors may test for glucose levels while other sensors test for fructosamine levels. Furthermore, cartridge 8225 can have at least one test strip capable of testing for two analytes simultaneously, either by including two reactants within one absorbing material or by including two different analyte sensors on one test strip.

Cartridge 8225 also preferably includes an inner desiccant liner for protecting the plurality of test strips from exposure to moisture. For example, a liner can be disposed between the test strips and the inner wall of cartridge 8225, thus surrounding all the test strips (e.g., an inner sleeve). In addition, all cartridge apertures are preferably sealed with a pull-away adhesive label. Alternatively, a "sacrificial strip" can be included at the top of the stack of test strips. The sacrificial strip can be configured such that it corks and seals all apertures in cartridge 8225. In this manner, cartridge 8225 seals and protects the analyte sensors of the plurality strips from exposure to moisture and dust. The labels and/or sacrificial strip can be removed and discarded just prior to loading the cartridge into device 8200. Cartridge 8225 also preferably includes gaskets and/or o-rings at all cartridge apertures. These gaskets can be configured to mate with components of device 8200 such that a seal is provided to protect the plurality of test strips from moisture while the cartridge is loaded in device 8200 and not in use. It is also contemplated that lancet cartridge 8215 could also include pull-away labels, seals, gaskets, and liners to protect the lancets from germs, bacteria, viruses, dirt, and other contamination.

Figure 31:
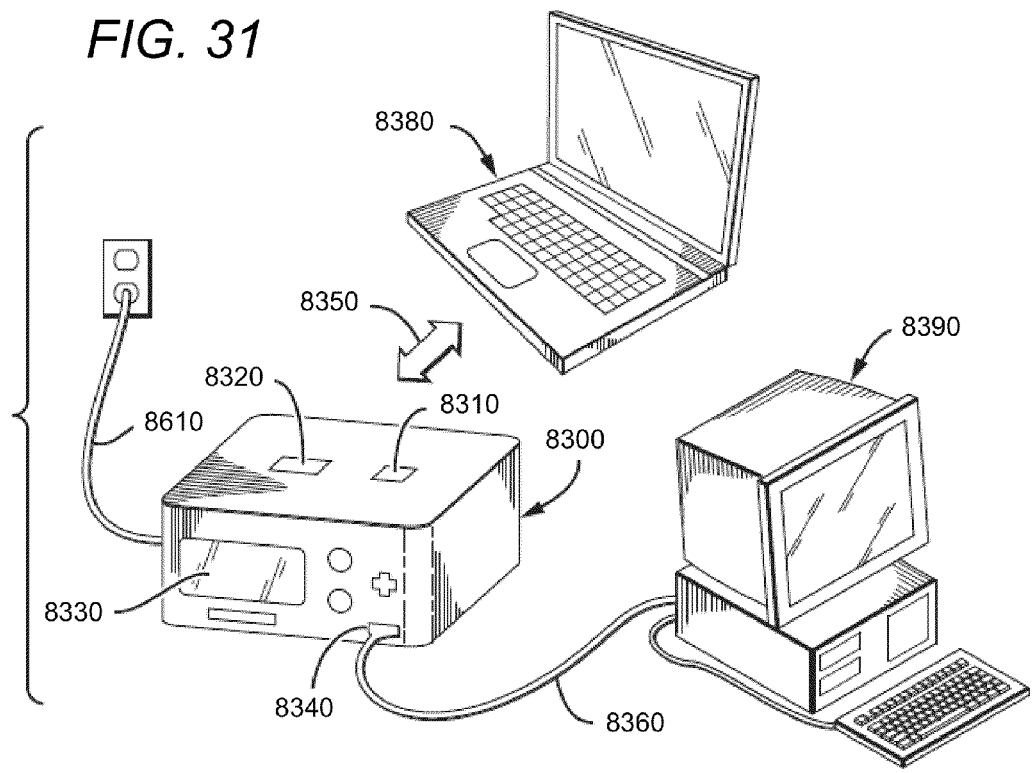
FIG. 31 is a perspective view of a docking station communicatively coupled with two external devices.

FIG. 31 shows docking station 8300 communicatively coupled with laptop 8380 and personal computer 8390. Station 8300 has a power cord 8610 for supplying power to station 8300 and device 8200. Docking station 8300 and laptop 8380 are communicatively connected via wireless connection 8350. Connection 8350 can comprise any wireless protocol, for example Bluetooth, wifi, 802.11, and cellular networks. Personal computer 8390 is connected to docking station 8300 via wired connection 8360 and data interface 8340. In one embodiment, connection 8360 is a USB cord and interface 8340 is a USB port.

Connections 8350 and 8360 can be used to back up data, transmit data to a health care provider's server via the internet, reorder supplies, receive notifications from a doctor, or receive data analysis reports from analytics software running on the external device. Furthermore, it is contemplated that docking station 8300 can connect to other external devices (e.g., smart phone, handheld health-monitoring device, insulin pen).

Figure 32:
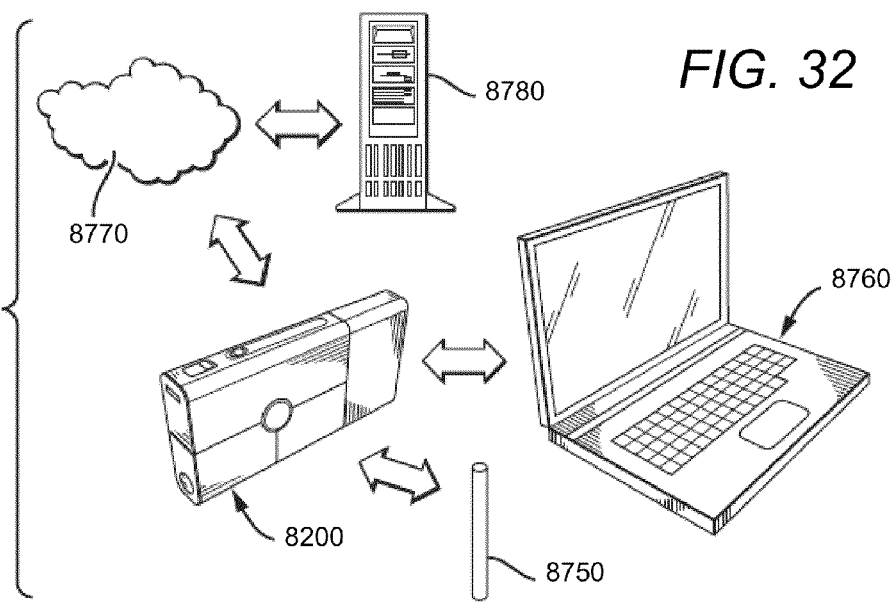
FIG. 32 is a perspective view of a handheld analyte testing device communicatively coupled with two external devices.

FIG. 32 shows testing device 8200 in wireless communication with an insulin pen 8750, laptop 8760, and local area network (LAN) 8770. In some embodiments, the insulin pen sends medication administration data (e.g., dosage administered, time of day, patient name) to device 8200. The electronics of device 8200 preferably correlates the medication administration data with the test data and non-test data, either time stamps or by some other correlative attribute. Device 8200 can use communication with LAN 8770 to upload data to a medical server 8780, or otherwise exchange data with a third party. Alternative, LAN 8770 could comprise a cellular network. It is also contemplated that device 8200 could communicate with an external device (e.g., insulin pen, handheld health monitoring device) via a wired connection.

In another embodiment of the disclosed technology, systems, devices, and methods are described for a test unit cartridge that houses: (i) a first test unit having a first analyte sensor that includes a first reagent used to detect a first analyte; and (ii) a second test unit having a second analyte sensor that includes a second reagent used to detect a second analyte different from the first analyte, such that the first test unit is not functionally fungible with the second test unit.

In some implementations of this disclosed embodiment, the test unit comprises a single strip. With reference to this disclosed embodiment, the term "strip" means a thin (less than 5 mm thick) elongated object having at least one analyte sensor. A test unit can also comprise a non-strip configuration, such as a capsule more than 5 mm thick, or a disk. In some implementations, the first test unit has no other analyte sensors besides the first analyte sensor. Alternatively, the first test unit can include an additional analyte sensor that detects the second analyte. In some implementations, the cartridge includes a "sacrificial" test unit disposed at a beginning of an order of use of the cartridge. The sacrificial test unit is configured to provide a moisture barrier by corking and sealing all apertures of the cartridge. The "sacrificial" test unit can optionally include at least two analyte sensors for detecting multiple analytes. It is also contemplated that each test unit can include features that cork the apertures of the cartridge such that the test units are protected from moisture and dust when not in use. In some implementations, the test unit cartridge includes a third through twentieth test unit, each of which is functionally fungible with the first test unit. In some implementations, the first reagent and second reagent are different. For example, the first reagent is configured to bind with a first analyte and the second reagent is configured to bind with a second analyte. In some implementations, the cartridge includes pull-away labels that cover every aperture of the cartridge in order to provide a seal and barrier from moisture and dust. In some implementations, the cartridge includes an aperture that allows an electrical contact of the first test unit to directly couple with an electrical contact of an analyte testing device. In some implementations, the test unit cartridge has a plurality of test units, wherein at least one of the test units has a first and second analyte sensor configured to detect a first and second analyte, respectively. The first and second analyte sensors can be completely non-overlapping, partly overlapping, or completely overlapping. In some implementations, the first and second analyte sensors are physically separated by a distance. In some implementations, the test unit cartridge includes a calibration test unit and an operating test unit. With reference to this disclosed embodiment, the term "calibration test unit" means a test unit having a known analyte presence and configured to test the accuracy of an analyte testing device (e.g., glucose meter). With reference to this disclosed embodiment, the term "operating test unit" means a test unit having an analyte sensor that is configured to detect an analyte. In some implementations, the test unit cartridge has a plurality of test units and a spring. The spring is disposed in a manner such that each test unit is advanced into a usable position after a previous test strip has been laterally ejected from the cartridge. In some implementations, the test unit cartridge houses a plurality of test units in a stacked configuration.

Figure 33:
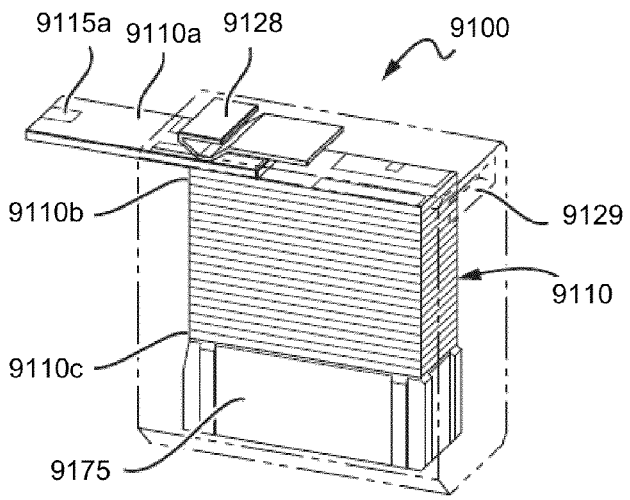
FIG. 33 is a perspective view of one embodiment of a test unit cartridge for housing a plurality of test units.
Figure 34:
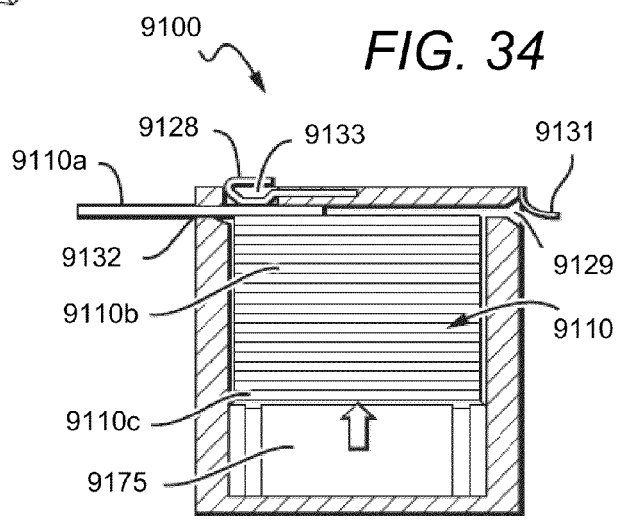
FIG. 34 is a side view of the test unit cartridge of FIG. 33.

FIGS. 33 and 34 show perspective and side views, respectively, of a test unit cartridge 9100. Cartridge 9100 holds a plurality of test units 9110 in a stacked configuration. The stacked configuration of test units 9110 advantageously allows cartridge 9100 to have a compact and simple design that requires minimal material. Cartridge 9100 is configured to couple with an analyte testing device. For example, cartridge 9100 has electrical contacts 9128 for communicatively coupling the test units 9110 with conversion electronics in an analyte testing device. Cartridge 9100 also has a slot 9129 that couples with a linkage mechanism of an analyte device, wherein the linkage is configured to push a portion of a test unit out of cartridge 9100 in order to expose analyte sensor 9115. Cartridge 9100 is preferably sized and dimensioned to mate with a compartment of an analyte testing device.

Cartridge 9100 can include any appropriate number of test units, preferably between 15 and 25 test units, more preferably between 18 and 22 test units, and most preferably 20 test units. Cartridge 9100 includes test units configured to test for different analytes. For example, test unit 9110a has an analyte sensor 9115a, which includes an analyte-binding reagent configured to test for glucose. Test unit 9110b has two analyte sensors (sensor 9115b and sensor 9116b) for detecting two different analytes (e.g., glucose and iron) using only one fluid sample. Cartridge 9100 also has a calibration test unit 9110c that has two analyte sensors: sensor 9115c is for detecting glucose and calibration sensor 9116c is for checking the accuracy of an analyte meter.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

Cartridge 9100 can include a test unit that is functionally fungible with 9110b or 9110c at every $n^{th}$ test unit within the plurality of test units 9110 in order to ensure that certain health data is gathered at particular intervals. For example, in one embodiment cartridge 9100 holds twenty test units, wherein the first and third through twentieth test units are configured to detect glucose, and the second test unit is configured to detect glucose and fructosamine. In this manner, fructosamine levels are monitored at every second test unit of every test unit cartridge.

The housing of cartridge 9100 can be made of plastic, metal, composite, or any other material with structural and mechanical properties suitable for housing a plurality of test units. Cartridge 9100 is preferably compact, with a height no more than 25 mm, a width no more than 15 mm, and a length no more than 50 mm. In some embodiments, the height is no more than 20 mm, a width is no more than 8 mm, and a length is no more than 40 mm.

Cartridge 9100 also preferably includes an inner desiccant liner (not shown) for protecting the plurality of test units from exposure to moisture. For example, a liner can be disposed between the test units and the inner wall of cartridge 9100, thus surrounding all the test units (e.g., an inner sleeve). In some embodiments, the liner comprises a crystalline structure configured to absorb moisture and prevent moisture from reaching the analyte sensors. Liners are well known and all materials suitable for absorbing and/or blocking moisture are contemplated. In addition, all cartridge apertures are preferably sealed with a pull-away adhesive label. For example, pull-away label 9131 has been placed over slot 9129 in order to seal slot 9129, thus protecting test units 9110 from exposure to moisture and dust. Preferably, slot 9132, slot 9133 and all other orifices/apertures of cartridge 9100 are sealed with a pull-away label. The labels can be removed just prior to loading cartridge 9100 into device 9600 (see FIG. 38). Cartridge 9100 also preferably includes gaskets and/or o-rings at all cartridge apertures. These gaskets can be configured to mate with components of device 9600 such that a seal is maintained while cartridge 9100 is loaded in device 9600 and not in use.

Cartridge 9100 also includes a spring 9175, which is disposed below the plurality of test units 9110 and is configured to push the test units 9110 upward. In this manner, each test unit is pushed up into a usable position after the previous test unit is laterally ejected out of slot 9132.

Cartridge 9100 provides several advantages. First, by providing a plurality of test units in one disposable and replaceable cartridge, methods and devices for monitoring analytes is significantly simplified. Second, cartridge 9100 provides a means for ensuring that secondary health data is gathered at predetermined intervals. For example, a diabetes patient monitoring glucose levels (i.e., primary health data) will nonetheless monitor secondary health data (e.g., fructosamine levels) when test unit 9110b is used. Third, cartridge 9100 allows primary and secondary health data to be gathered simultaneously in a single blood sample. Fourth, cartridge 9100 provides an enclosure that protects a plurality of test units from exposure to moisture and dust. Finally, cartridge 9100 provides a simple mechanism for advancing each test unit into place after the previous test unit has been removed and disposed.

Figure 35:
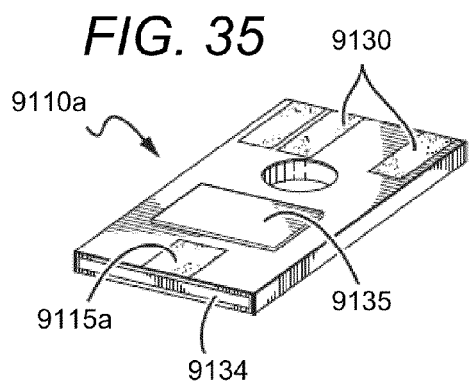
FIG. 35 is a perspective view of one embodiment of a test unit.

FIG. 35 shows a test unit 9110a, which has an analyte sensor 9115a. Analyte sensors are well known and generally comprise an absorbent material that includes a reagent (e.g., an analyte-binding reagent). In this case, sensor 9115a is configured to detect glucose. The sensor 9115a is configured to generate a signal that is sent to electrical contacts 9130. Electrical contacts 9130 are communicatively coupled with electrical contacts 9128 of cartridge 9100, thus allowing the signal to reach conversion electronics in an analyte testing device (e.g., a glucose meter). Alternatively, electrical contacts 9130 could directly interface with an analyte testing device's conversion electronics via an open aperture on cartridge 9100 (e.g., slot 9133 with contacts 9128 removed). In this manner, test unit 9110a allows a diabetic patient to monitor glucose levels. As used herein, "analyte sensor" refers to an independently interpretable signal representing an amount of an analyte present in a fluid sample. Under this definition, one piece of absorbent material having one reagent that is capable of binding to two different analytes at the same time, would be considered two separate "analyte sensors" if two independently interpretable signals are produced, regardless of whether the signal is interpreted using two different lead wires or using one lead wire (e.g., one signal having two frequency spikes that represent the amount of two different analytes present in the fluid sample).

Test unit 9110a also advantageously includes a first sealing surface 9134 and a second sealing surface 9135, configured to restrict entry of moisture into the interior of cartridge 9100 via slots 9132 and 9133, respectively. Test unit 9110a is disposed at the beginning of the order of use of the plurality of test units 9110 in cartridge 9100 (i.e., on top of the stack of test units 9110, see FIG. 33). As such, test unit 9110a serves to protect the plurality of test units 9110 from damage caused by moisture and dust. Test unit 9110a can either be a "sacrificial unit," meaning its sole purpose is to provide a cork/seal to the orifices of cartridge 9100, or can optionally include analyte sensors, such as analyte sensor 9115a. Test unit 9110a also preferably includes a sealing surface on its back side to provide a seal at slot 9129. It is also contemplated that each of the plurality of test units 9110 can include sealing surfaces to protect each subsequent test unit from moisture.

While FIG. 35 shows test unit 9110a having a "strip" configuration, those of skill in the art will appreciate that other shapes can be used consistently with the inventive subject matter disclosed herein. For example, test unit 9110a could comprise a capsule or a disk rather than a strip. However, stackable test units are preferred in order to conserve space.

Figure 36:
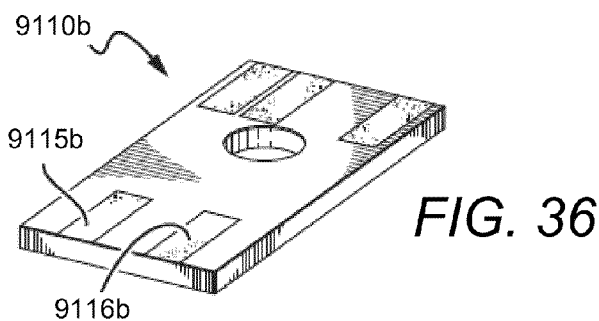
FIG. 36 is a perspective view of another embodiment of a test unit.

FIG. 36 shows a test unit 9110b, which has two analyte sensors 9115b and 9116b. Sensor 9115b is configured to detect glucose, while sensor 9116b is configured to detect fructosamine. Test unit 9110b advantageously provides a means for testing for two analytes using one blood sample (i.e., from a single prick and a single test unit). While FIG. 36 shows sensors 9115b and 9116b in completely non-overlapping positions, it is also contemplated that sensors 9115b and 9116b could be partially overlapping, or even completely overlapping. For example, sensors 9115b and 9116b could comprise one absorbent material and one analyte-binding reagent, wherein the analyte-binding reagent is capable of simultaneously binding with two or more analytes and can produce two "distinct" signals (e.g., one signal with two different detectible frequency spikes, or two different signals representing two distinct analytes). One of skill in the art will also appreciate that additional sensors can be included on test unit 9110b for detecting additional analytes.

Test unit 9110a and test unit 9110b are "functionally non-fungible" since unit 9110a tests for glucose while unit 9110b detects glucose and fructosamine. An example of two functionally fungible test units is a first test unit that test for glucose and iron, and a second test unit that tests for glucose and iron.

Figure 37:
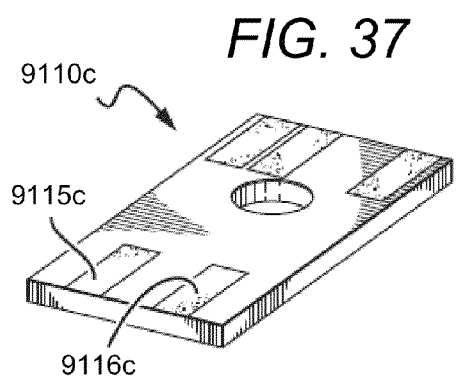
FIG. 37 is a perspective view of a calibration test unit.

FIG. 37 shows a test unit 9110c, which has two analyte sensors 9115c and 9116c. Sensor 9115c is configured to detect glucose, while calibration sensor 9116c is configured to check the accuracy of an analyte testing device. As such, sensor 9115c is an "operational sensor" and sensor 9116c is a "calibration sensor." Sensor 9116c has a known concentration of a particular analyte and produces a signal that is expected to result in a known reading on device 9600. In this manner, the electronics of device 9600 can be checked for accuracy, precision, and consistency.

Figure 38:
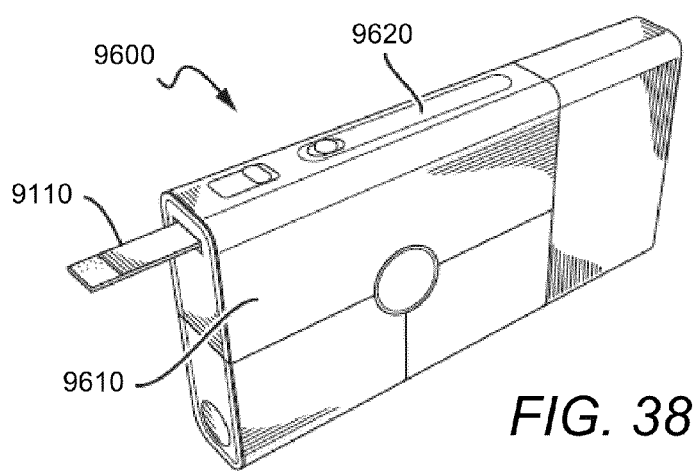
FIG. 38 is a perspective view of one embodiment of an analyte testing device.

FIG. 38 shows an analyte testing device 9600. Device 9600 is a glucose meter integrated with a lancing device. Device 9600 has an actuator 9620 and an internal linkage mechanism (not shown) configured to cock a lancet for drawing blood, partially expose a test unit for contacting with a blood sample, and reading a signal of the test unit. Device 9600 also has an internal compartment 9610 for loading and storing cartridge 9100. Device 9600 also preferably has an internal compartment for storing a cartridge of lancets (not shown). In this exemplary embodiment, the actuator is mechanically advantaged and the step of operating the actuator comprises cocking a lever. Device 9600 can further include a docking station and data management software.

In one aspect of the disclosed technology, an analyte testing device includes an analyte sensor module configured to hold a sensor cartridge structured to store analyte sensors, the analyte sensor module including an opening from which an analyte sensor advances to a testing position to expose at least a portion of the analyte sensor to outside of the analyte testing device; a lancet module configured to hold a lancet cartridge structured to store lancets; and an actuator, in which the actuator includes a button, a first linking component coupled to the button and the analyte sensor module, in which the first linking component moves in response to a movement of the button including a movement between a first position and a second position or a movement between the second position and a third position, a second linking component coupled to the button and the lancet module, in which the second linking component moves in response to a movement of the button between the first position and the second position, a third linking component coupled to the second linking component and moveable in response to a movement of the second linking component, and a lancet projecting component coupled to the third linking component, in which a single operation of the button moves the analyte sensor to the testing position and moves the lancet projecting component from an initial position to a cocked position for projecting a lancet.

Implementations of the analyte testing device can optionally include one or more of the following exemplary features. For example, the device can include a door covering the opening and coupled to the first linking component, in which the door moves to uncover the opening based on a movement of the first linking component. The button of the actuator of the device can be configured as a sliding button. The single operation can include the sliding of the button from the first position to the second position. The button can be positioned on the analyte testing device to allow the single operation to be carried out using a single hand holding the device. The lancet cartridge of the device can be structured to include a hollowed chamber for each lancet in the lancet cartridge, the hollowed chamber including an opening structured to allow the lancet projecting component to enter the chamber and impact the lancet for projection, a terminal opening structured to allow a needle component of the lancet to project out of the device, and a track to control a projection path of the lancet. The projection path of the device can be structured to be substantially straight to within a particular tolerance, thereby reducing wobble of the needle component as the lancet is projected out of the device. The actuator of the device can further include a depth adjustment component structured to include a knob located on the external side of the device connected to a plurality of steps of different lengths disposed within the device, in which one step is positioned in the projection path within the hollowed chamber to reduce the distance of projection of the lancet. The actuator of the device can further include a firing button located on the exterior of the device and coupled to the lancet projecting component when the lancet projecting component is in the cocked position. The device can include a second operation that includes the activation of the firing button to release the lancet projecting component to impact the lancet for projection. The analyte sensor of the device can be disposed in a test strip. The analyte sensor of the device can receive a testing sample from a user in the testing position. The analyte sensor of the device can be ejected from the device by a third operation that includes the movement of the button from the second position to the third position. The button of the actuator of the device can be configured as a sliding button that includes two separable buttons including a first button and a second button, in which the first button returns back to the first position after the movement of the button between the first position and the second position, and the second button is moved from the second position to the third position in the third operation. The actuator of the device can further include a button stop mechanism that prevents the button from returning to the first position when the single operation is initiated and not completed. The analyte sensor module of the device can further include a temperature sensor to monitor temperature in the analyte sensor module. The device can further include a first facility configured to transmit at least one of (a) a data obtained from the analyte sensor and (b) information derived from the data out of the analyte testing device using at least one wireless protocol. The device can further include a second facility configured to transmit at least one of the data and information derived from the data out of the analyte testing device using a wired path. The device can further include a processor configured to correlate individual instances of at least one of the data obtained from the analyte sensor and information derived from the data with (a) time stamps and optionally (b) user entered information selected from the group consisting of speech and text. The device can further include a processor configured to evaluate at least one of the data obtained from the analyte sensor and information derived from the data, and to send a notification to a recipient. The device can further include a processor configured to keep track of inventory of lancets and analyte sensors, both within and outside the device. The processor can be configured to reorder inventory of lancets and analyte sensors. The device can further include a processor configured to store voice recordings of diary information selected from the group consisting of supplies used or ordered, food eaten, exercise, medication taken, and estimated calories burned. The device can further include a processor configured to produce a prompt to direct a user to use the device according to at least one of a selected time and a selected time interval. The device can further include an LCD touch screen display, a first work light positioned to illuminate a lancet exit hole, and a second work like positioned to illuminate an analyte sensor exit slot. The device can be included in a system, in which the system can include a docking station that provides power and data connectivity to the device. The device can be included in a system, in which the system can include a visual interface external to the device, through which a user can view and input data. The device can further include a pedometer communicatively coupled with a processor configured to calculate a distance traveled and an amount of calories burned associated with the distance traveled. The device can further include a personal emergency response system (PERS) that includes a button for alerting a third party. The PERS can be configured to perform one or more of the following, e.g., including contact a third party, identify the device, provide health data associated with a user of the device, automatically contact a third party in response to health data associated with a user of the device, notify a third party as an urgency level of an emergency, and determine identity of a third party to be contacted.

In another aspect of the disclosed technology, a method for using an analyte testing device includes in a first operation, operating a button located on the exterior of an analyte testing device to advance an analyte sensor within a sensor cartridge of the analyte testing device to expose at least a portion of the analyte sensor outside of the analyte testing device and to advance a lancet projecting component of the analyte testing device from an initial position to a cocked position for a subsequent projection of a lancet; in a second operation, operating a firing button located on the exterior of an analyte testing device to advance the lancet projecting component to contact the lancet to project the lancet from the analyte testing device; and in a third operation, operating the button to eject the analyte sensor from the device, in which the first operation, second operation, and third operation are implemented using a single hand holding the device.

In another aspect of the disclosed technology, a method for operating an analyte testing device in testing an analyte includes advancing an analyte sensor from a first position within a sensor cartridge of an analyte testing device to a second position to expose at least a portion of the analyte sensor outside of the device; advancing a lancet projecting component of the analyte testing device from an initial position to a cocked position for a subsequent projection of a lancet, in which the advancing the analyte sensor and the advancing the lancet projecting component are initiated by a single operation; operating the lancet projecting component to project the lancet outside of the device; operating the device to contact the analyte sensor with a testing sample containing the analyte at the exposed portion of the analyte sensor; operating the device to process the testing sample to determine a parameter of the analyte; and ejecting the analyte sensor from the device.

Implementations of the method can optionally include one or more of the following exemplary features. For example, the method can be implemented using a single hand holding the device. The single operation can include sliding a button located on an external side of the analyte testing device. The method can further include advancing a lancet cartridge from a previous position within the analyte testing device to a readied position in which the lancet is aligned with the lancet projection component in the cocked position, in which the advancing the lancet cartridge is initiated by the single operation. Implementations of the method can include the lancet being automatically retracted back into the lancet cartridge. The method can further include operating a lancet depth adjustment component to position a step structure disposed within the device in a projection path of the lancet to control the distance of projection of the lancet. Implementations of the method can include the lancet being projected substantially straight to within a particular tolerance, thereby reducing wobble of the lancet during projection.

While the disclosed embodiments are described herein primarily based on glucose monitoring to facilitate understanding of the underlying concepts, it is understood that the disclosed embodiments can also include monitoring of other analytes that include, but are not limited to, fructosamine, hematocrit, hemoglobin blood oxygen saturation, lactates, iron, pH, cholesterol, liver enzymes (e.g., AST, ALT, ALP/GGT, LDH, bilirubin, etc.), hormones, and other compounds. For example, other biomolecular substances can also be monitored using analytical monitoring techniques of the disclosed embodiments, which include, but are not limited to, nucleic acids, lipids, carbohydrates, peptides, proteins, enzymes, hormones, antibodies, glycoproteins, glycolipids, organelles, endotoxins, and viruses, among other biological materials and biomarkers.

As used herein, and unless the context dictates otherwise, the term "coupled to" is intended to include both direct coupling (in which two elements that are coupled to each other contact each other) and indirect coupling (in which at least one additional element is located between the two elements). Therefore, the terms "coupled to" and "coupled with" are used synonymously.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. An analyte testing device, comprising:
an analyte sensor module to advance an analyte sensor upon actuation for an analyte test-and structured to include a sensor cartridge and analyte sensors stored in the sensor cartridge, the analyte sensor module including an opening from which the analyte sensor is capable to advance to a testing position to expose at least a portion of the analyte sensor to outside of the analyte testing device;
a lancet module to project a lancet upon actuation and structured to include a lancet cartridge and a plurality of lancets stored in the lancet cartridge; and
an actuator to actuate the analyte sensor module and the lancet module, the actuator including:
a button,
a first link coupled to the button and the analyte sensor module, wherein the first link is moveable in response to a movement of the button including a movement between a first position and a second position or a movement between the second position and a third position,
a second link coupled to the button and the lancet module, wherein the second link is moveable in response to a movement of the button between the first position and the second position,
a third link coupled to the second link and is moveable in response to a movement of the second link, and
a lancet projecting link coupled to the third link,
wherein the device is operable to perform a single operation of the buttons to move the analyte sensor to the testing position and to move the lancet projecting link from an initial position to a cocked position for projecting the lancet, and the device is operable to eject the analyte sensor from the device by an eject operation that includes the movement of the button from the second position to the third position,
wherein the button is a sliding button that includes two separable buttons including a first button and a second button, wherein the first button is operable to return back to the first position after the movement of the button between the first position and the second position, and the second button is operable to move from the second position to the third position in the third operation, and wherein the actuator further includes a button stop mechanism structured to include a in coupled to the button that prevents the button from returning to the first position when the single operation is initiated and not completed.

2. The device of claim 1, further comprising a door covering the opening and coupled to the first link, wherein the door is moveable to uncover the opening based on a movement of the first link.

3. The device of claim 1, wherein the single operation includes the sliding of the button from the first position to the second position.

4. The device of claim 1, wherein the button is positioned on the analyte testing device to allow the single operation to be carried out using a single hand holding the device.

5. The device of claim 1, wherein the lancet cartridge is structured to include a hollowed chamber for each lancet in the lancet cartridge, the hollowed chamber including an opening structured to allow the lancet projecting link to enter the chamber and impact the lancet for projection, a terminal opening structured to allow a needle component of the lancet to project out of the device, and a track to control a projection path of the lancet.

6. The device of claim 5, wherein the projection path is structured to be straight to within a particular tolerance, thereby reducing wobble of the needle component as the lancet is projected out of the device.

7. The device of claim 5, wherein the actuator further includes a depth adjustment component structured to include a knob located on an external side of the device connected to a plurality of steps of different lengths disposed within the device, wherein one step is positioned in the projection path within the hollowed chamber to reduce the distance of projection of the lancet.

8. The device of claim 1, wherein the actuator further includes a firing button located on an exterior side of the device and coupled to the lancet projecting link when the lancet projecting link is in the cocked position, and a second operation includes an activation of the firing button to release the lancet projecting link to impact the lancet for projection.

9. The device of claim 1, wherein the analyte sensor is disposed in a test strip and is capable of receiving a testing sample from a user in the testing position.

10. The device of claim 1, wherein the analyte sensor module further includes a temperature sensor to monitor temperature in the analyte sensor module.

11. The device of claim 1, further comprising one or both of:
a first transmitter unit including a transmitter to transmit at least one of data obtained from the analyte sensor or information derived from data out of the analyte testing device using at least one wireless protocol, or
a second transmitter unit including a transmitter to transmit at least one of the data obtained from the analyte sensor or the information derived from the data out of the analyte testing device using a wired path.

12. The device of claim 1, further comprising a processor, the processor configured to perform one or more of the following:
correlate individual instances of at least one of data obtained from the analyte sensor or information derived from data out of the analyte testing device with (a) time stamps or (b) user entered information selected from the group consisting of speech and text,
evaluate at least one of data obtained from the analyte sensor or information derived from data out of the analyte testing device, and to send a notification to a recipient,
keep track of inventory of lancets and analyte sensors, both within and outside the device, wherein the processor is configured to reorder inventory of lancets and analyte sensors,
store voice recordings of diary information selected from the group consisting of supplies used or ordered, food eaten, exercise, medication taken, and estimated calories burned, or
produce a prompt to direct a user to use the device according to at least one of a selected time or a selected time interval.

13. The device of claim 1, further comprising an LCD touch screen display, a first work light positioned to illuminate a lancet exit hole, and a second work light positioned to illuminate an analyte sensor exit slot.

14. The device of claim 1, wherein the device is configured to be in communication with a system comprising a visual interface external to the device to allow a user to view data from and input data to the device.

15. The device of claim 1, further comprising a pedometer communicatively coupled with a processor configured to calculate a distance traveled and an amount of calories burned associated with the distance traveled.

16. The device of claim 1, further comprising a personal emergency response system (PERS) that includes a button and a communication unit including a processor and a transmitter to process and transmit data, respectively, for alerting a third party upon actuation of the button of the PERS, wherein the PERS is configured to perform one or more of the following:
contact a third party,
identify the device,
provide health data associated with a user of the device,
automatically contact the third party in response to the health data associated with the user of the device,
or determine identity of the third party to be contacted.

* * * * *

UNITED STATES PATENT AND TRADEMARK OFFICE
CERTIFICATE OF CORRECTION

| | |
|---|---|
| PATENT NO. | : 8,961,432 B2 |
| APPLICATION NO. | : 13/868831 |
| DATED | : February 24, 2015 |
| INVENTOR(S) | : Gad Shaanan and Marc Goldman |

It is certified that error appears in the above-identified patent and that said Letters Patent is hereby corrected as shown below:

Title Page,

At Item 63 on Page 2 under "Related U.S. Application Data", please change "which" to --and said U.S. patent application Ser. No. 13/188,399--.

In the Claims,

At Column 34 Line 30 in Claim 1, please change "test-and" to --test and--.

At Column 35 Line 5 in Claim 1, please change "in" to --pin--.

Signed and Sealed this
Twenty-sixth Day of January, 2016

Michelle K. Lee
*Director of the United States Patent and Trademark Office*